(12) United States Patent
Linder-Ganz et al.

(10) Patent No.: US 10,758,358 B2
(45) Date of Patent: Sep. 1, 2020

(54) DEVICES, METHODS, AND SYSTEMS FOR PROSTHETIC MENISCUS SELECTION, TRIALING, AND IMPLANTATION

(71) Applicant: Active Implants LLC, Memphis, TN (US)

(72) Inventors: Eran Linder-Ganz, Tel Aviv (IL); Jacob Jonathan Elsner, Cambridge, MA (US); Avraham Shterling, Yarkona (IL)

(73) Assignee: Active Implants LLC, Memphis, TN (US)

( * ) Notice: Subject to any disclaimer, the term of this patent is extended or adjusted under 35 U.S.C. 154(b) by 177 days.

(21) Appl. No.: 16/102,418

(22) Filed: Aug. 13, 2018

(65) Prior Publication Data

US 2019/0105164 A1 Apr. 11, 2019

Related U.S. Application Data

(63) Continuation of application No. 15/400,717, filed on Jan. 6, 2017, now Pat. No. 10,045,852, which is a continuation of application No. 14/275,528, filed on May 12, 2014, now Pat. No. 9,539,100, which is a continuation of application No. 13/552,505, filed on Jul. 18, 2012, now Pat. No. 8,721,721, which is a continuation of application No. 12/547,053, filed on Aug. 25, 2009, now abandoned.

(51) Int. Cl.
  *A61F 2/38* (2006.01)
  *A61F 2/08* (2006.01)
  *A61F 2/46* (2006.01)
  *A61F 2/30* (2006.01)

(52) U.S. Cl.
  CPC .............. *A61F 2/3872* (2013.01); *A61F 2/08* (2013.01); *A61F 2/4684* (2013.01); *A61F 2002/30948* (2013.01); *A61F 2002/4666* (2013.01)

(58) Field of Classification Search
  CPC ............................ A61F 2/4684; A61F 2/3872
  See application file for complete search history.

(56) References Cited

U.S. PATENT DOCUMENTS

2005/0033424 A1* 2/2005 Fell ........................... A61F 2/38
                                                           623/14.12

\* cited by examiner

*Primary Examiner* — Andrew Yang
(74) *Attorney, Agent, or Firm* — Haynes and Boone, LLP

(57) ABSTRACT

Methods of selecting and implanting prosthetic devices for use as a replacement meniscus are disclosed. The selection methods include a pre-implantation selection method and a during-implantation selection method. The pre-implantation selection method includes a direct geometrical matching process, a correlation parameters-based matching process, and a finite element-based matching process. The implant identified by the pre-implantation selection method is then confirmed to be a suitable implant in the during-implantation selection method. In some instances, the during-implantation selection method includes monitoring loads and/or pressures applied to the prosthetic device and/or the adjacent anatomy. In some instances, the loads and/or pressures are monitored by a trial prosthetic device comprising one or more sensors. Methods of implanting meniscus prosthetic devices are also disclosed.

20 Claims, 47 Drawing Sheets

(e)

| PARAMETER: | AREA (A) | WIDTH (W) | LENGTH (L) | PERIMETER (PR) | CORONAL RELATION (C) |
|---|---|---|---|---|---|
| | MENISCUS CONTACT AREA/ TIBIA MEDIAL AREA | MENISCUS WIDTH/ MEDIAL TIBIA WIDTH | MENISCUS LENGTH/ TIBIA LENGTH | MENISCUS PERIMETER/ MEDIAL TIBIA PERIMETER | MENISCUS WIDTH/ CORONAL TIBIA WIDTH |
| DEFINITION: | $\dfrac{MA}{TMA}$ | $**\dfrac{MW_{avg}}{TMW}$ | $\dfrac{MML}{TML}$ | $\dfrac{MP}{TMP}$ | $\dfrac{MW}{TPW}$ |

270

**$MW_{avg} = \{MWA + MWP\}/2$

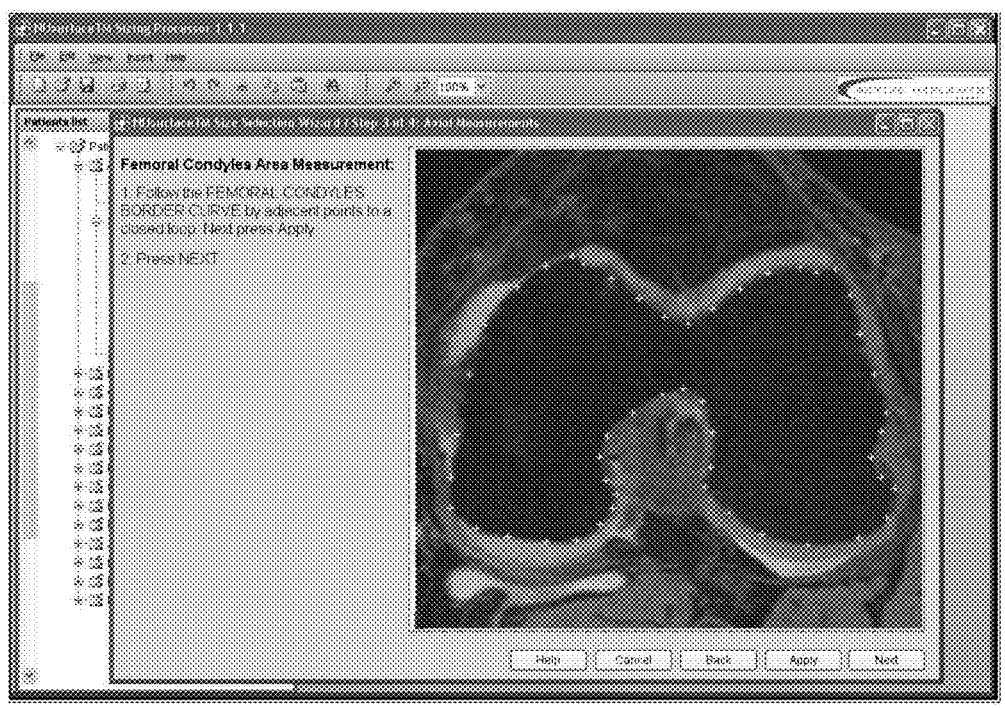
Fig. 43

DEVICES, METHODS, AND SYSTEMS FOR PROSTHETIC MENISCUS SELECTION, TRIALING, AND IMPLANTATION

CROSS REFERENCE TO RELATED APPLICATIONS

This application is a continuation of U.S. patent application Ser. No. 15/400,717, filed Jan. 6, 2017, now U.S. Pat. No. 10,045,852, which is a continuation of U.S. patent application Ser. No. 14/275,528, filed May 12, 2014, now U.S. Pat. No. 9,539,100, which is a continuation of U.S. patent application Ser. No. 13/552,505, filed Jul. 18, 2012, now U.S. Pat. No. 8,721,721, which is a continuation of U.S. patent application Ser. No. 12/547,053, filed Aug. 25, 2009, each of which is hereby incorporated by reference in its entirety.

BACKGROUND

Field

The present disclosure generally relates to medical prosthetic devices, systems, and methods. More specifically, in some instances the present disclosure relates to prosthetic devices that replace at least part of the functionality of the natural meniscus. Each knee has two menisci, a lateral meniscus and a medial meniscus. Each meniscus is a crescent-shaped fibrocartilaginous tissue attached to the tibia at an anterior and a posterior horn. Damage to the meniscus can cause pain and arthritis. Accordingly, it is desirable to replace the damaged natural meniscus with a prosthetic device. In some instances the prosthetic devices of the present disclosure are configured to be surgically implanted into a knee joint to replace or augment the natural meniscus. In many instances, it is important that the prosthetic device be of the appropriate size and shape for the intended patient and that the prosthetic device provide the appropriate functionality to the knee joint. At least in part, the methods of the present disclosure identify suitable prosthetic devices for use with a particular patient.

While existing devices, systems, and methods have attempted to address these issues, they have not been satisfactory in all respects. Accordingly, there is a need for the improved devices, systems, and methods in accordance with the present disclosure.

SUMMARY

Methods, systems, and devices for selecting, trialing, and/or implanting prosthetic devices for use as a replacement meniscus are disclosed.

In some embodiments, methods for selecting a suitable prosthetic device for a particular patient are disclosed. In some instances, the selection methods include a pre-implantation selection method and a during-implantation selection method. In some instances, the implant identified by the pre-implantation selection method is confirmed to be a suitable implant by the during-implantation selection method.

In some embodiments, prosthetic devices for use as a replacement meniscus are disclosed. In some instances, the prosthetic devices include sensors for monitoring loads and/or pressures applied to the prosthetic device and/or the adjacent anatomy. In some instances, the prosthetic devices comprise trial meniscus prosthetic devices for temporary placement within the knee joint.

Additional aspects, features, and embodiments of the present disclosure are described in the following detailed description.

BRIEF DESCRIPTION OF DRAWINGS

Other features and advantages of the present disclosure will become apparent in the following detailed description of embodiments of the disclosure with reference to the accompanying of drawings, of which:

FIG. 15 is a chart setting forth various correlation parameters according to one aspect of the present disclosure.

FIG. 43 is another screen shot of the user interface of the system for identifying a suitable prosthetic device for a patient of FIGS. 37, 38, 39, 40, 41, and 42.

DETAILED DESCRIPTION

Figure 1:
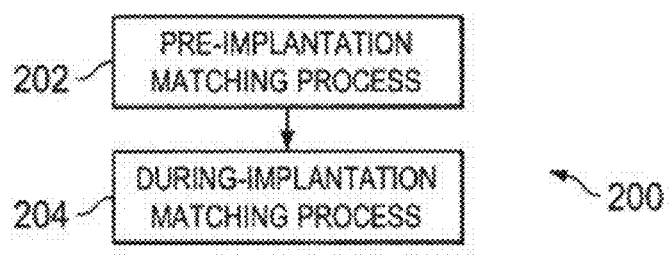
FIG. 1 is a block diagram of an embodiment of a method according to one aspect of the present disclosure for selecting an appropriate prosthetic device for use with a patient's knee.

For the purposes of promoting an understanding of the principles of the present disclosure, reference will now be made to the embodiments illustrated in the drawings, and specific language will be used to describe the illustrated embodiments. It is nevertheless understood that no limitation of the scope of the disclosure is intended. Any and all alterations or modifications to the described devices, instruments, and/or methods, as well as any further application of the principles of the present disclosure that would be apparent to one skilled in the art are encompassed by the present disclosure even if not explicitly discussed herein. Further, it is fully contemplated that the features, components, and/or steps described with respect to one embodiment may be combined with the features, components, and/or steps described with respect to other embodiments of the present disclosure.

In some embodiments, a prosthetic device is selected for a patient from a finite library or catalog of available prosthetic device. In that regard, the available prosthetic devices are of various sizes, various materials, and/or various shapes. In some instances, a selection methodology is applied to identify one or more suitable prosthetic devices and/or a best prosthetic device for a patient based on the patient's anatomical features. In other instances, a custom prosthetic device is designed and manufactured specifically for the patient based on the patient's anatomical features. Specific methods for identifying the appropriate prosthetic device(s) for a patient will now be described. It is recognized that the methods described herein may be used individually, combined with one another, and/or combined with other methods in an effort to identify one or more suitable prosthetic devices for the patient.

In most healthy patient knees, the natural meniscus and the surrounding bone structures have substantially matching geometrical contours. Accordingly, in some instances in order to restore the function of the knee joint with a prosthetic meniscus, the prosthetic device is configured to substantially match the geometrical contours of the surrounding bone structures of the knee joint after implantation and/or mimic the function of a natural healthy meniscus. Thus, in some embodiments the geometrical attributes of the patient's knee joints and the prosthetic device are taken into consideration. In that regard, in some instances the geometrical attributes of both the patient's healthy knee and the patient's damaged knee are considered, including the bone structures, the articular cartilage, and/or the menisci.

Referring now to FIG. 1, shown therein is a method 200 for identifying at least one suitable prosthetic device for a patient. The method 200 includes a pre-implantation matching process at step 202 and a during-implantation matching process at step 204. The pre-implantation and during-implantation matching procedures 202 and 204 described herein are utilized for both medial and lateral meniscus replacements in both the left and right knees. The method 200 begins at step 202 with the pre-implantation matching process. The pre-implantation matching process of step 202 is comprised of one or more matching methods.

Figure 2:
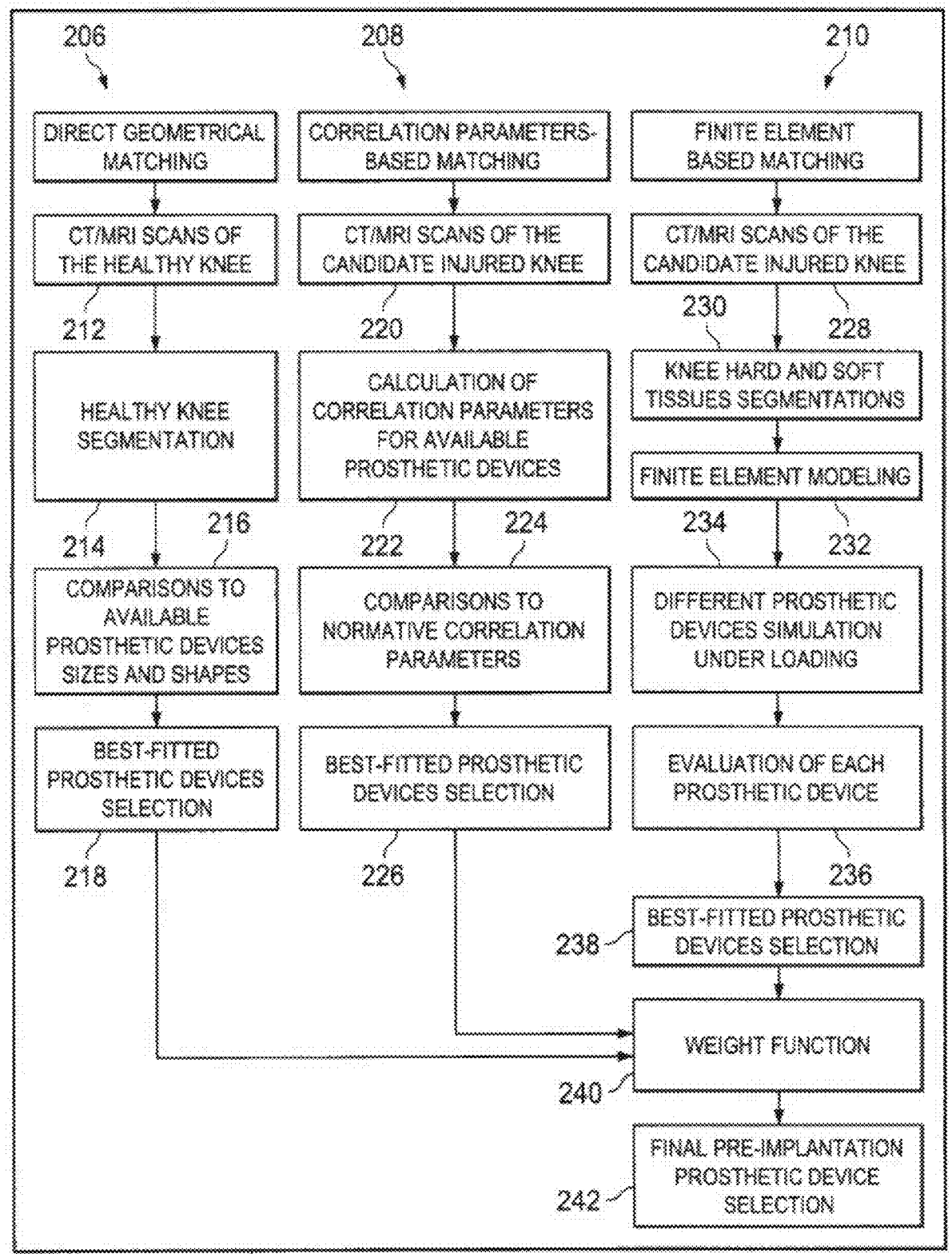
FIG. 2 is a block diagram of an embodiment of a method according to one aspect of the present disclosure for selecting an appropriate prosthetic device for use with a patient's knee prior to surgery.

Referring to FIG. 2, in the present embodiment the pre-implantation matching process 202 comprises three different matching methods: a direct geometrical matching method 206, a correlation parameters-based matching method 208, and a finite element-based matching method 210. Each of these three matching processes 206, 208, and 210 is described in greater detail below. While these processes 206, 208, and 210 are described as being used together, in some instances only one or two of the three methods are utilized in the pre-implantation matching process 202. In other instances, the processes 206, 208, and 210 are utilized in combination with additional and/or alternative matching processes.

The direct geometrical matching process 206 begins at step 212 where CT, MRI, and/or medical imaging scans of the healthy knee of a candidate patient are obtained. In some instances, the CT, MRI, and/or medical imaging scans of the healthy knee are utilized to obtain measurements of the patient's knee structures in an effort to identify the appropriate prosthetic device for the damaged knee. While the present disclosure specifically refers to CT and MRI scans, it is fully contemplated that other medical imaging methods may be utilized. Accordingly, it is fully contemplated that alternative medical imaging devices and methods now known or in the future developed may be utilized with any and all of the methods described herein.

Figure 3:
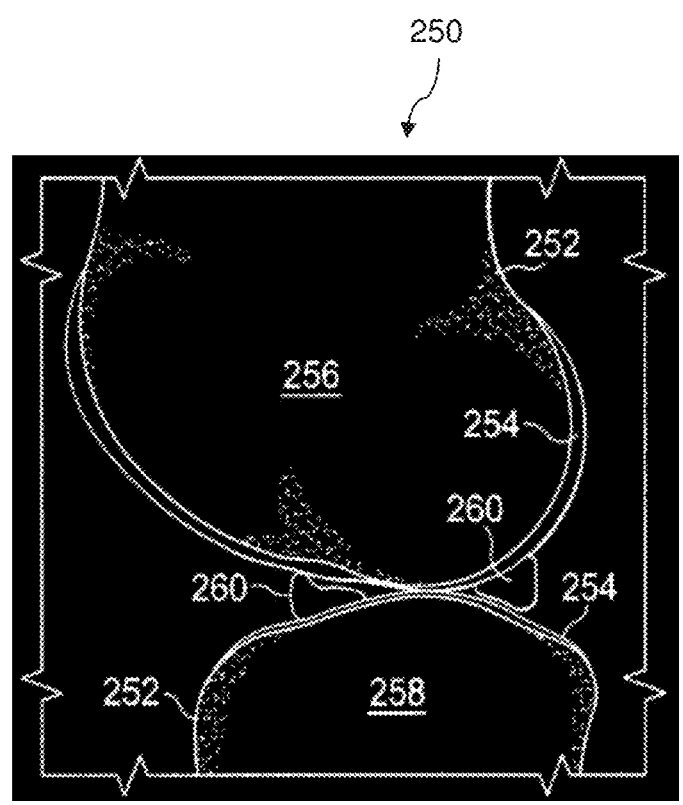
FIG. 3 is a diagrammatic side view of a rendering knee joint where the bone, articular cartilage, and meniscus have been segmented according to one aspect of the present disclosure.

At step 214, the healthy knee joint is segmented into its various components. In some embodiments, image-processing algorithms are utilized to segment the knee joint. In some embodiments, one or more of the bone surfaces, the articular cartilage, and the meniscus of the knee joint are segmented. For example, referring to FIG. 3, shown therein is a diagrammatic side view of a patient's right knee joint 250 where the bone surfaces 252 and articular cartilage 254 of the femur 256 and the tibia 258 have been segmented. Further, the medial meniscus 260 extending between the articular cartilage 254 has been segmented. In some instances, the bone surfaces, the articular cartilage, and the meniscus are segmented in separate steps. In other instances, the segmentation of the bone surfaces, the articular cartilage, and the meniscus are performed approximately simultaneously. In some embodiments, the internal knee joint cavity is characterized based on the surfaces of the articular cartilage. In some instances, the healthy meniscus is defined at least partially based on the knee joint cavity defined by the articular cartilage.

Figure 4:
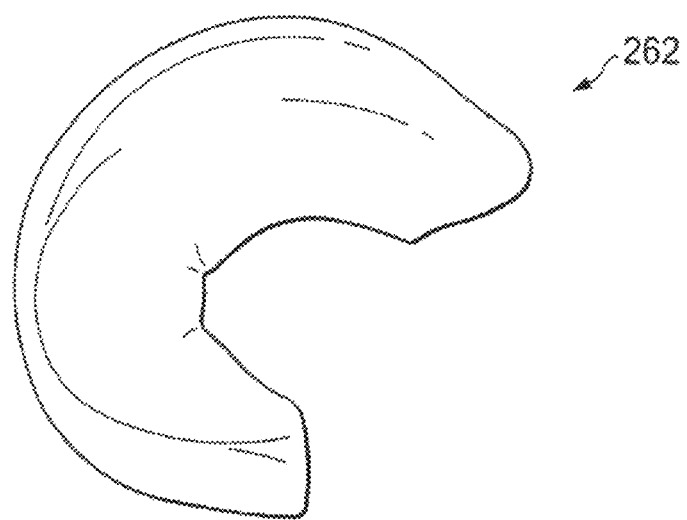
FIG. 4 is a diagrammatic perspective view of a three-dimensional reconstruction of a natural meniscus according to one aspect of the present disclosure.

Referring again to FIG. 2, in some embodiments at step 214 or a subsequent step of the direct geometrical matching process 206, a virtual solid model 262 of the healthy meniscus 260 is built graphically, as shown in FIG. 4. In some embodiments, the virtual solid model 262 is created in a stereolithography ("STL") format. In other instances, other known modeling formats are utilized. The virtual model 262 is used in some instances to compare the healthy meniscus 260 to the available prosthetic devices.

In some instances both knees of a candidate patient are damaged or at least not suitable for use as a model healthy meniscus. In such instances, a model healthy meniscus for the patient is selected from a library of model healthy menisci or formulated specifically for the patient based on the geometrical measurements of the patient's knee components. In that regard, in some embodiments a library of model healthy menisci are maintained in a database. The healthy menisci are based on one or more cadaver studies in some instances. In that regard, each model healthy meniscus is based on the attributes of a specific healthy meniscus from a cadaver, an average of the attributes of several healthy menisci for cadavers with knee components having one or more geometrical measurements in a similar size range, and/or otherwise derived from data based on the healthy menisci of the cadavers. Further, in some instances the model healthy menisci are associated with the corresponding geometrical measurements of the knee components and stored in a database such that a specific model meniscus can be selected for a patient based on the geometrical measurements of the patient's knee components compared to those associated with the model menisci.

Referring again to FIG. 2, in the present embodiment, at step 216, the segmented healthy meniscus is compared to available prosthetic devices. In some instances, this comparison includes comparing the relative sizes and shapes in terms of linear dimensions (such as depths, widths, heights, and/or radii of curvature) in the different sections or regions of the meniscus; outer surfaces (such as upper and lower contact surfaces and/or peripheral surfaces); and/or volumes. In some embodiments, each available prosthetic device is given a score or ranking based on how well it matches each of the various dimensions of the natural meniscus. By combining the scores for each of the dimensions, an overall geometrical matching score is obtained for each available prosthetic device. In that regard, it is understood that the various dimensions are weighted in some embodiments to emphasize the importance of certain dimensions. The importance or weighting of the various dimensions is determined by such factors as the patient's age, activity level, weight, body mass index, and/or other factors considered by the treating medical personnel. In some instances, the weighting function is determined by a computer system. In some instances, the weighting function is at least partially based on the answers provided to prompted questions. In other instances, the treating medical personnel manually set the weighting function of the various dimensions.

Figure 5:
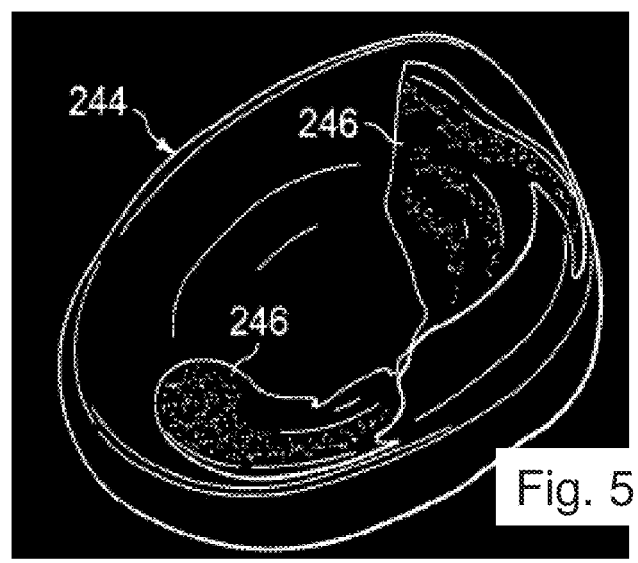
FIG. 5 is a diagrammatic perspective view of a prosthetic device for use in replacing a damaged natural meniscus according to the present disclosure shown in comparison to the dimensions of a healthy natural meniscus.

In that regard, it is understood that the best prosthetic device or a prosthetic device that will obtain the best score for a particular dimension is not necessarily one with the exact same measurements as the natural meniscus. In some instances, the prosthetic device is between 20% larger and 20% smaller than the natural meniscus. In some particular embodiments of the present disclosure the prosthetic device is approximately the same size or smaller than a natural healthy meniscus. In some embodiments the prosthetic device is generally between about 1% and about 20% smaller in volume than the natural meniscus in its relaxed pre-implantation state. Similarly, in some embodiments of the present disclosure the prosthetic device does not match the shape of the natural meniscus. For example, FIG. 5 is a diagrammatic perspective view of a prosthetic device 244 for use in replacing a damaged natural meniscus according to the present disclosure shown in comparison to the dimensions of a healthy natural meniscus 246. As illustrated, the prosthetic device 244 does not match the dimensions of the natural meniscus 246. In some instances, however, the best prosthetic device is substantially the same size and shape as the natural meniscus.

Referring again to FIG. 2, at step 218 one or more of the best-graded prosthetic devices is selected for the direct geometrical matching method as a suitable implant for the specific candidate knee. In some embodiments, only a single, best prosthetic device is identified by the geometrical matching process 206 at step 218. In other embodiments, all of the available prosthetic devices are ranked based on their score as calculated using the geometrical matching process 206. In yet other embodiments, all of the prosthetic devices suitable for the candidate knee are identified and the prosthetic devices that are not suitable are discarded as potential implant options.

As described below, the measurements and comparisons of the patient's knee and meniscus are performed substantially by electronic or automated means in some embodiments. However, in other embodiments the measurements are taken manually, directly from CT/MRI scans. Further, these manual measurements may be compared with prosthetic device measurements. The prosthetic device measurements are provided by the manufacturer in some instances. In other instances, the measurements of the prosthetic device are obtained manually as well. The manual measurements may be utilized to confirm the measurements and comparisons obtained using the image processing algorithm and matching process or in lieu of the image processing algorithm and matching process.

Referring still to FIG. 2, the correlation parameters-based matching process 208 is utilized in some embodiments. In some instances, the correlation parameters-based matching process utilizes dimension measurements based on one or more large-scale studies of patients having healthy knees. Generally, the studies consider the dimensions of a large number of patients' knees and define "normal" or acceptable ranges for the dimensions based on various patient factors. In some instances, geometrical relationships or formulas based on the measured dimensions of the bones and the menisci are determined for each healthy subject. These geometrical relationships or formulas define the correlation parameters utilized for selecting an appropriate prosthetic device in some embodiments of the present disclosure.

Figure 6:
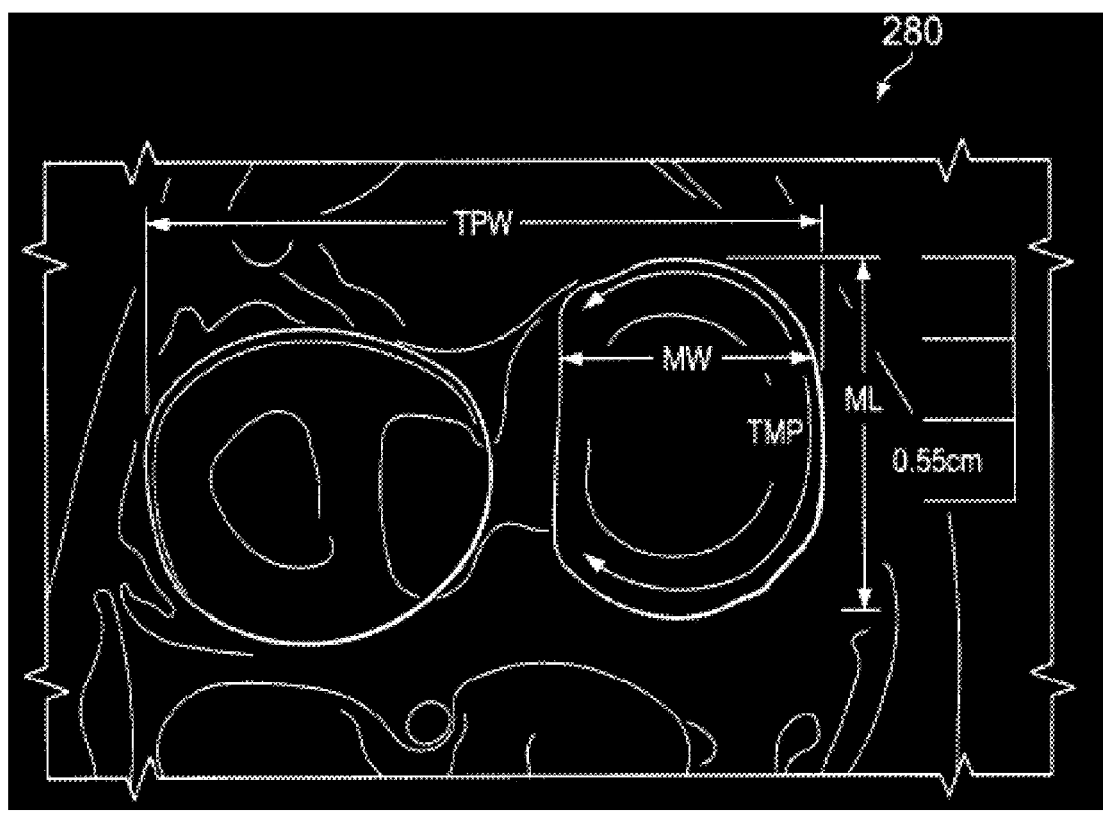
FIG. 6 is a cross-sectional top view of a knee joint based on an MRI and/or CT scan of the knee joint identifying measurements of the anatomical features of the knee joint according to one aspect of the present disclosure.
Figure 7:
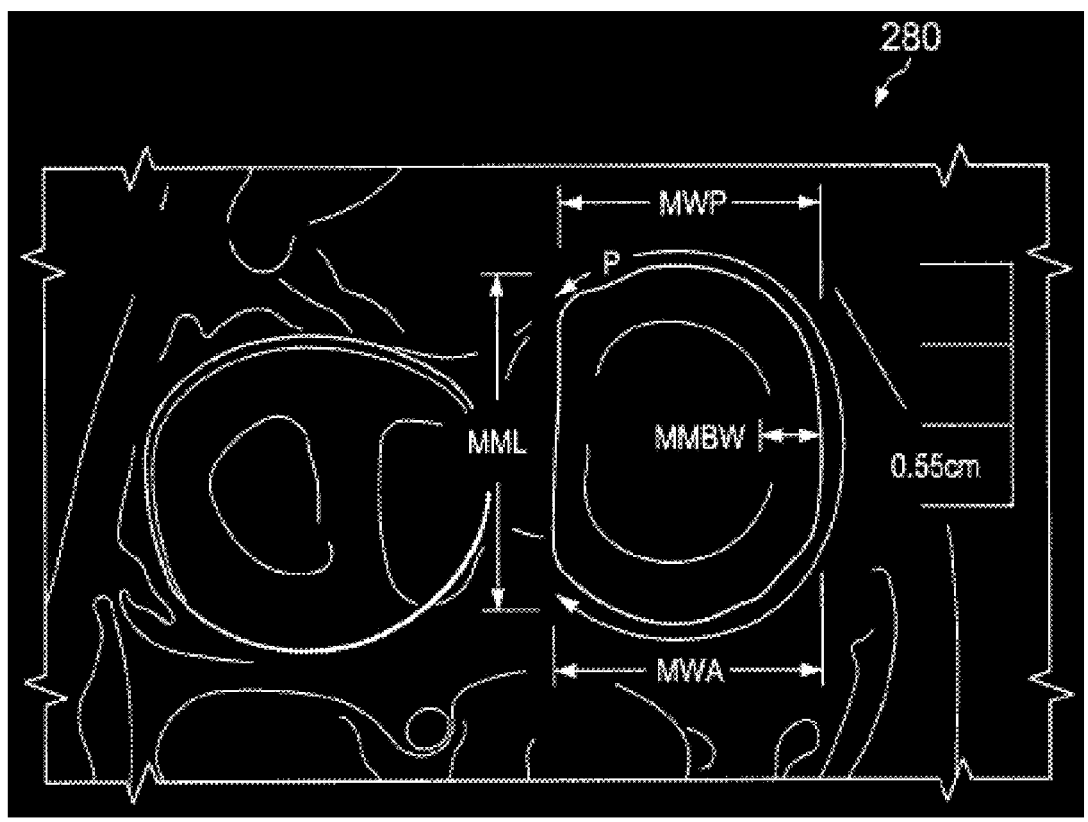
FIG. 7 is a cross-sectional top view of a knee joint based on an MRI and/or CT scan of the knee joint similar to that of FIG. 6, but identifying measurements of other anatomical features according to one aspect of the present disclosure.
Figure 8:
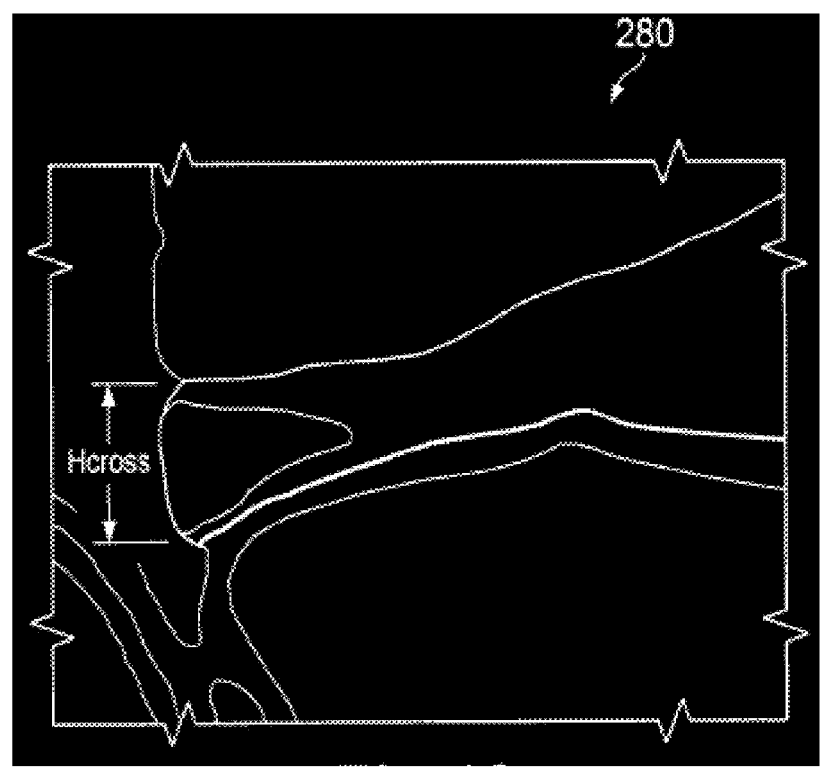
FIG. 8 is a cross-sectional sagittal view of a knee joint based on an MRI and/or CT scan of the knee joint identifying a medial meniscus height according to one aspect of the present disclosure.
Figure 9:
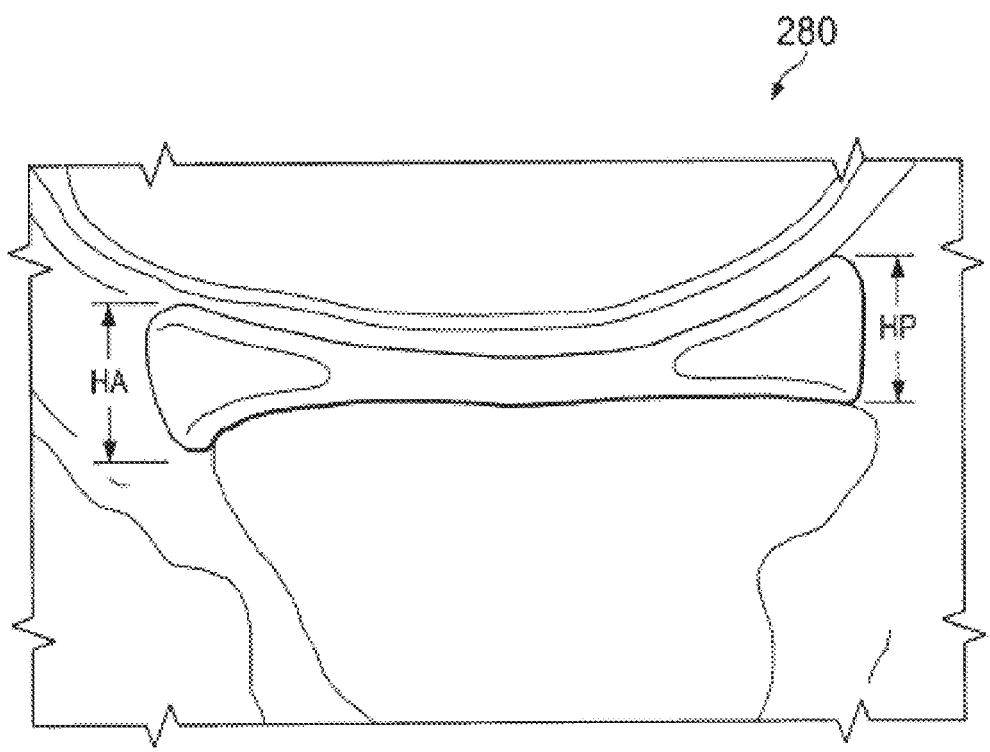
FIG. 9 is a cross-sectional side view of a knee joint based on an MRI and/or CT scan of the knee joint identifying anterior and posterior meniscus heights according to one aspect of the present disclosure.

Referring now to FIGS. 6-9, shown therein are various views of a knee joint 280 based on MRI and/or CT scans identifying measurements of the anatomical features of the knee joint. It should be noted that while these measurements are described as being based on MRI and/or CT scans in some instances, it is understood that X-ray and/or other imaging techniques are also used in some instances in the context of the present disclosure. Referring more specifically to FIG. 6, a cross-sectional top view of the knee joint 280 identifying various measurements of the anatomical features is provided. In particular, the width of the meniscus as measured in the coronal plane (labeled MW) and the coronal tibia width (labeled TPW) are identified. These parameters are utilized for calculating the coronal relation as described below. Further, the tibia medial length (labeled ML) is identified along with the tibia medial perimeter (labeled TMP). Referring more specifically to FIG. 7, a cross-sectional top view of the knee joint 280 similar to that of FIG. 6, but identifying measurements of other anatomical features is provided. Specifically, the anterior and posterior meniscus widths (labeled MWA and MWP, respectively) are provided. Also, the medial meniscus length (labeled MML) and the meniscus perimeter (labeled P) are provided. Finally, the medial meniscus body width (labeled MMBW) is provided. Referring to FIG. 8, a cross-sectional sagittal view close-up of the knee joint 280 identifying the medial meniscus height (labeled Hcross) is provided. Finally, referring to FIG. 9, a cross-sectional side view close-up of the knee joint 280 identifying anterior and posterior meniscus heights (labeled HA and HP, respectively) is provided. It is fully contemplated that additional and/or alternative views of the knee joint 280 be provided. In addition, it is fully contemplated that additional and/or alternative measurements of the knee joint 280 be provided. For example, the following Table 1 sets forth various measurements and corresponding parameter abbreviations that are utilized in some instances in conjunction with aspects of the present disclosure.

TABLE 1

Medical Imaging Measurements

| Region | Parameter | Description |
| --- | --- | --- |
| Femur | FCW | Femur Condyle Width |
|  | FCWA | Anterior Medial Femur Condyle Width |
|  | FCWP | Posterior Medial Femur Condyle Width |
|  | FW | Medial Femur Width |
|  | FWA | Anterior Medial Femur Width |
|  | FWP | Posterior Medial Femur Width |
|  | FL | Medial Femoral Condyle Length |
|  | FLM | Medial Femoral condyle Length-Medial edge |
|  | FLL | Medial Femoral condyle Length-Lateral edge |
|  | FA | Femoral condyles Area |
|  | FMA | Femoral condyle Medial Area |
| Tibia | TPW | Tibialis Plateau Width |
|  | TPWA | Tibialis Plateau Anterior Width |
|  | TPWP | Tibialis Plateau Posterior Width |
|  | MW | Tibialis plateau Medial Width |
|  | MWA | Tibialis plateau Anterior Medial Width |
|  | MWP | Tibialis plateau Medial Posterior Width |
|  | ML | Tibialis plateau Medial Length |
|  | MLM | Tibialis plateau Medial Length-Medial edge |
|  | MLL | Tibialis plateau Medial Length-Lateral edge |
|  | TA | Tibialis plateau Area |
|  | TMA | Tibialis plateau Medial Area |
| Meniscus (Intact) | MMW | Medial meniscus Width |
|  | MMWA | Anterior Medial meniscus Width |
|  | MMWP | Posterior Medial meniscus Width |
|  | MML | Medial Meniscus Length |
|  | MMLM | Medial Meniscus Length-Medial edge |
|  | MMLL | Medial Meniscus Length-Lateral edge |
|  | MMA* | Medial Meniscus effective Area |

*In some instances, MMA is assumed to be substantially elliptical and, therefore, is calculated using the equation:

$$MMA = \frac{\pi}{4} \cdot MMW \cdot MML$$

The following Table 2 identifies normal ranges for the various measurements set forth in Table 1 above for each gender and in general. As described below, these normative ranges are utilized in some instances for selecting an appropriate prosthetic device for a patient. It is understood that more specific ranges are defined in some instances based on patient characteristic information. For example, in some instances the normal ranges are determined by limiting the source data used to those data points having one or more characteristics similar to the current patient.

TABLE 2

Normative Knee Dimensions (measured in mm or mm$^2$)

| Dimension | | Female | Male | General |
|---|---|---|---|---|
| FCW | Avg. ± Std. | 73.4 ± 3.6 | 84.2 ± 4.3 | 78.7 ± 6.7 |
| | Maximal | 79.5 | 92.6 | 92.6 |
| | Minimum | 64.2 | 71 | 64.2 |
| FCWA | Avg. ± Std. | 66.6 ± 4.4 | 74.9 ± 6.5 | 70.7 ± 6.9 |
| | Maximal | 74.4 | 85.2 | 85.2 |
| | Minimum | 56 | 57.3 | 56 |
| FCWP | Avg. ± Std. | 70.2 ± 4 | 81.5 ± 4 | 75.7 ± 6.9 |
| | Maximal | 79.8 | 89.1 | 89.1 |
| | Minimum | 61.9 | 71.2 | 61.9 |
| FW | Avg. ± Std. | 27.3 ± 2.5 | 30.6 ± 3.3 | 28.9 ± 3.3 |
| | Maximal | 31.8 | 38.8 | 38.8 |
| | Minimum | 20.1 | 23.6 | 20.1 |
| FWA | Avg. ± Std. | 34.5 ± 3.1 | 39.1 ± 4.1 | 36.7 ± 4.3 |
| | Maximal | 39.6 | 45.4 | 45.4 |
| | Minimum | 25.8 | 28 | 25.8 |
| FWP | Avg. ± Std. | 24.1 ± 1.7 | 28.2 ± 2.6 | 26.1 ± 3 |
| | Maximal | 28.1 | 33.8 | 33.8 |
| | Minimum | 19.5 | 22.3 | 19.5 |
| FL | Avg. ± Std. | 50.2 ± 4.1 | 54.3 ± 4.8 | 52.2 ± 4.9 |
| | Maximal | 57.3 | 63.4 | 63.4 |
| | Minimum | 41.6 | 42.1 | 41.6 |
| FLM | Avg. ± Std. | 45.3 ± 4.3 | 49.2 ± 4.2 | 47.2 ± 4.6 |
| | Maximal | 52.7 | 56 | 56 |
| | Minimum | 36.4 | 36.4 | 36.4 |
| FLL | Avg. ± Std. | 51.8 ± 4.4 | 57.2 ± 5.1 | 54.5 ± 5.5 |
| | Maximal | 59.2 | 64.4 | 64.4 |
| | Minimum | 41.9 | 43.8 | 41.9 |
| FA | Avg. ± Std. | 2372 ± 247 | 3017 ± 274 | 2685 ± 415 |
| | Maximal | 3021 | 3514 | 3514 |
| | Minimum | 1789 | 2260 | 1789 |
| FMA | Avg. ± Std. | 1222 ± 114 | 1527 ± 148 | 1370 ± 202 |
| | Maximal | 1454 | 1857 | 1857 |
| | Minimum | 973 | 1086 | 973 |
| TPW | Avg. ± Std. | 69.5 ± 3 | 80.6 ± 3.9 | 74.9 ± 6.5 |
| | Maximal | 73.8 | 89.5 | 89.5 |
| | Minimum | 61.2 | 69.3 | 61.2 |
| TPWA | Avg. ± Std. | 63.2 ± 3.5 | 71.9 ± 4.1 | 67.3 ± 5.8 |
| | Maximal | 69.8 | 81.3 | 81.3 |
| | Minimum | 54.5 | 61.9 | 54.5 |
| TPWP | Avg. ± Std. | 67.6 ± 3.3 | 78.5 ± 3.9 | 72.9 ± 6.5 |
| | Maximal | 74.7 | 85.7 | 85.7 |
| | Minimum | 58.9 | 67.7 | 58.9 |
| MW | Avg. ± Std. | 28.1 ± 1.4 | 32.8 ± 2.1 | 30.4 ± 3 |
| | Maximal | 30.9 | 36.3 | 36.3 |
| | Minimum | 25 | 27.4 | 25 |
| MWA | Avg. ± Std. | 23.8 ± 3.3 | 26.8 ± 3.2 | 25.3 ± 3.5 |
| | Maximal | 30.4 | 32.3 | 32.3 |
| | Minimum | 15.6 | 20.1 | 15.6 |
| MWP | Avg. ± Std. | 23.9 ± 2.6 | 27.3 ± 2.7 | 25.5 ± 3.1 |
| | Maximal | 29.9 | 33.7 | 33.7 |
| | Minimum | 17.9 | 20.9 | 17.9 |
| ML | Avg. ± Std. | 42.4 ± 2.9 | 47.9 ± 4.2 | 45.1 ± 4.5 |
| | Maximal | 49.1 | 55.9 | 55.9 |
| | Minimum | 33.5 | 37.9 | 33.5 |
| MLM | Avg. ± Std. | 35.5 ± 3.4 | 40.5 ± 4 | 38.1 ± 4.5 |
| | Maximal | 46.2 | 47.6 | 47.6 |
| | Minimum | 28.5 | 31.7 | 28.5 |
| MLL | Avg. ± Std. | 45.8 ± 3.3 | 52.6 ± 4.1 | 49.1 ± 5 |
| | Maximal | 53.2 | 60.8 | 60.8 |
| | Minimum | 35.4 | 42.5 | 35.4 |
| TA | Avg. ± Std. | 2672 ± 255 | 3484 ± 347 | 3065 ± 507 |
| | Maximal | 3095 | 4301 | 4301 |
| | Minimum | 2039 | 2361 | 2039 |
| TMA | Avg. ± Std. | 1283 ± 171 | 1664 ± 208 | 1468 ± 268 |
| | Maximal | 1632 | 2080 | 2080 |
| | Minimum | 852 | 1128 | 852 |
| MMW | Avg. ± Std. | 24.7 ± 2.2 | 28.7 ± 2.4 | 26.7 ± 3.1 |
| | Maximal | 30.1 | 33.2 | 33.2 |
| | Minimum | 20.8 | 21.1 | 20.8 |

TABLE 2-continued

Normative Knee Dimensions (measured in mm or mm$^2$)

| Dimension | | Female | Male | General |
|---|---|---|---|---|
| MMWA | Avg. ± Std. | 21.3 ± 2.6 | 24.3 ± 2.9 | 22.7 ± 3.1 |
| | Maximal | 28.3 | 30.9 | 30.9 |
| | Minimum | 16.9 | 14.8 | 14.8 |
| MMWP | Avg. ± Std. | 23.8 ± 2.8 | 27.5 ± 2.4 | 25.6 ± 3.2 |
| | Maximal | 29.9 | 31.3 | 31.3 |
| | Minimum | 17.3 | 22.4 | 17.3 |
| MML | Avg. ± Std. | 38.4 ± 2.8 | 45 ± 3.5 | 41.6 ± 4.5 |
| | Maximal | 45 | 52 | 52 |
| | Minimum | 27 | 35.2 | 27 |
| MMLM | Avg. ± Std. | 33.1 ± 3.9 | 38.6 ± 4.3 | 35.7 ± 4.9 |
| | Maximal | 42.6 | 45.2 | 45.2 |
| | Minimum | 21.3 | 26.6 | 21.3 |
| MMLL | Avg. ± Std. | 39.5 ± 2.7 | 46.2 ± 3.1 | 42.8 ± 4.4 |
| | Maximal | 44.6 | 52.9 | 52.9 |
| | Minimum | 30.7 | 35.8 | 30.7 |
| MMA | Avg. ± Std. | 749 ± 102 | 1017 ± 133 | 878 ± 179 |
| | Maximal | 1050 | 1244 | 1244 |
| | Minimum | 477 | 646 | 477 |
| HA | Avg. ± Std. | 5.5 ± 1 | 6.5 ± 1.2 | 5.9 ± 1.2 |
| | Maximal | 7.7 | 8.8 | 8.8 |
| | Minimum | 3.5 | 4.4 | 3.5 |
| HP | Avg. ± Std. | 5.8 ± 1.1 | 7.2 ± 1.6 | 6.5 ± 1.5 |
| | Maximal | 8.1 | 12.7 | 12.7 |
| | Minimum | 4 | 4.8 | 4 |
| HC | Avg. ± Std. | 5.6 ± 1.1 | 6.7 ± 1.2 | 6.1 ± 1.2 |
| | Maximal | 7.7 | 8.9 | 8.9 |
| | Minimum | 3.3 | 4.4 | 3.3 |

Avg. = Average,
Std. = Standard deviation

The following Table 3 identifies normative ranges for geometric relations between some of the various measurements set forth in Tables 1 and 2 above for each gender and in general. As described below, these normative ranges are utilized in some instances for selecting an appropriate prosthetic device for a patient. It is understood that more specific ranges are defined in some instances based on patient characteristic information. For example, in some instances the normal ranges are determined by limiting the source data used to those data points having one or more characteristics similar to the current patient.

TABLE 3

Normative internal geometric relations within bones and meniscus

| Ratio type | Geometric relation | General | Male | Female |
|---|---|---|---|---|
| Width to length ratios | $\dfrac{MMW}{MML}$ | 0.64 ± 0.06 | 0.64 ± 0.06 | 0.65 ± 0.06 |
| | $\dfrac{MW}{ML}$ | 0.68 ± 0.05 | 0.69 ± 0.05 | 0.66 ± 0.05 |
| | $\dfrac{FW}{FL}$ | 0.56 ± 0.07 | 0.57 ± 0.07 | 0.55 ± 0.06 |
| Medial to total width ratios | $\dfrac{MW}{TPW}$ | 0.41 ± 0.02 | 0.41 ± 0.02 | 0.4 ± 0.01 |
| | $\dfrac{MWA}{TPWA}$ | 0.37 ± 0.04 | 0.37 ± 0.04 | 0.38 ± 0.04 |
| | $\dfrac{MWP}{TPWP}$ | 0.35 ± 0.03 | 0.35 ± 0.03 | 0.35 ± 0.03 |
| | $\dfrac{FW}{FCW}$ | 0.37 ± 0.04 | 0.37 ± 0.04 | 0.37 ± 0.03 |

TABLE 3-continued

Normative internal geometric relations within bones and meniscus

| Ratio type | Geometric relation | General | Male | Female |
|---|---|---|---|---|
| | $\dfrac{FWA}{FCWA}$ | 0.52 ± 0.02 | 0.52 ± 0.02 | 0.52 ± 0.03 |
| | $\dfrac{FWP}{FCWP}$ | 0.34 ± 0.03 | 0.35 ± 0.03 | 0.34 ± 0.02 |
| Medial to total area ratios | $\dfrac{FMA*}{FA}$ | 0.51 ± 0.02 | 0.51 ± 0.02 | 0.52 ± 0.02 |
| | $\dfrac{TMA}{TA}$ | 0.48 ± 0.04 | 0.48 ± 0.04 | 0.48 ± 0.04 |
| Middle to anterior/ posterior ratios | $\dfrac{MW}{MWA}$ | 1.22 ± 0.16 | 1.25 ± 0.15 | 1.2 ± 0.17 |
| | $\dfrac{MW}{MWP}$ | 1.2 ± 0.12 | 1.21 ± 0.12 | 1.19 ± 0.12 |
| | $\dfrac{TPW*}{TPWA}$ | 1.1 ± 0.04 | 1.13 ± 0.05 | 1.1 ± 0.04 |
| | $\dfrac{TPW}{TPWP}$ | 1 ± 0.02 | 1.03 ± 0.03 | 1.03 ± 0.02 |
| | $\dfrac{FW}{FWA}$ | 0.8 ± 0.13 | 0.8 ± 0.16 | 0.8 ± 0.1 |
| | $\dfrac{FW}{FWP}$ | 1.1 ± 0.12 | 1.1 ± 0.13 | 1.14 ± 0.1 |
| | $\dfrac{FCW}{FCWA}$ | 1.1 ± 0.07 | 1.13 ± 0.08 | 1.1 ± 0.06 |
| | $\dfrac{FCW}{FCWP}$ | 1 ± 0.03 | 1.03 ± 0.03 | 1.05 ± 0.04 |
| Middle to medial/ lateral ratios | $\dfrac{ML}{MLL}$ | 0.92 ± 0.04 | 0.91 ± 0.04 | 0.93 ± 0.04 |
| | $\dfrac{ML}{MLM}$ | 1.2 ± 0.08 | 1.2 ± 0.09 | 1.19 ± 0.08 |
| | $\dfrac{FL*}{FLL}$ | 0.96 ± 0.04 | 0.95 ± 0.03 | 0.97 ± 0.04 |
| | $\dfrac{FL}{FLM}$ | 1.1 ± 0.04 | 1.11 ± 0.04 | 1.11 ± 0.04 |

*Significant difference was found between male and female (p < 0.05)

The following Table 4 identifies normative ranges for parametric relations between some of the various measurements set forth in Tables 1 and 2 above for each gender and in general. As described below, these normative ranges are utilized in some instances for selecting an appropriate prosthetic device for a patient. It is understood that more specific ranges are defined in some instances based on patient characteristic information. For example, in some instances the normal ranges are determined by limiting the source data used to those data points having one or more characteristics similar to the current patient.

TABLE 4

Parametric relations in the knee, in respect to total tibial plateau width (TPW*):

| Geometric | | CGM | | |
|---|---|---|---|---|
| | Measure | General | Male | Female |
| Tibia | TPWA | 0.91 | 0.89 | 0.88 |
| | TPWP | 0.98 | 0.97 | 0.96 |
| | MW | 0.41 | 0.41 | 0.40 |
| | MWA | 0.34 | 0.33 | 0.33 |
| | MWP | 0.34 | 0.34 | 0.34 |
| | ML | 0.60 | 0.59 | 0.61 |
| | MLM | 0.50 | 0.50 | 0.51 |
| | MLL | 0.66 | 0.65 | 0.65 |
| | TA | 0.54 | 0.55 | 0.54 |
| | TMA | 0.26 | 0.26 | 0.26 |
| Femur | FCW | 1.05 | 1.03 | 1.05 |
| | FCWA | 0.94 | 0.93 | 0.93 |
| | FCWP | 1.03 | 1.00 | 1.00 |
| | FW | 0.39 | 0.38 | 0.39 |
| | FWA | 0.49 | 0.48 | 0.48 |
| | FWP | 0.35 | 0.35 | 0.34 |
| | FL | 0.69 | 0.67 | 0.72 |
| | FLM | 0.63 | 0.61 | 0.66 |
| | FLL | 0.72 | 0.71 | 0.73 |
| | FA | 0.48 | 0.47 | 0.48 |
| | FMA | 0.25 | 0.24 | 0.25 |
| Meniscus | MMW | 0.36 | 0.36 | 0.35 |
| | MMWA | 0.30 | 0.30 | 0.30 |
| | MMWP | 0.34 | 0.34 | 0.34 |
| | MML | 0.55 | 0.56 | 0.55 |
| | MMLM | 0.48 | 0.48 | 0.48 |
| | MMLL | 0.57 | 0.57 | 0.56 |
| | MMA | 0.16 | 0.16 | 0.15 |

CGM = Multiplication coefficient,
GM = Indicator of a specific geometric measure
*It should be noted that TPW is measured using a coronal X-ray image in some instances.

In some instances, a specific imaging protocol is utilized for obtaining the appropriate images and measurements from a patient. In that regard, a specific MRI protocol will now be described. However, it is understood that other MRI protocols and protocols that utilize other imaging systems are utilized in some instances. First, MRI scans of the patient's damaged knee and/or healthy knee are taken. In that regard, coronal, sagittal, and axial views are obtained from one or more scans, each view comprising a plurality of slices. Generally, a suitable DICOM viewer, such as the DicomWorks Viewer, is utilized to view the MRI scans. For coronal slices, the treating medical personnel finds the two extreme slices where the tibia can still be seen and then identifies the middle slice between the two extreme slices. In instances where there is an even number of slices such that there is not a single middle slice, but rather two slices adjacent to the middle, the slice where the tibia is wider is identified as the middle slice. The frame width (side to side) of the middle slice is measured and saved. Further, two slices positioned centrally between the middle slice and the tibial edges (one on each side of the middle slice) are selected, measured, and saved. Where there is an even number of slices such that there is not a single slice centrally positioned between the middle slice and the tibial edges, the slice that is closer to the middle slice is utilized. A posterior slice where the curve of the meniscus is visible is also selected, measured, and saved.

For sagittal slices, the medial side—the side away from the fibula—is identified. The medial-most slice (where the tibia is still visible) and the lateral-most slice (near the bridge where the femoral arc disappears) are identified, measured, and saved. A middle slice positioned centrally between the medial-most slice and the lateral-most slice is identified, measured, and saved. If there is an even number of slices such that there is not a single middle slice, the slice closer to the bridge is selected. Two slices positioned centrally between the middle slice and the edges (one on each side of the middle slice) are selected, measured, and saved. Where there is an even number of slices such that there is not a single slice centrally positioned between the middle slice and the edges, the slice that is closer to the middle slice is utilized. For axial slices, a proximal-most tibial slice (without visible "white spots" of the condyles) is selected, measured, and saved. Also, a distal-most femoral slice without a middle connector is selected, measured, and saved. Additional slices from these orientations are selected, measured, and saved in some instances. Further, in some instances the slices are not measured, but are saved for future use and/or measurement.

Figure 10:
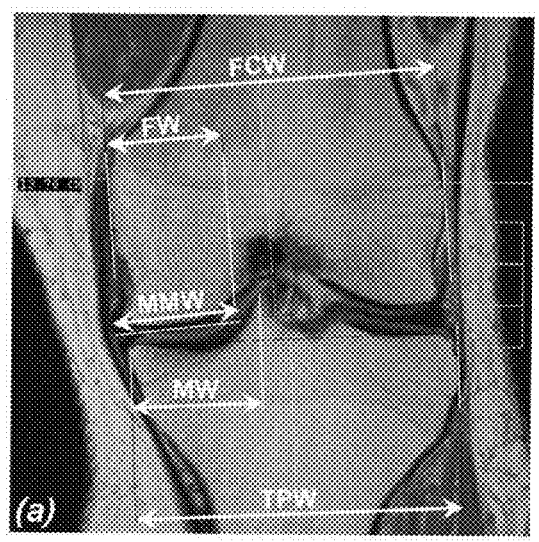
FIG. 10 is a cross-sectional front view of a knee joint based on an MRI and/or CT scan of the knee joint identifying measurements of anatomical features of the knee joint according to one aspect of the present disclosure.

In some embodiments, the slices obtained from the MRI are exported to a CAD system, such as SolidWorks, where further anatomical measurements are obtained. In some instances, each slice is imported to a different sketch (on the same plane) using the measured width of the slice as determined from the DICOM viewer. Referring to FIG. 10, for the coronal slices centerlines are placed on the proximal end of the tibia and on the distal end of the femur. In some instances, the centerlines are positioned to lie on top of the peaks of the edges of the bones. Three parallel lines are then drawn perpendicular to each centerline. In that regard, two lines are placed at the edges of the femur separated by a width FCW and a third line is placed at the gradient change seen on the medial distal edge of the femur, the third femoral line separated from one edge of the femur by a width FW. Similarly, two lines are placed at the edges of the tibia separated by a width TPW and a third line is placed at the medial peak of the tibia, the third tibial line separated from one edge of the tibia by a width MW. For the anterior coronal slice, the middle line is placed at the middle of the arc. For the meniscus slice, a vertical centerline is drawn from the tibial peak across the meniscus. A center point is marked in the middle of the vertical centerline and a horizontal centerline is drawn perpendicular to the vertical centerline through the center point. Further, a line is drawn between a center of the distal edge of the meniscus and the center point of the coronal meniscus slice, which is separated by a distance MMW.

Figure 11:
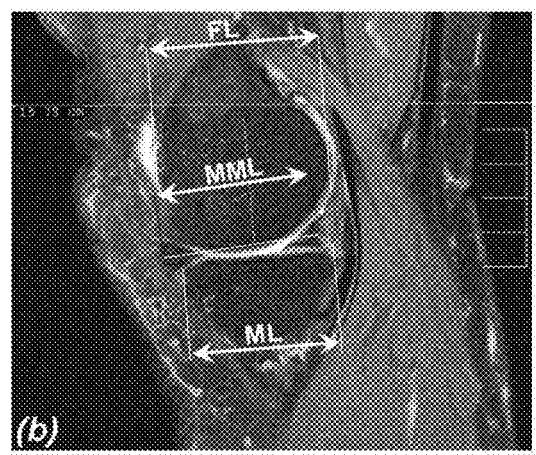
FIG. 11 is a cross-sectional side view of a knee joint based on an MRI and/or CT scan of the knee joint identifying measurements of anatomical features of the knee joint according to one aspect of the present disclosure.

Referring to FIG. 11, for the sagittal slices a centerline is placed on top of the proximal end of the tibia and four parallel lines are drawn substantially perpendicular to the centerline. Two lines are drawn at the edges of the tibia separated by a distance ML and two lines are drawn at the edges of the femur separated by a distance FL. A line is also drawn from the middle of both ends of the meniscus separated by a distance MML.

Figure 12:
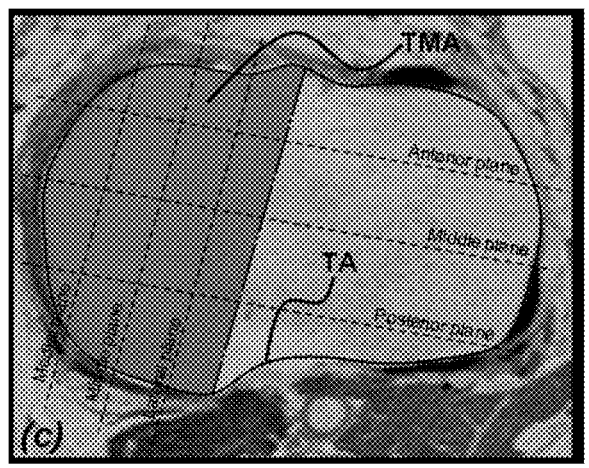
FIG. 12 is a partial cross-sectional top view of a knee joint based on an MRI and/or CT scan of the knee joint identifying measurements of anatomical features of the knee joint according to one aspect of the present disclosure.
Figure 13:
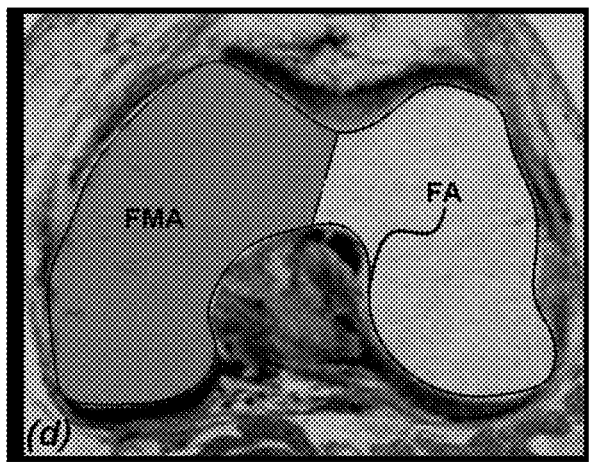
FIG. 13 is a partial cross-sectional bottom view of a knee joint based on an MRI and/or CT scan of the knee joint identifying measurements of anatomical features of the knee joint according to one aspect of the present disclosure.
Figure 14:
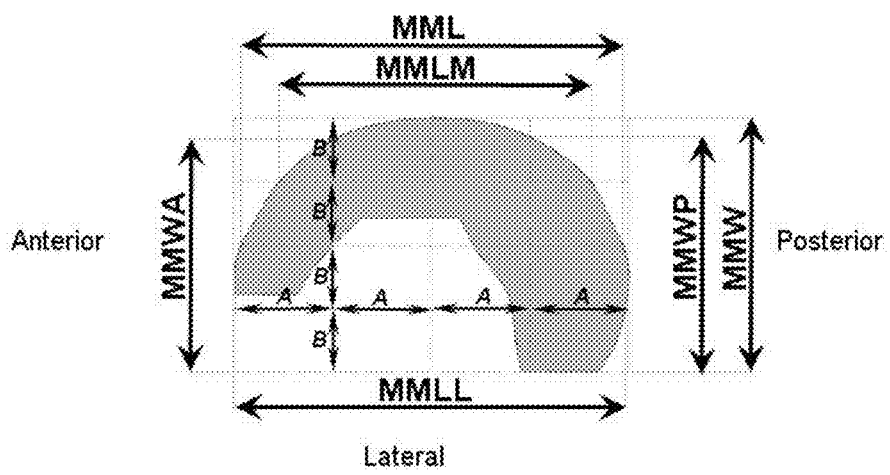
FIG. 14 is a diagrammatic top view of a meniscus identifying measurements associated with the meniscus according to one aspect of the present disclosure.

Referring to FIGS. 12 and 13, for the axial slices a spline is drawn in each slice around the femur and tibia areas. That is, in some instances a plurality of points representative of the boundaries of the femur and/or tibia areas are identified. The series of points is then interpolated to define the representative boundaries. A line is drawn on the femur slice from a central anterior boundary to a central posterior boundary. A corresponding line is drawn on the tibial slice from a central anterior boundary to a central posterior boundary. The lines on the femur and tibial slices interact with the splines. Planar surface areas for the lateral tibial area (TA), lateral femoral area (FA), medial tibial area (TMA), and medial femoral area (FMA) are determined. FIG. 14 illustrates an exemplary axial meniscus slice with the corresponding meniscal measurements discussed above identified.

Referring now to FIG. 15, shown therein is a chart setting forth various correlation parameters according to one aspect of the present disclosure. In the illustrated chart, five specific correlation parameters are identified, namely area, width, length, perimeter, and coronal relation. In other embodiments, a greater or fewer number of correlation parameters are utilized. Additional correlation parameters are discussed below. Each of the correlation parameters is defined by formula or equation comprised of dimensional measurements of the knee joint. The acceptable ranges for the correlation parameters are based on CT, MRI, and/or other medical imaging of the healthy subject patients of large-scale studies in some instances. The area correlation parameter is defined by the meniscus contact area divided by the tibia medial area, or $$A = \frac{MA}{TMA}.$$

The width correlation parameter is defined by the average meniscus width divided by the medial tibia width, or $$W = \frac{MW_{avg}}{TMW},$$

where the average meniscus width is the average of the anterior meniscus width and posterior meniscus width, or $$MW_{avg} = \frac{MW_A + MW_P}{2}.$$

The length correlation parameter is defined by the medial meniscus length divided by the tibia medial length, or $$L = \frac{MML}{TML}.$$

The perimeter correlation parameter is defined by the meniscus perimeter divided by the tibia medial perimeter, or $$P = \frac{MP}{TMP}.$$

The coronal relation correlation parameter is defined by the meniscus coronal width divided by the tibia coronal width, or $$C = \frac{MW_C}{TCW}.$$

The following Table 5 sets forth a listing of correlation parameters that are utilized in some embodiments of the present disclosure. Generally, one or more of these correlation parameters is utilized in identifying one or more suitable prosthetic devices for a particular patient in accordance with the present disclosure. In accordance with the present disclosure additional and/or alternative correlation parameters based on any of the anatomical measurements identified in Table 1 above may be utilized. Accordingly, the correlation parameters set forth herein are to be considered exemplary and do not necessarily provide an exhaustive list of suitable correlation parameters.

TABLE 5

Correlation Parameter Definitions

| Parameter | Definition | Description |
|---|---|---|
| Tibia Medial Area ratio | $\dfrac{MMA}{TMA}$ * | $\dfrac{Medial\_Meniscus\_Area}{Tibialis\_plateau\_Medial\_Area}$ |
| Tibia Area ratio | $\dfrac{MMA}{TA}$ * | $\dfrac{Medial\_Meniscus\_Area}{Tibialis\_plateau\_Area}$ |
| Femur Medial Area ratio | $\dfrac{MMA}{FMA}$ * | $\dfrac{Medial\_Meniscus\_Area}{Femoral\_condyle\_Medial\_Area}$ |
| Femur Area ratio | $\dfrac{MMA}{FA}$ * | $\dfrac{Medial\_Meniscus\_Area}{Femoral\_condyles\_Area}$ |
| Tibia Medial Width ratio | $\dfrac{MMW}{MW}$ | $\dfrac{Medial\_Meniscus\_Width}{tibialis\_plateau\_Medial\_Width}$ |
| Tibia Anterior Medial Width ratio | $\dfrac{MMWA}{MWA}$ | $\dfrac{Anterior\_Medial\_Meniscus\_Width}{tibialis\_plateau\_Anterior\_Medial\_Width}$ |
| Tibia Posterior Medial Width ratio | $\dfrac{MMWP}{MWP}$ | $\dfrac{Posterior\_Medial\_Meniscus\_Width}{tibialis\_plateau\_Posterior\_Medial\_Width}$ |
| Femur Medial Width ratio | $\dfrac{MMW}{FW}$ | $\dfrac{Medial\_Meniscus\_Width}{medial\_Femur\_Width}$ |
| Femur Anterior Medial Width ratio | $\dfrac{MMWA}{FWA}$ | $\dfrac{Medial\_Meniscus\_Width}{medial\_Femur\_Width}$ |
| Femur Posterior Medial Width ratio | $\dfrac{MMWP}{FWP}$ | $\dfrac{Medial\_Meniscus\_Width}{medial\_Femur\_Width}$ |
| Tibia Total Coronal ratio | $\dfrac{MMW}{TPW}$ | $\dfrac{Medial\_Meniscus\_Width}{Tibialis\_Plateau\_Width}$ |
| Tibia Anterior Total Coronal ratio | $\dfrac{MMWA}{TPWA}$ | $\dfrac{Anterior\_Medial\_Meniscus\_Width}{Tibialis\_Plateau\_Anterior\_Width}$ |
| Tibia Posterior Total Coronal ratio | $\dfrac{MMWP}{TPWP}$ | $\dfrac{Posterior\_Medial\_Meniscus\_Width}{Tibialis\_Plateau\_Posterior\_Width}$ |
| Femur Medial Coronal ratio | $\dfrac{MMW}{FCW}$ | $\dfrac{Medial\_Meniscus\_Width}{medial\_Femur\_Condyle\_Width}$ |
| Femur Anterior Medial Coronal ratio | $\dfrac{MMWA}{FCWA}$ | $\dfrac{Anterior\_Medial\_Meniscus\_Width}{medial\_Femur\_Anterior\_Condyle\_Width}$ |
| Femur Posterior Medial Coronal ratio | $\dfrac{MMWP}{FCWP}$ | $\dfrac{Posterior\_Medial\_Meniscus\_Width}{medial\_Femur\_Posterior\_Condyle\_Width}$ |
| Tibia Medial Length ratio | $\dfrac{MML}{ML}$ | $\dfrac{Medial\_Meniscus\_Length}{tibialis\_plateau\_Medial\_Length}$ |
| Tibia Medial Length ratio – Medial edge | $\dfrac{MMLM}{MLM}$ | $\dfrac{Medial\_Meniscus\_Length-Medial\_edge}{tibialis\_plateau\_Medial\_Length-Medial\_edge}$ |
| Tibia Medial Length ratio – Lateral edge | $\dfrac{MMLL}{MLL}$ | $\dfrac{Medial\_Meniscus\_Length-Lateral\_edge}{tibialis\_plateau\_Medial\_Length-Lateral\_edge}$ |
| Femur Width ratio | $\dfrac{MML}{FL}$ | $\dfrac{Medial\_Meniscus\_Length}{medial\_Femoral\_condyle\_Length}$ |
| Femur Medial Width ratio | $\dfrac{MMLM}{FLM}$ | $\dfrac{Medial\_Meniscus\_Length-Medial\_edge}{medial\_Femoral\_condyle\_Length-Medial\_edge}$ |

TABLE 5-continued

Correlation Parameter Definitions

| Parameter | Definition | Description |
|---|---|---|
| Femur Lateral Width ratio | $\dfrac{\text{MMLL}}{\text{FLL}}$ | $\dfrac{\text{Medial\_Meniscus\_Length} - \text{Lateral\_edge}}{\text{medial\_Femoral\_condyle\_Length} - \text{Lateral\_edge}}$ |

[1]MMA = Medial meniscus calculated area (oval area assumption) = $\text{MMA} = \dfrac{\pi}{4} \cdot \text{MMW} \cdot \text{MML}$ The following Table 6 identifies normal ranges for the various correlation parameters set forth in Table 5 above for each gender and in general. As described below, these normative ranges are utilized in some instances for selecting an appropriate prosthetic device for a patient. It is understood that more specific ranges are defined in some instances based on patient characteristic information. For example, in some instances the normal ranges are determined by limiting the source data used to those data points having one or more characteristics similar to the current patient. Table 6 sets forth the mean and standard deviation for each correlation parameter based on a large scale study. It is contemplated that additional large-scale studies may be performed in the future and that the accepted ranges for the correlation parameters discussed herein below may be adjusted, as necessary, to conform with the accepted dimensional ranges in the field.

TABLE 6

Normative Knee Geometric Relations

| Geometric relation | | Female | Male | General |
|---|---|---|---|---|
| $\dfrac{\text{MMA}^1}{\text{TMA}}$ | Avg. ± Std. | 0.59 ± 0.07 | 0.62 ± 0.08 | 0.6 ± 0.08 |
| $\dfrac{\text{MMA}^1}{\text{TA}}$ | Avg. ± Std. | 0.28 ± 0.04 | 0.29 ± 0.04 | 0.29 ± 0.04 |
| $\dfrac{\text{MMA}^1}{\text{FMA}}$ | Avg. ± Std. | 0.61 ± 0.08 | 0.67 ± 0.08 | 0.64 ± 0.08 |
| $\dfrac{\text{MMA}^1}{\text{FA}}$ | Avg. ± Std. | 0.32 ± 0.04 | 0.34 ± 0.04 | 0.33 ± 0.04 |
| $\dfrac{\text{MMW}}{\text{MW}}$ | Avg. ± Std. | 0.88 ± 0.07 | 0.88 ± 0.06 | 0.88 ± 0.07 |
| $\dfrac{\text{MMWA}}{\text{MWA}}$ | Avg. ± Std. | 0.9 ± 0.12 | 0.91 ± 0.1 | 0.9 ± 0.11 |
| $\dfrac{\text{MMWP}}{\text{MWP}}$ | Avg. ± Std. | 1 ± 0.07 | 1.01 ± 0.09 | 1 ± 0.08 |
| $\dfrac{\text{MMW}}{\text{FW}}$ | Avg. ± Std. | 0.91 ± 0.1 | 0.95 ± 0.12 | 0.93 ± 0.11 |
| $\dfrac{\text{MMWA}}{\text{FWA}}$ | Avg. ± Std. | 0.62 ± 0.06 | 0.62 ± 0.06 | 0.62 ± 0.06 |
| $\dfrac{\text{MMWP}}{\text{FWP}}$ | Avg. ± Std. | 0.99 ± 0.11 | 0.98 ± 0.1 | 0.98 ± 0.11 |
| $\dfrac{\text{MMW}}{\text{TPW}}$ | Avg. ± Std. | 0.36 ± 0.03 | 0.36 ± 0.03 | 0.36 ± 0.03 |
| $\dfrac{\text{MMWA}}{\text{TPWA}}$ | Avg. ± Std. | 0.34 ± 0.04 | 0.34 ± 0.03 | 0.34 ± 0.04 |
| $\dfrac{\text{MMWP}}{\text{TPWP}}$ | Avg. ± Std. | 0.35 ± 0.03 | 0.35 ± 0.03 | 0.35 ± 0.03 |
| $\dfrac{\text{MMW}}{\text{FCW}}$ | Avg. ± Std. | 0.34 ± 0.03 | 0.34 ± 0.03 | 0.34 ± 0.03 |
| $\dfrac{\text{MMWA}}{\text{FCWA}}$ | Avg. ± Std. | 0.32 ± 0.03 | 0.32 ± 0.03 | 0.32 ± 0.03 |
| $\dfrac{\text{MMWP}}{\text{FCWP}}$ | Avg. ± Std. | 0.34 ± 0.03 | 0.34 ± 0.03 | 0.34 ± 0.03 |
| $\dfrac{\text{MML}}{\text{ML}}$ | Avg. ± Std. | 0.91 ± 0.05 | 0.94 ± 0.05 | 0.92 ± 0.06 |
| $\dfrac{\text{MMLM}}{\text{MLM}}$ | Avg. ± Std. | 0.95 ± 0.1 | 0.97 ± 0.09 | 0.96 ± 0.09 |
| $\dfrac{\text{MMLL}}{\text{MLL}}$ | Avg. ± Std. | 0.86 ± 0.05 | 0.88 ± 0.05 | 0.87 ± 0.05 |
| $\dfrac{\text{MML}}{\text{FL}}$ | Avg. ± Std. | 0.77 ± 0.05 | 0.83 ± 0.05 | 0.8 ± 0.06 |
| $\dfrac{\text{MMLM}}{\text{FLM}}$ | Avg. ± Std. | 0.73 ± 0.06 | 0.79 ± 0.06 | 0.76 ± 0.07 |
| $\dfrac{\text{MMLL}}{\text{FLL}}$ | Avg. ± Std. | 0.77 ± 0.06 | 0.81 ± 0.06 | 0.79 ± 0.06 |

Figure 16:
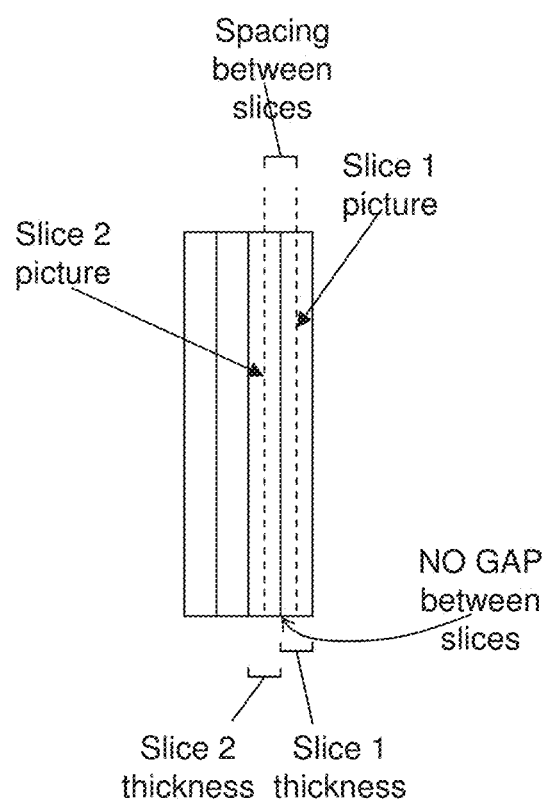
FIG. 16 is a diagrammatic schematic view of MRI slices according to one aspect of the present disclosure.
Figure 17:
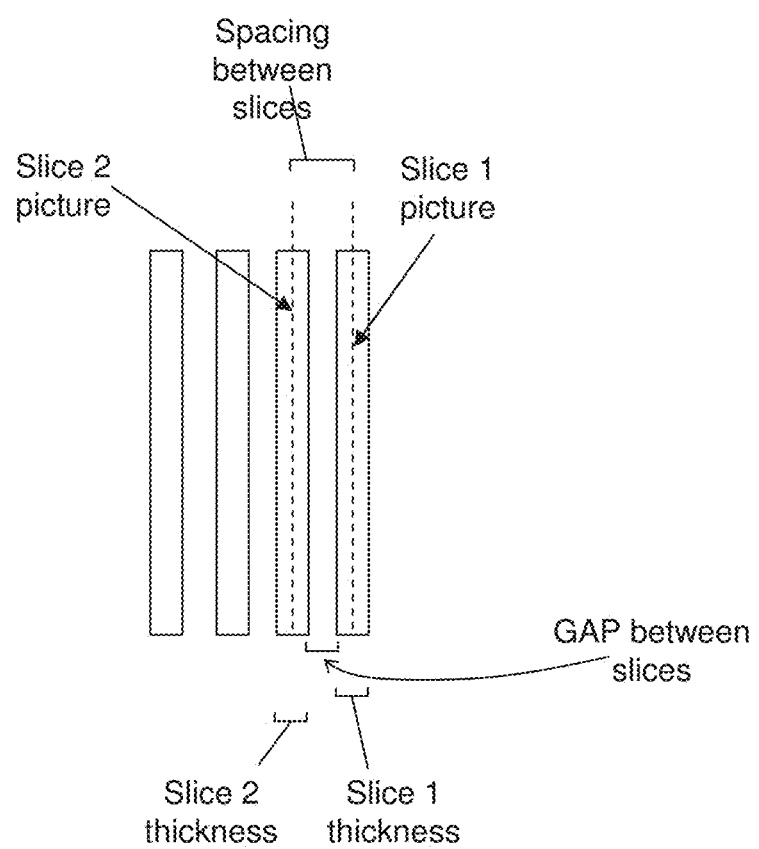
FIG. 17 is a diagrammatic schematic view of MRI slices similar to that of FIG. 16, but showing an alternative embodiment of the present disclosure.
Figure 18:
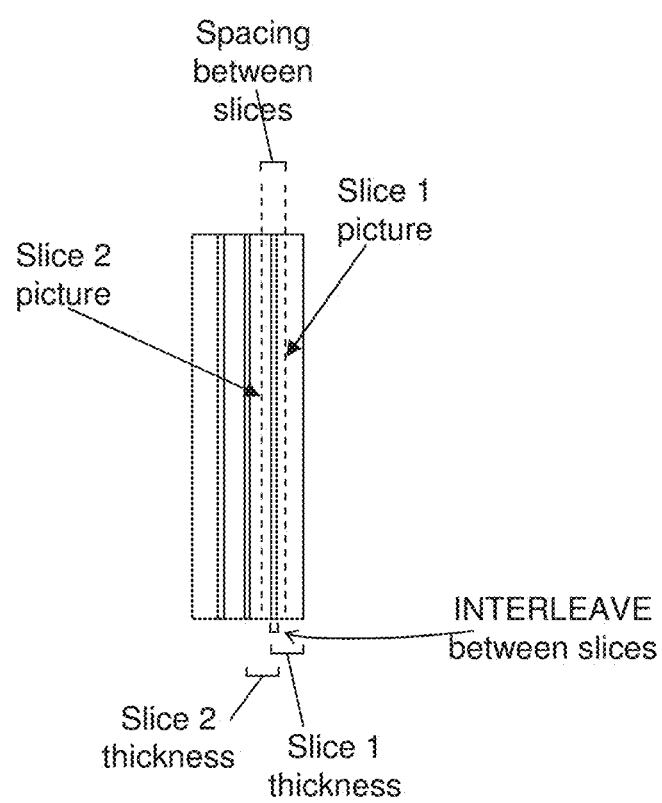
FIG. 18 is a diagrammatic schematic view of MRI slices similar to that of FIGS. 16 and 17, but showing an alternative embodiment of the present disclosure.

Avg. = Average, Std. = Standard deviation, Data is based on large scale human knee MRI-scans
[1]MMA = Medial meniscus calculated area (oval area assumption) = $\text{MMA} = \dfrac{\pi}{4} \cdot \text{MMW} \cdot \text{MML}$ In some instances, as discussed above MRI scans of the patient's knee(s) are obtained in order to determine the various measurements associated with the patient's knees. In that regard, generally any suitable MRI machine may be utilized. In some instances a 1.5 Tesla or a 3.0 Tesla MRI machine is utilized. Referring to FIGS. 16, 17, and 18, shown therein are three exemplary embodiments of different types of MRI scans that are utilized in some embodiments of the present disclosure. In that regard, FIG. 16 illustrates an MRI machine that provides scans with no gaps between imaging slices. FIG. 17 illustrates an MRI machine that provides scans with a gap between imaging slices. Finally, FIG. 18 illustrates an MRI machine that provides scans with an interleave between imaging slices.

Referring again to FIG. 2, the correlation parameters-based matching process 208 begins at step 220 where CT, MRI, and/or medical images of the injured knee of a candidate patient are obtained. Based on the imaging of the injured knee, various anatomical measurements of the knee can be obtained. For example, in some instances it is desirable to obtain information regarding the dimensions of the tibia. In that regard, the dimensions of the tibia discussed above with respect to the correlation parameters (e.g., tibia medial area, tibia medial width, tibia medial length, tibia medial perimeter, tibia coronal width, and/or other tibia dimensions) are obtained in some instances.

The process 208 continues at step 222 where the correlation parameters for one or more of the available prosthetic devices are determined. The geometrical relationship formulas of the correlation parameters are calculated for the prosthetic device based on the available candidate knee data and compared to the accepted normative data for each prosthetic device. Each prosthetic device is given a sub-grade for each correlation parameter based on how well the device matches up with the accepted ranges for that correlation parameters. In that regard, an acceptable range of values for the prosthetic device can be determined based the available measurements of the candidate knee and the normative data (e.g., normative range±standard deviation) for the candidate knee. For example, with respect to the area correlation parameter, the acceptable range of meniscus contact areas for the prosthetic devices can be determined by multiplying the normative range of acceptable areas by the tibia medial area, or A×TMA=MA. The acceptable ranges for other aspects of the prosthetic device may be calculated similarly for each of the correlation parameters.

The process 208 continues at step 224 where the calculated correlation parameters are compared to the normative or accepted correlation parameters. In some instances, the normative data is selected on a female, male, and/or general population basis. Depending on how well the prosthetic device fits within the range for each correlation parameter, a sub-grade is determined for that parameter. The better the fit, the better the sub-grade for that parameter. In some instances, the grades are binary. Meaning if the device is within the acceptable range it receives the best score and if the device is outside of the range it receives the worst score. Similar to the previous geometrical matching method, the best-graded prosthetic device is calculated by adding up all of the sub-grades to determine an overall grade. In that regard, it is understood that the various correlation parameters are weighted in some embodiments to emphasize the importance of certain correlation parameters. The importance or weighting of the correlation parameters are determined by such factors as the patient's age, activity level, weight, and/or other factors considered by the treating medical personnel. In some instances, the weighting function for the correlation parameters is determined by a computer system based on the answers provided to prompted questions. In other instances, the treating medical personnel manually set the weighting function for the correlation parameters.

Further, it is understood that the correlation parameters may vary depending on the type of implant being considered. For example, in some embodiments of the present disclosure the prosthetic devices are designed to be between about 20% larger and about 20% smaller than the natural meniscus, measured by volume. In some instances, the prosthetic devices are designed to be between about 1% and 20% smaller than the natural meniscus. Accordingly, such sizing can be taken into consideration when determining the acceptable ranges of the dimensions for the prosthetic device as they relate to the correlation parameters. At step 226, one or more of the best-graded prosthetic devices is selected for the correlation parameters-based matching process 208 as a suitable implant for the specific candidate knee. In some embodiments, only a single, best prosthetic device is identified by the correlation parameters-based matching process 208. In other embodiments, all of the available prosthetic devices are ranked based on their score as calculated using the correlation parameters-based matching process 208. In yet other embodiments, all of the prosthetic devices suitable for the candidate knee are identified and the prosthetic devices that are not suitable are discarded as potential implant options.

The finite element-based matching process 210 is utilized in some embodiments. The finite element-based matching process 210 begins at step 228 where CT, MRI, and/or other medical images of the injured knee of a candidate patient are obtained. In some instances, the same CT, MRI, and/or other medical images are utilized for both the finite element-based matching process 210 and the correlation parameters-based matching 208. Similar to the direct geometrical matching process 206 discussed above with respect to the healthy knee joint, at step 230 the injured knee joint of the patient is segmented into its various components, such as the bone, articular cartilage, and menisci. In some instances, a three-dimensional solid geometry model of the bones, cartilage, and menisci of the injured knee is built. Based on the solid geometry, a patient-specific finite element model of the knee is created at step 232. The patient-specific finite element model is configured to interface with various finite element models of prosthetic devices in some instances. In that regard, in some embodiments the finite element model does not include the natural damaged meniscus. Further, in some instances a finite element model of the patient's healthy knee is created for use in evaluating the effectiveness of the prosthetic devices in the injured knee.

The finite element-based matching process 210 continues at step 234 where several simulation cases using the finite element model are tested. First, in some embodiments a load of up to 3-times the patient's body-weight is applied by the femur on the natural, damaged meniscus. In other embodiments, the simulation of loading on the damaged meniscus is omitted. In other embodiments, a simulation of loading of the natural meniscus of the patient's healthy knee is performed and utilized as a base line. Regardless of whether a damaged or healthy meniscus is utilized, peak and average pressure measurements across the meniscus, peak and average pressure measurements acting on the femoral and tibial articular cartilage, pressure distributions across the tibialis plateau, and/or other measurements are calculated.

Figure 19:
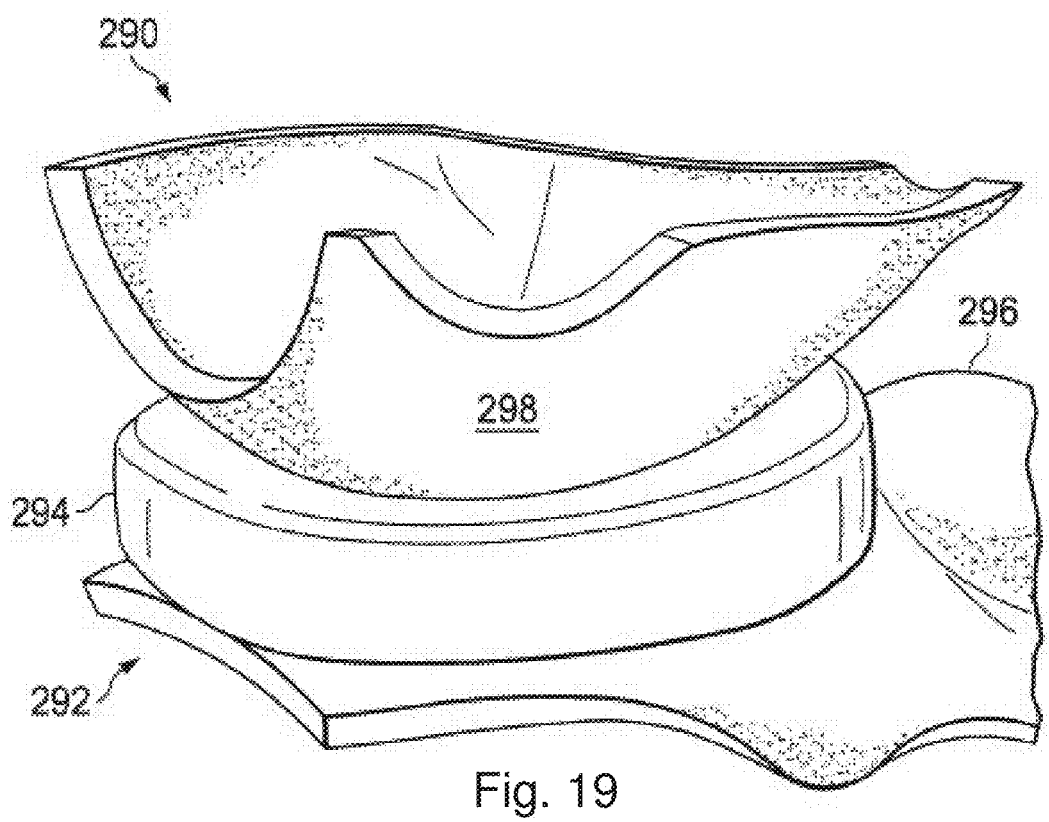
FIG. 19 is a diagrammatic perspective view of a three-dimensional finite element model of a knee joint according to one aspect of the present disclosure.
Figure 20:
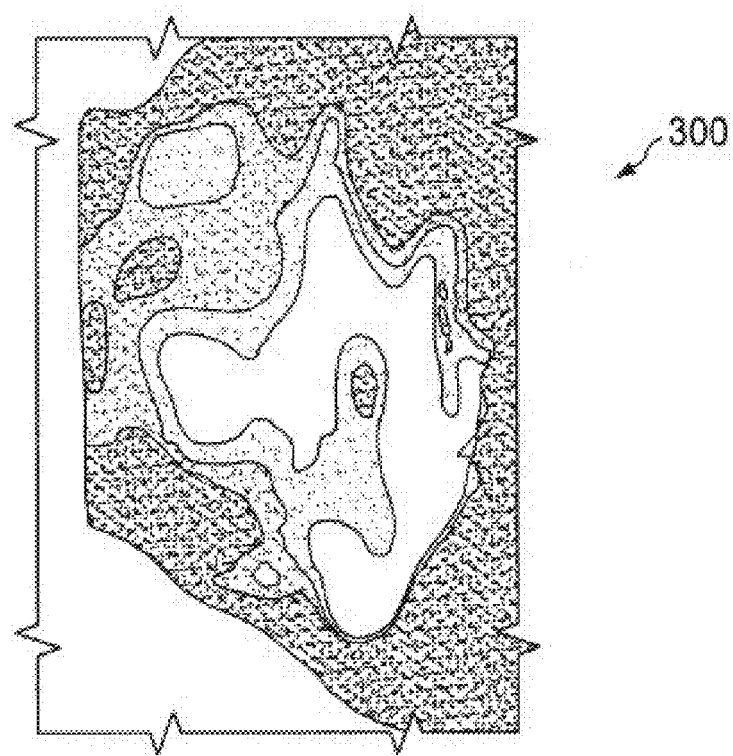
FIG. 20 is a rendering of a simulated contact pressure map between a prosthetic device and a tibialis plateau according to one aspect of the present disclosure.

Step 234 also includes testing one or more available prosthetic devices under a simulated load. Referring to FIG. 19, shown therein is a three-dimensional finite element model 290 of a knee joint 292 with a prosthetic device 294 positioned between a tibialis plateau 296 and a femur 298 according to one aspect of the present disclosure. For each of the available prosthetic devices, peak and average pressure measurements across the prosthetic device, peak and average pressure measurements acting on the femoral and tibial articular cartilage, pressure distributions across the tibialis plateau, and/or other measurements are calculated. Referring to FIG. 20, shown therein is a simulated contact pressure map 300 for the prosthetic device 294 of FIG. 19 illustrating contact pressures between the prosthetic device and the tibialis plateau 296.

At step 236, the resultant simulated pressure measurements for each of the prosthetic devices are compared to medically accepted values and/or the natural, healthy meniscus to provide the prosthetic devices with sub-grades for each of the measurements. For example, the peak pressure measurements of each of the prosthetic devices are compared to the accepted ranges or the peak pressure measurements of the natural, healthy meniscus. The extent to which the prosthetic device is within the accepted range determines the device's sub-grade for peak pressure. Similarly, the peak and average pressure acting on the articular cartilages are compared to the allowed natural values for each prosthetic device and the prosthetic device is given sub-grades accordingly. Further, the tibialis plateau pressure distributions for each prosthetic device are compared to those of a healthy natural meniscus in terms of contact area size and stress concentrations. In one particular embodiment, a prosthetic device is given a perfect sub-grade score if the resultant pressure distribution across the tibialis plateau is within ±15% of a healthy natural meniscus.

Figure 21:
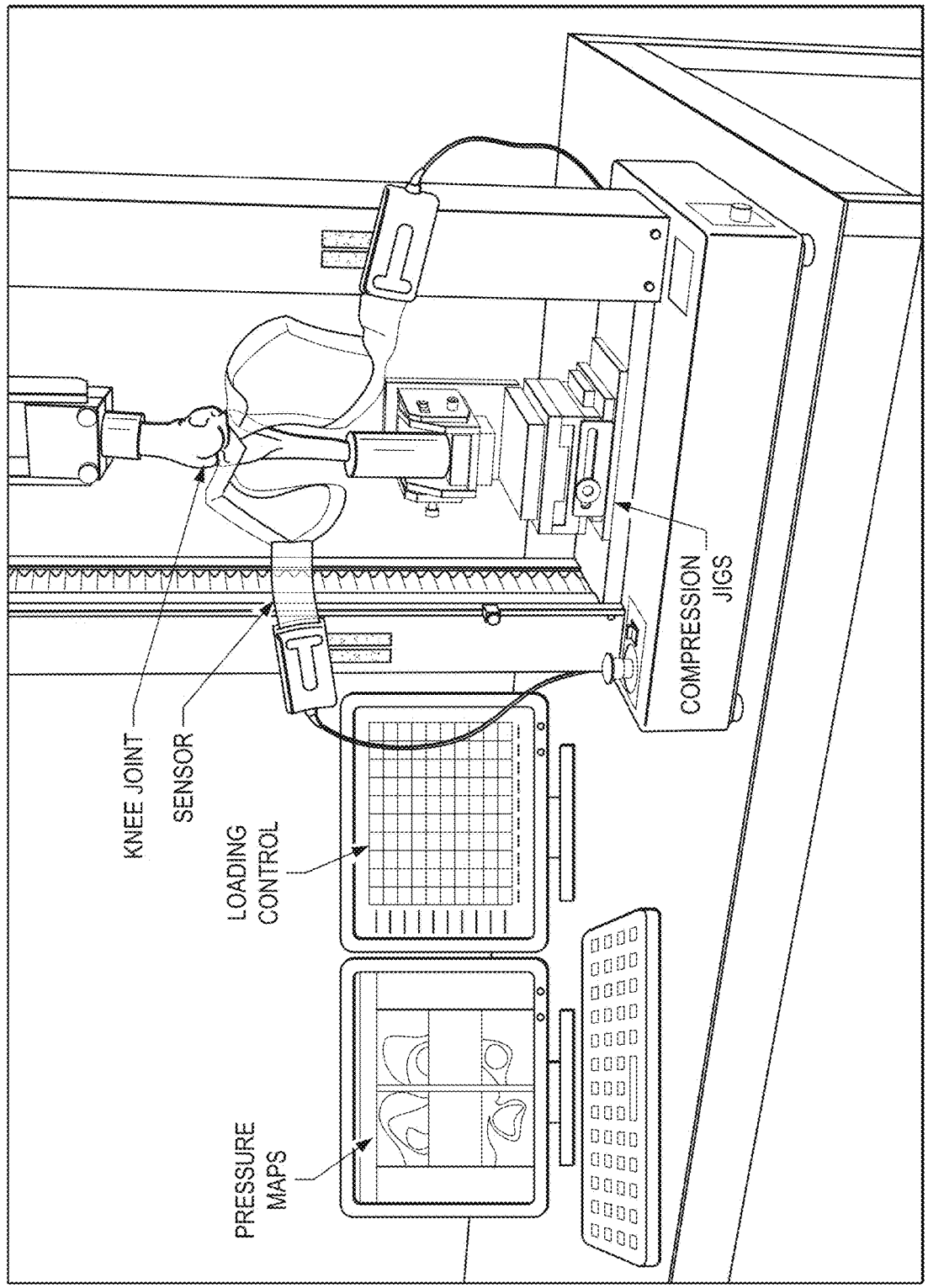
FIG. 21 is a perspective view of a system for monitoring loads across a knee joint according to one aspect of the present disclosure.

In some instances, the contact pressures are compared to accepted values for a healthy natural meniscus based on one or more large scale studies. In some large scale studies the contact pressures of intact healthy menisci are measured in human cadaveric knees under load. Referring to FIG. 21, in some instances healthy knees are positioned on a jig for mechanical compression testing. With the cadaver knee positioned within the jig, all degrees of freedom of the knee are fixed to prevent unwanted flexion of the knee during the compression test. Also, in some instances the MCL bone plug is released to allow for the insertion of one or more contact pressure sensors. Generally, any suitable contact pressure sensors are utilized. In some instances, pressure sensors available from Tekscan Inc. are utilized. With the healthy medial meniscus intact, the knee is subjected to a load at a flexion angle of 0°. In some instances, the maximum load is between about 800N and about 2000N. In some instances, the maximum load is approximately 1200N. In some embodiments, the amount of load applied to the knee is controlled through a software interface and may vary from about 0N to about 2000N. In some instances, the amount of load applied is at least partially based on the patient's weight and/or activity level.

Corresponding pressure maps are obtained from the pressure sensors based on the loading of the knee and, in particular, the meniscus. The pressure maps are displayed via a software interface in some embodiments. In some instances, the same software interface (or coordinated software interfaces) is utilized for both controlling the amount of load applied to the knee and displaying the corresponding pressure maps. The pressure maps are stored in an accessible database in some instances. In that regard, the pressure maps may be associated with characteristics of the knee being tested (such as tibial, femoral, and meniscal dimensions and/or other characteristics) and/or patient characteristics (such as weight, activity level, and/or other characteristics) such that the pressure maps and associated data may be retrieved for use in future prosthetic device selection methods.

As discussed in greater detail below, similar loading and pressure monitoring methods are utilized in some embodiments of the present disclosure for trialing prosthetic devices during a surgical procedure in order to identify the best prosthetic device for the patient. In that regard, trial prosthetic devices containing pressure sensors are introduced into the patient's knee and the knee is subjected to a load. The corresponding pressure maps of the trial prosthetic devices are then compared to those of a healthy meniscus (based on a cadaver study or otherwise) and/or accepted values for a healthy meniscus to determine the suitability of the prosthetic device.

Figure 22:
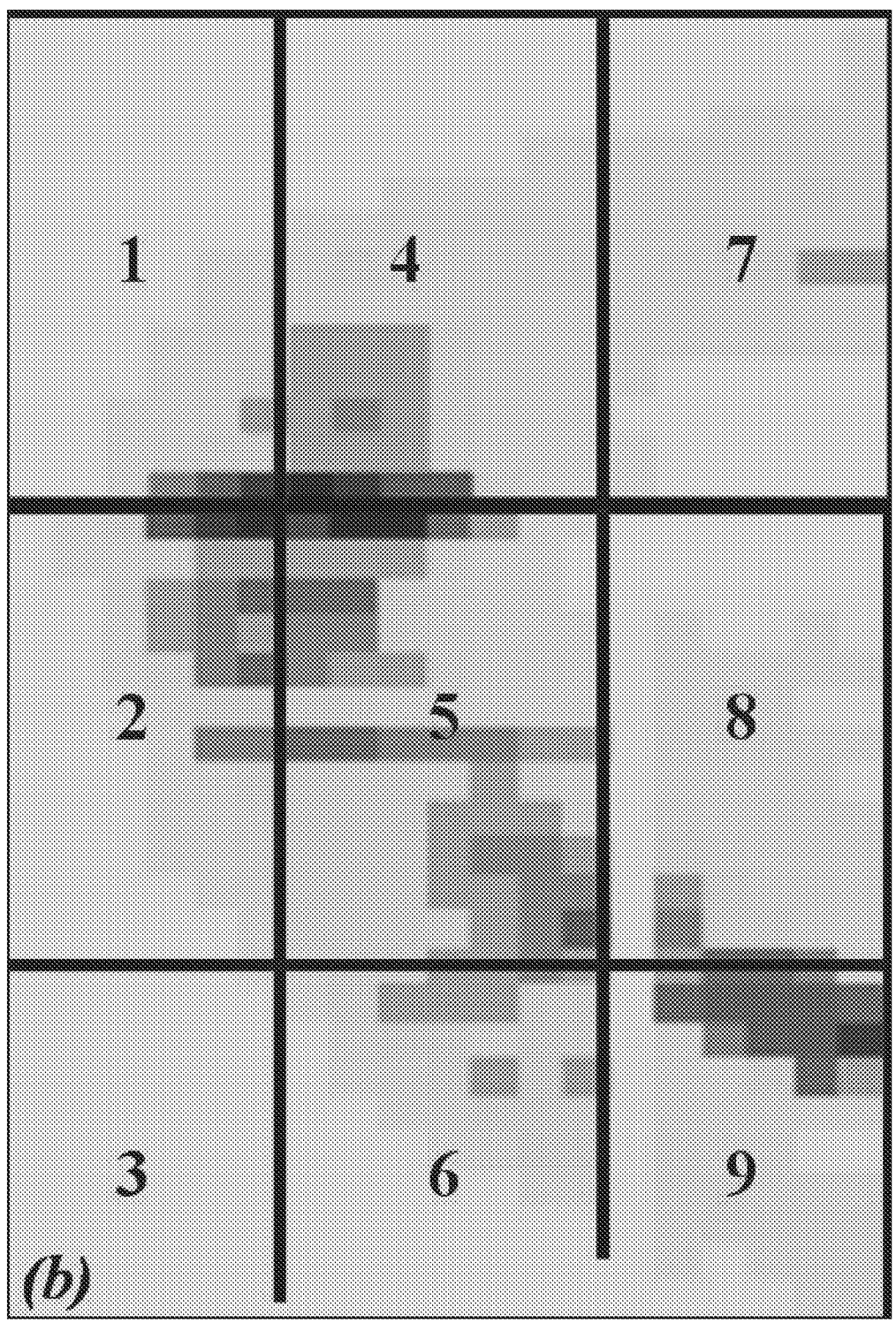
FIG. 22 is a rendering of a contact pressure map of a prosthetic device according to one aspect of the present disclosure.

In that regard, in some instances the pressure distribution maps attained from the trial prosthetic devices are analyzed and compared to the pressure distribution maps attained from one or more cadaveric knees. The pressure distribution maps are analyzed and compared on a regional basis, a global basis, or a combination thereof. In some instances, a comparison of local or regional characteristics is advantageous in identifying small, but possibly critical variations in the pressure maps and/or in emphasizing regions of interest. Furthermore, measurement of the total contact area on a global basis and/or global contact pressures may not reveal potentially problematic discrepancies in the contact areas and pressure points of the prosthetic devices. Quantization of the small regional areas better approximates the specific shape of the contact areas and the maximum pressure points in some instances. Based on the shape of the natural meniscus, the pressure maps are divided into 9 regions in some embodiments. For example, FIG. 22 illustrates one embodiment of a pressure map shown divided into the 9 separate rectangular regions. In other instances, the pressure maps are divided into other numbers of regions and/or regions having shapes other than rectangular. For the purposes of this disclosure the 9 rectangular regions will be utilized with it being understood that other orientations are utilized in some instances and that any comparisons, weightings, equations, or otherwise are modified to correspond with the alternative regional orientations in such instances.

In some instances, the pressure distributions or pressure maps of the trial prosthetic devices are compared to the accepted pressure distributions for a healthy meniscus. In some instances, the prosthetic devices are scored based on how well each device's pressure map compares to the accepted pressure distributions. In one embodiment, 3 different measurements are utilized to evaluate the pressure maps of the prosthetic devices: global contact area, regional contact area, and peak regional pressures. The first measurement is the global contact area or utilization of area determination, where the total contact area of the prosthetic device under load is compared to the established value for total contact area of a healthy meniscus. In some instances, this determination is based on a binary function where the prosthetic device is given a full score (e.g. 1) if the total contact area is within a certain percentage of the accepted value. In that regard, in some instances the acceptable percentage variation is between about ±30%. In some instances, the acceptable percentage variation is between about ±20%. In other instances, the acceptable percentage variation is between about ±10%. In some instances, the acceptable percentage variation is selected by the treating medical personnel. A binary equation is utilized to quantify this determination in some instances. For example, the following binary equation is based on a ±30% acceptable percentage variation:

$$Bin\{x\} = \begin{cases} 1, \text{ if } 0.7 < x < 1.3 \\ 0, \text{ otherwise} \end{cases}.$$

Similar, binary equations are utilized for other percentage variations. For example, a ±15% acceptable percentage variation is represented by the following binary equation in some instances:

$$Bin\{x\} = \begin{cases} 1, \text{ if } 0.85 < x < 1.15 \\ 0, \text{ otherwise} \end{cases}.$$

Based on the binary equation corresponding to the acceptable percentage variation of the contact areas a utilization of area score or global contact score is determined. In some instances, the utilization of area is weighted to be a certain percentage of the overall score of the prosthetic device. For example, in some instances the utilization of area is weighted to be between 0% and 50% of the prosthetic devices overall score. In one particular embodiment, the following equation represents the utilization of area ("UoA") score: UoA=6.6·Bin{AoC(I)/AoC(M)}, where AoC represents the total contact area for the implant (I) and natural meniscus (M). Similar equations are utilized for other weightings by changing the value of the number multiplied by the binary function to give effect to the desired percentage of the overall score.

Generally, the regional contact area parameter is determined, scored, and weighted in a manner similar to that of the global contact area discussed above. For example, in some instances a contact area (CA) score is determined by the following equation:

$$CA = \sum_{n=1}^{9} w_n \cdot Bin\left\{\frac{A_n^I}{A_n^M}\right\},$$

where $A_n^I$ and $A_n^M$ represent the contact areas for the implant and natural meniscus, respectively, and $w_n$ represents the weight factor of each region n. In one particular embodiment, the weight factors for the regions 1-9 as illustrated in FIG. 22 are as set forth in the following Table 7:

TABLE 7

Exemplary Contact Area Weight Function Values

| | region | | | | | | | | |
|---|---|---|---|---|---|---|---|---|---|
| | 1 | 2 | 3 | 4 | 5 | 6 | 7 | 8 | 9 |
| $q_n$ | 0.66 | 0.99 | 0.66 | 0.99 | 0.66 | 0.99 | 0.33 | 0.33 | 0.99 |

Peak contact pressure for each of the regions is also considered in some embodiments. In some instances, the peak contact pressure for each region is compared to the accepted peak contact pressure for a healthy meniscus. In other instances, the ratio of the peak contact pressure to the average contact pressure for each region is compared to the accepted ratio of peak contact pressure to average contact pressure. For example, in one embodiment, the peak contact pressure score (PCP) is determined by the following equation:

$$PCP = \sum_{n=1}^{9} q_n \cdot Bin\left\{\frac{PP_n^I / PA_n^I}{PP_n^M / PA_n^M}\right\},$$

where $PP_n^I$ and $PP_n^M$ represent the peak contact pressure in region n for the implant and healthy natural meniscus, respectively, where $PA_n^I$ and $PA_n^M$ represent the average contact pressure in region n for the implant and natural meniscus respectively, and where $PP_n^M$ represents the weight factor of region n. In one particular embodiment, the weight factors for the regions 1-9 as illustrated in FIG. 22 are as set forth in the following Table 8:

TABLE 8

Exemplary Peak Contact Pressure Weight Function Values

| | region | | | | | | | | |
|---|---|---|---|---|---|---|---|---|---|
| | 1 | 2 | 3 | 4 | 5 | 6 | 7 | 8 | 9 |
| $q_n$ | 0.68 | 1.02 | 1.02 | 0.68 | 0.68 | 1.02 | 0.34 | 0.34 | 1.02 |

In some instances, the score of the prosthetic device is determined by adding the scores for the utilization of area, contact area, and peak contact pressure together. In some instances, one or more additional parameters are taken into consideration in scoring the prosthetic devices. For example, in some instances a binary implant movement or dislocation score (IM) is utilized. In that regard, if unwanted movement or dislocation of the prosthetic device occurs during trialing of the prosthetic device, then the prosthetic device is given a score of zero. However, if no unwanted movement or dislocation occurs, then the prosthetic device is given a score of one. In some instances, a binary implant impingement score (CP) is utilized. In that regard, if the prosthetic device impinges on any cruciate ligaments or other surrounding anatomy that will be detrimental to the performance of the prosthetic device, then the prosthetic device is given a score of zero. However, if no such impingement occurs, then the prosthetic device is given a score of one. In some instances, the score of the prosthetic device takes into account both the implant movement or dislocation score (IM) and the implant impingement score (CP). In one particular example, the following equation represents the total score of the prosthetic device taken these additional parameters into account:

$$SCORE = (UoA + CA + PCP) \cdot IM \cdot CP.$$

Figure 23:
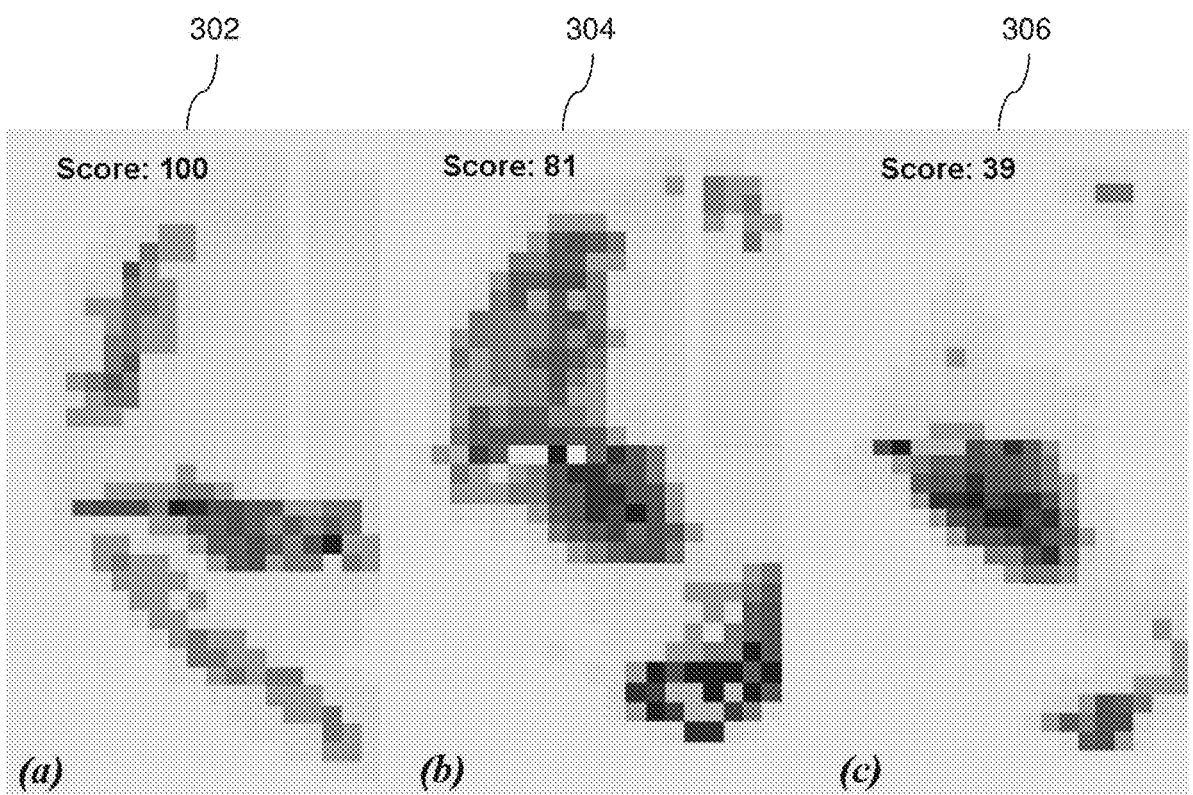
FIG. 23 is a rendering of a plurality of contact pressure maps of various prosthetic devices according to one aspect of the present disclosure.

Referring now to FIG. 23, shown therein is are three pressure maps 302, 304, and 306 corresponding to a healthy natural meniscus, a best matched prosthetic device based on the healthy natural meniscus, and a less suitable or unsuitable prosthetic device based on the healthy natural meniscus, respectively. As noted on the pressure map 302, the healthy natural meniscus has a score of 100 or a perfect score. This is because replicating the healthy natural meniscus is the goal of the prosthetic devices. In some instances, the pressure map 302 or goal is based on an accepted pressure distribution that is derived from one or more healthy natural menisci. As shown, the prosthetic device of pressure map 304 has a score of 81, whereas the prosthetic device of pressure map 306 has a score of 39. While generally the highest score possible is preferred, in some instances a threshold score (e.g., 70 points on a 100 point scale) is utilized to determine whether a particular prosthetic device is suitable for a patient. If the prosthetic device meets or exceeds the threshold score, then it is further considered. In that regard, where multiple prosthetic devices meet or exceed the threshold score, each of the suitable prosthetic devices are trialed or otherwise tested in some instances to identify the most suitable device for the patient.

Referring again to FIG. 2, in some instances the simulated loading of the prosthetic devices at step 234 and the corresponding evaluation of the resultant pressure maps at step 236 are scored using the same or substantially similar parameters as those discussed above. In other instances, other parameters and/or scores are utilized. Generally, by combining the scores for each factor of the loading simulations, an overall score is obtained for each available prosthetic device. In that regard, it is understood that the various factors or measurements are weighted in some embodiments to emphasize the importance of certain aspects of the prosthetic device. The importance or weighting of the various factors are determined by such factors as the patient's age, activity level, weight, and/or other factors considered by the treating medical personnel. In some instances, the weighting function is determined by a computer system based on the answers provided to prompted questions. In other instances, the treating medical personnel manually set the weighting function of the various dimensions.

In some instances, the finite element-based matching process 210 includes motion simulations in addition to or in lieu of the load bearing simulations discussed above. In that regard, the motion of the knee joint is compared to that of natural, healthy meniscus for one or more available prosthetic devices. In some instances, these simulations are designed to simulate typical patient movements such as walking, running, riding a bicycle, standing up, sitting down, etc. The prosthetic devices are then provided subgrades based on their performance for various factors related to knee movement (e.g., position and/or loading support at various degrees of flexion). In some embodiments, the loading simulations and motion simulations are combined such that the devices are scored base on loading functions during the motion simulations.

In some instances, the finite element-based matching process is compared to a generic model rather than a patient specific model. For example, in some embodiments a plurality of finite element models are provided corresponding to variety of different knee sizes and/or knee types. A specific finite element model from the plurality of different finite element models is selected for the current patient. In some embodiments, the specific finite element model is based at least partially on the knee size of the current patient. In one instance, the selected model is determined based on MRI data of the patient. Further, in some instances the selection of the specific finite element model is at least partially based on correlation parameters—such as those discussed above with respect to the correlation-based matching process 208—for the candidate knee. In some instances, each of the available prosthetic devices is tested or simulated with respect to each of the finite element models and the functionality of each of the prosthetic devices is compared to the accepted values for a natural, healthy meniscus. Accordingly, for each of the finite models one or more suitable prosthetic devices are identified. Thus, using only the associated bone measurements from the CT and/or MRI scans of a candidate knee, a best-matched finite element model is identified and, from the best-matched finite element model, the corresponding suitable prosthetic devices are identified as suitable devices for the current patient. Based on the evaluation at step 236, one or more best-fitted prosthetic devices are identified at step 238.

In some embodiments, the pre-implantation matching method 202 continues at step 240 by weighting the answers provided by the direct geometrical matching process 206, the correlation parameters-based matching process 208, and the finite element-based matching process 210. In some embodiments, each of the matching processes 206, 208, and 210 are given equal weight. However, in other embodiments the matching processes 206, 208, and 210 are given unequal weights. For example, where a generic finite element model has been utilized—rather than a patient-specific generated finite element model—the finite element model-based correlation may be given less weight than the direct geometrical matching process 206 and the correlation parameters-based matching process 208. The determination of the weighting of the different matching processes 206, 208, and 210 is determined by the treating medical personnel in some instances.

Table 9 below illustrates one possible scoring breakdown according to the present disclosure.

TABLE 9

| | Exemplary Scoring Breakdown | | | | | | | | | | | | | |
|---|---|---|---|---|---|---|---|---|---|---|---|---|---|---|
| | Injured knee measurements (2.3.1.) | | | | | | Intact knee measurements (2.3.2.) | | | | | 3D comparisons (2.3.3.) | | |
| Side | Candidate knee | | | | | | Healthy knee or Accepted Value | | | | | Healthy knee or Accepted Value | | |
| Method | MRI measurements | | | | | | MRI measurements | | | | | Solid modeling* | | |
| Measure | TPW | MW | ML | TMA | FW | FL | MMWA | MMWP | MML | HA | HP | HC | Volume | Shell | Interference | Visual |
| Score | 6 points | | | | | | 6 points | | | | | 4 points | | |
| Total | | | | | | | 16 points | | | | | | | |

As shown, the scoring includes three categories: injured knee measurements, intact knee measurements, and 3D comparisons. In the present embodiment, the injured and intact knee measurements each account for 6 points and the 3D comparisons account for 4 points, for a total possible score of 16 points for any prosthetic device. In that regard, for the injured knee measurements the prosthetic device is scored on a scale from 0 to 1.0 for each of 6 different parameters. In the present embodiment, at least six measurements of the injured knee are taken, namely TPW, MW, ML, TMA, FW, and FL, each of which is discussed above. Based on these measurements, each prosthetic device is scored for each of the six different parameters. In the present embodiment, the six parameters are MMW/TPW, MMW/MW, MML/ML, MMA/TMA, MMW/FW, and MML/FL, where the numerator is a value of the prosthetic device and the denominator is the measured value of the injured knee. In other embodiments, other combinations of measurements and/or scoring parameters, including additional or fewer measurements and/or scoring parameters, are utilized. In some instances, the scoring for each parameter is binary. That is, the prosthetic device is either suitable for the particular parameter (in which case it receives a score of 1) or not suitable (in which case it receives a score of 0). In some instances, the determination of whether a prosthetic device is suitable for a particular parameter is determined by whether the device is within an accepted range for the parameter. In some instances, the accepted range is defined by a standard deviation around an established value for the parameter. The scores for each of the six parameters are added together to arrive at the injured knee measurement sub-score.

For the intact or healthy knee measurements the prosthetic device is scored on a scale from 0 to 1.0 for each of 6 different measurements. In the present embodiment, the six measurements are MMWA, MMWP, MML, HA, HP, and HC, each of which is discussed above. In other embodiments, other combinations of measurements, including additional or fewer measurements, are utilized. The measurements of the prosthetic device are directly compared to these measurements of the healthy knee and the prosthetic device is scored accordingly. In that regard, for each of the measurements the prosthetic device is scored on a scale from 0 to 1.0. In some instances, the scoring for each measurement or parameter is binary. That is, the prosthetic device is either suitable for the particular measurement (in which case it receives a score of 1) or not suitable (in which case it receives a score of 0). The scores for each of the six measurements are added together to arrive at the intact knee measurement sub-score.

Finally, for the 3D modeling comparisons each prosthetic device is scored on a scale from 0 to 1.0 for each of 4 different parameters. In the present embodiment, the four parameters are volume, shell, interference, and visual. Generally, a 3D model of both the prosthetic device and the healthy intact meniscus are utilized in the 3D modeling comparisons. However, in some instances no actual 3D models are generated, but the corresponding measurements are utilized for making the comparisons. In that regard, the volume parameter compares the volume of the prosthetic device to the volume of the intact healthy meniscus. The closer the match in the volume the higher the score for the prosthetic device. Similarly, the shell volume compares the outer surface of the prosthetic device to the outer surface of the intact meniscus. The closer the match in the outer surfaces the higher the score for the prosthetic device. The interference parameter looks to the overlap between the prosthetic device and the intact meniscus. That is, the interference parameter looks to identify how well the prosthetic device matches up the volume defined by the intact meniscus. The closer the prosthetic device matches the healthy meniscus, the higher the score. Finally, in some instances a visual comparison of the prosthetic device to the healthy or intact meniscus is performed. In that regard, treating medical personnel makes an educated determination of how well the prosthetic device matches the meniscus. In some embodiments, other combinations of measurements and/or parameters, including additional or fewer measurements and/or parameters, are utilized. For example, in some embodiments, the subjective or qualitative visual comparison is not performed and/or not included in the scoring of the prosthetic device. For each of the comparisons, the prosthetic device is scored on a scale from 0 to 1.0. In some instances, the scoring for each comparison or parameter is binary. That is, the prosthetic device is either suitable for the particular parameter (in which case it receives a score of 1) or not suitable (in which case it receives a score of 0). The scores for each of the comparisons are added together to arrive at the 3D comparison sub-score.

With each of the injured knee sub-score, the intact knee sub-score, and the 3D comparison sub-score calculated, a total score for each prosthetic device is determined by adding the sub-scores together. Generally, the prosthetic device with the highest total score will be identified as the best suited prosthetic device. However, as discussed above, in some instances more than one prosthetic device is identified as being suitable (e.g., meeting a threshold score), in which case additional scoring or trialing of the suitable prosthetic devices is utilized to select the best suited prosthetic device.

Finally, the pre-implantation matching method 202 continues at step 242 with the identification of one or more suitable prosthetic devices are identified. In some embodiments, a single "best" prosthetic device is identified by the pre-implantation matching method 202. In other embodiments, two or more suitable prosthetic devices are identified. In that regard, where two or more suitable prosthetic devices are identified a specific prosthetic device is selected by the during-implantation matching process 204.

Figure 24:
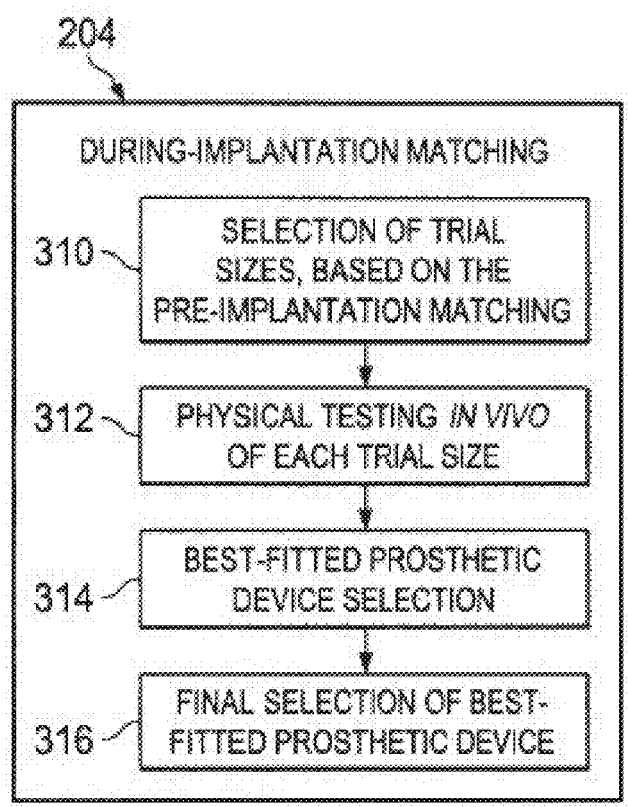
FIG. 24 is a block diagram of an embodiment of a method according to one aspect of the present disclosure for selecting an appropriate prosthetic device for use with a patient's knee during surgery.

Referring now to FIGS. 1 and 24, after the pre-implantation matching process at step 202, the method 200 continues at step 204 with a during-implantation matching process. The during-implantation matching process 204 begins at step 310 with the selection of at least two suitable trial prosthetic devices. In some embodiments, the suitable trial prosthetic devices are identified by the pre-implantation matching process 202 described above. In some embodiments, three trial prosthetic devices are selected. Further, in one particular embodiment three different sizes of a prosthetic device are selected. In other embodiments, the selected prosthetic devices may be substantially different in shape, materials, function, and/or other properties. In some embodiments, the trial prosthetic devices are substantially similar to the prosthetic devices that are to be permanently implanted. In some embodiments, the trial implants are the actual prosthetic devices that are to be permanently implanted. In one embodiment, each trial has a similar external geometry to the final implant and is formed of a material having similar strength properties to the final implant. However, the trial lacks the reinforcing fibers or layer. Thus, the trial may be more easily removed from the knee joint than the final implant. Further, in some instances, the trial includes a visual indicator such as a marking (e.g., "TRIAL") on the exterior or a dye in the polymer resin to readily distinguish the trial from the final implant. In some instances, the trials include radiopaque markers imbedded therein to distinguish them from the final implant.

The during-implantation matching process 204 continues at step 312 with an in vivo physical testing of the prosthetic device. Generally, the in vivo testing comprises introducing the trial prosthetic device into the knee joint and moving the knee joint through a series of movements. At step 314, the surgeon considers the fit of each prosthetic device trial and the corresponding movement of the knee joint. Based on the surgeon's observations at step 314, the during-implantation matching process 204 concludes at step 316 with the final selection of the best prosthetic device for the patient. Subsequently, the surgeon implants the selected prosthetic device into the patient. In some instances, the prosthetic device is implanted according to methods described herein.

Utilizing the during-implantation matching process 204, the surgeon can decide, based on actual physical tests, which prosthetic device best fits a candidate knee. In that regard, in some embodiments the pre-implantation matching process is utilized to identify two or more prosthetic devices that are suitable for use in the candidate knee. The during-implantation matching process is then utilized to select the best of the suitable prosthetic devices. Accordingly, the during-implantation matching process 204 may be utilized to confirm the results of the pre-implantation matching process 202 in some instances. In some embodiments, trial implants are utilized in the during-implantation matching process for selecting the appropriate sized prosthetic device and then the actual prosthetic device of that size is subsequently implanted. In some embodiments, three sizes of prosthetic devices and/or trials are taken to surgery. Typically, the three sizes will be the best fit prosthetic device identified in the pre-implantation matching process, and prosthetic devices slightly larger and slightly smaller than the best fit device. According to the fit within the actual candidate knee the surgeon identifies the best prosthetic device to use. After identifying the best fit prosthetic device during surgery, the surgeon implants the surgical device.

Figure 25:
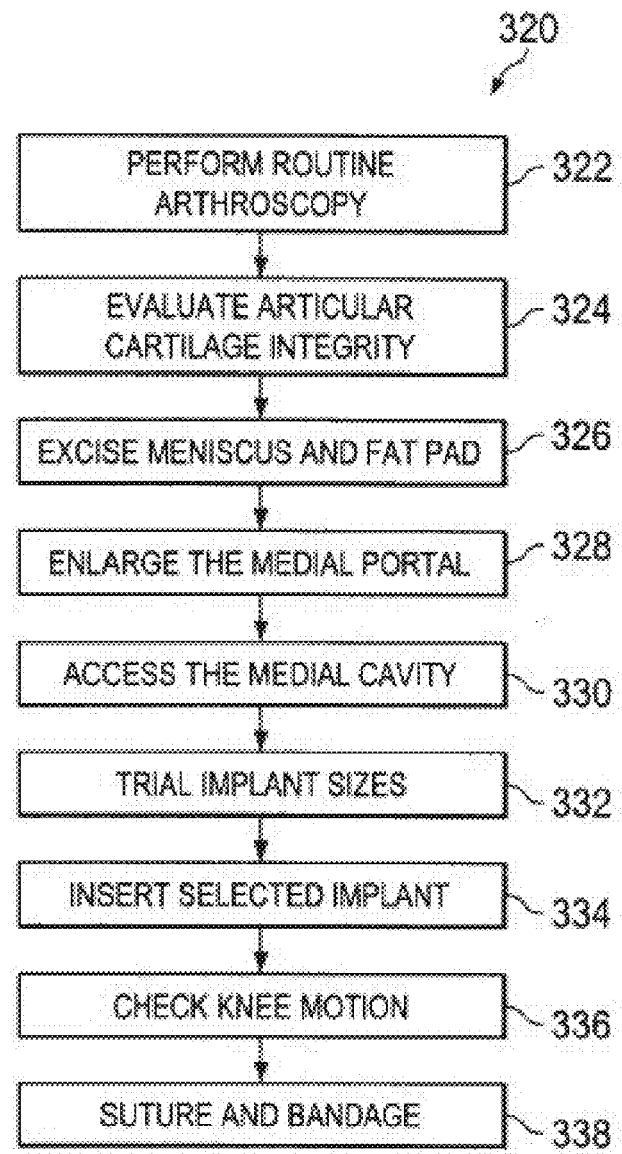
FIG. 25 is a block diagram of a surgical protocol according to one aspect of the present disclosure.

Referring now to FIG. 25, shown therein is a block diagram of a surgical protocol 320 according to one aspect of the present disclosure. Generally, the surgical protocol 320 relates to the implantation of a prosthetic device into the knee joint of a patient. In the specifically described embodiments, the surgical protocol 320 relates to the implantation of a surgical device for replacing a medial meniscus. In other embodiments, similar surgical protocols are utilized for replacing a lateral meniscus with a surgical device. In some instances, the surgical procedure replaces both the medial and lateral menisci with prosthetic devices.

The surgical protocol 320 begins at step 322 where an arthroscopy is performed. In some embodiments, a leg holder or post is utilized. In such embodiments, the leg holder or post may be utilized in subsequent steps to facilitate application of a valgus force, ease insertion of implant, and/or otherwise assist in the performance of the surgery. The arthroscopy is a routine arthroscopy in some embodiments. The surgical protocol 320 also addresses any additional inter-articular pathologies as needed at step 322.

The surgical protocol 320 continues at step 324 with an evaluation of the articular cartilage of the knee joint. In some embodiments, the integrity of the articular cartilage positioned within the medial compartment is evaluated. Generally, the evaluation of the articular cartilage is to confirm that the patient's knee is suitable for receiving the prosthetic device intended to be implanted. In some instances, the articular cartilage is evaluated to identify defects in the articular cartilage such that these defects may be treated or otherwise addressed prior to implantation of the prosthetic device.

The surgical protocol 320 continues at step 326 where the meniscus and the fat pad are excised. In that regard, in some embodiments the meniscus is entirely removed (total meniscectomy). In other embodiments, the meniscus is partially removed (partial meniscectomy) to allow for the introduction of the prosthetic device into the knee joint. Generally, the fat pad is excised only to the degree necessary for exposure or access to the meniscus and/or medial compartment of the knee joint. Accordingly, in some instances the fat pad remains substantially intact. In other embodiments, a substantial portion of the fat pad may be removed.

The surgical protocol 320 continues at step 328 with an enlarging of the medial portal. Generally, the medial portal is the same portal created by the arthroscopy of step 322. However, in some embodiments the medial portal is separate from the portal created by the arthroscopy. In some embodiments, the incision is adjacent to the medial border of the patellar tendon. The medial portal is enlarged to accommodate the insertion of the prosthetic device or implant into the knee joint. In some embodiments, the incision or portal is enlarged to a size between approximately 4.0 cm and approximately 6.0 cm. However, depending on the size of the implant, the flexibility of the implant, and/or other factors, the size of the opening may be larger or smaller in other instances.

The surgical protocol 320 continues at step 330 with accessing the medial cavity of the knee joint. In some instances, accessing the medial cavity comprises opening the capsule and retinaculum to provide access to the medial cavity. Further, in some instances any remaining portions of the anterior meniscus rim are removed or excised when gaining access to the medial cavity.

After gaining access to the medial cavity, the surgical protocol 320 continues at step 332 with the insertion of one or more trial implants into the knee joint. The trial implants may represent different sizes of the same implant, different types of implants, and/or combinations thereof. In some embodiments, the trial implants are identified in a pre-implantation matching or selection method. In one particular instance, the pre-implantation matching process 202 discussed above is utilized to identify one or more suitable implants for which trial versions of the implant may be obtained. In some instances, the trial implants are substantially similar in size and shape to the actual implant that will be permanently implanted in the patient. In some instances, the only difference between the trial implant and the actual implant is the material from which the implant is made. Specifically, in one embodiment, the trial does not include reinforcing fibers. In some instances, the trial implant and the actual implant are identical copies of one another. In some instances, a single implant is used as both the trial and actual implant.

Generally, a first trial implant is inserted into the knee joint. In some instances, the first trial implant is representative of the implant identified as the most suitable implant in a pre-implantation selection process. After insertion of the trial implant into the knee joint, the functionality of the knee joint is checked. In that regard, the surgeon or other medical personnel moves the knee through a variety of motions similar to the natural motions of the knee and monitors the knee for signs of problems. For example, in some instances the knee is monitored for limited or excessive ranges of motion, abnormal sounds (e.g., clicking or grinding), non-smooth movements, implant rotation, implant translation, and/or other issues indicating a potential problem with using the associated implant. If a problem or potential problem is observed when checking the functionality of the knee, the first trial implant is removed, an alternative trial implant is inserted, and knee functionality is checked. In some instances, the subsequent trial implant will be one size up or down from the previous trial implant. Further, the time period for the trialing of the implant can range from a couple of minutes up to several weeks. This process repeats until a suitable trial implant is identified. In some instances, the trial implant process is substantially similar to the during-implantation matching process 204 discussed above. In some instances, the knee joint with the trial implant positioned therein is subjected to a load simulating a loading of the knee joint. For example, the loading simulates the load associated with standing, walking, jogging, bicycling, and/or otherwise. Exemplary methods of such loading are discussed in greater detail below. Generally, the simulated loading is utilized to identify the most suitable implant.

Figure 26:
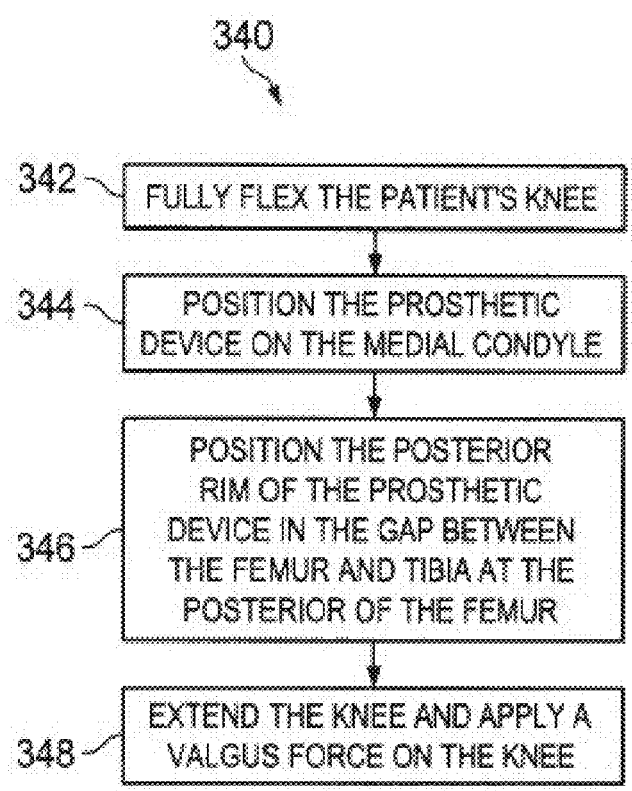
FIG. 26 is a block diagram of a method for implanting a prosthetic device into a patient's knee for use in the surgical protocol of FIG. 25 according to one aspect of the present disclosure.

After a suitable trial implant has been identified, the surgical protocol 320 continues at step 334 with the implantation of the implant or prosthetic device selected during the trialing process. Generally, the prosthetic device is implanted using any suitable implantation method for the associated prosthetic device. A couple of implantation methods will now be described. In some instances, the prosthetic devices of the present disclosure are suitable for implantation using the following methods. Referring to FIG. 26, shown therein is a block diagram of a method 340 of implanting a prosthetic device into a patient's knee according to one aspect of the present disclosure. In some instances, the method 340 is utilized as the implantation step 334 of the surgical protocol 320. The method 340 will be described with respect to a "floating" implant, i.e., an implant that does not penetrate the bone or mate with a device that penetrates bone. However, in other instances a similar method may be utilized with an implant that is fixedly secured to bone by penetrating bone or mating with a device that penetrates the bone.

The method 340 begins at step 342 where the patient's knee is fully flexed. That is, the patient's knee is put in full flexion. After the patient's knee has been fully flexed, the method 340 continues at step 344 where the prosthetic device is positioned onto the medial compartment of the tibia. In one embodiment a bridge of the prosthetic device is folded slightly inward into a reduced size insertion configuration as it is passed into the knee joint. Once the bridge of the prosthetic device reaches the femoral notch, the bridge resiliently moves to its anchoring configuration. The method 340 continues at step 346 where the posterior rim or edge of the prosthetic device is positioned within the gap between the femur and the tibia adjacent the posterior portion of the femur. With the prosthetic device positioned on the medial compartment and the posterior rim in the gap between the femur and tibia, the method 340 continues at step 348 where the knee is extended and a valgus force is applied to the knee. In some instances, the knee is extended to about a 30 degree flexion. In other instances, the knee is extended less or more. This secures the implant within the knee joint and engages the implant with both the medial compartment of the tibia and the femur. Subsequently, the shape of the implant and the compression forces applied across the implant keep the implant in place within the knee. In some instances, prosthetic devices as described in the present disclosure and/or prosthetic devices as described in U.S. patent application Ser. No. 10/497,897 filed Dec. 3, 2002 and titled "Cushion Bearing Implants for Load Bearing Applications", U.S. patent application Ser. No. 11/868,254 filed Oct. 5, 2007 and titled "Meniscus Prosthetic Device", U.S. patent application Ser. No. 12/100,059 filed Apr. 9, 2008 and titled "Tensioned Meniscus Prosthetic Devices and Associated Methods", and/or U.S. patent application Ser. No. 12/100,069 filed Apr. 9, 2008 and titled "Meniscus Prosthetic Devices with Anti-Migration Features", each of which is hereby incorporated by reference in its entirety, are implanted using the method 340.

Figure 27:
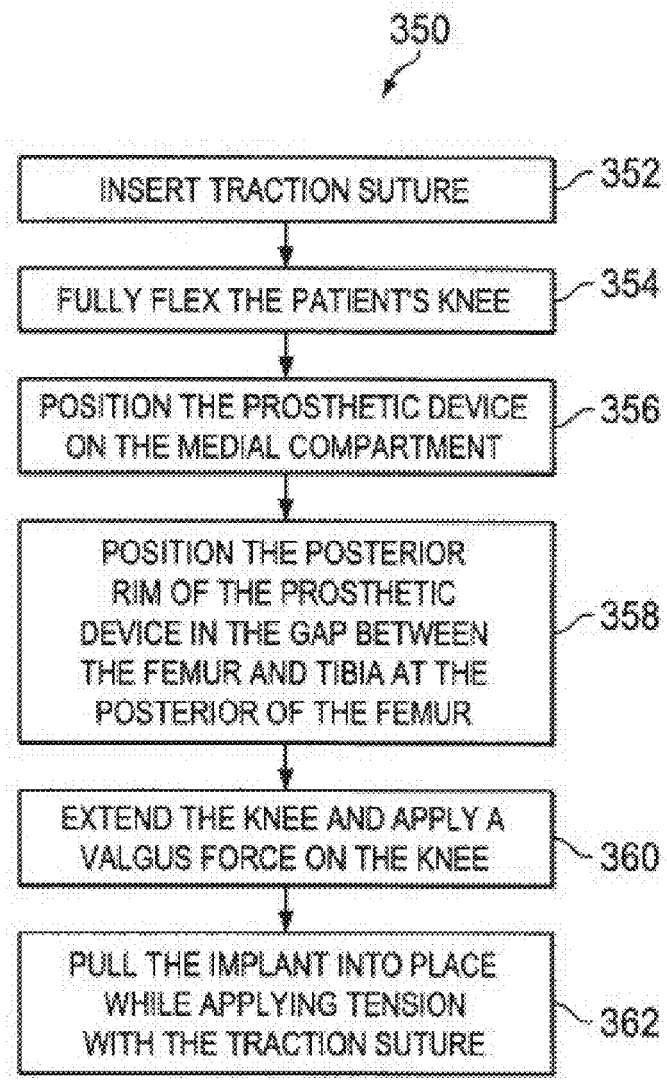
FIG. 27 is a block diagram of a method for implanting a prosthetic device into a patient's knee for use in the surgical protocol of FIG. 25 according to another aspect of the present disclosure.

Referring now to FIG. 27, shown therein is a block diagram of a method 350 of implanting a prosthetic device into a patient's knee according to one aspect of the present disclosure. In some instances, the method 350 is utilized as the implantation step 334 of the surgical protocol 320. The method 350 will be described with respect to a "floating" implant, i.e., an implant that does not penetrate the bone or mate with a device that penetrates bone. However, in other instances a similar method may be utilized with an implant that is fixedly secured to bone by penetrating bone or mating with a device that penetrates the bone.

The method 350 begins at step 352 where a traction suture is inserted. In some instances the traction suture is inserted to the posterior-medial side of where the prosthetic device will be positioned and extends through the posterior-medial soft tissue structures enveloping the knee. In other embodiments, the traction suture is otherwise positioned adjacent and/or within the knee joint to assist in insertion of the prosthetic device into the medial cavity. It should be noted that in some instances the traction suture is inserted after a partial insertion of the prosthetic device into the knee joint. The method 350 continues at step 354 where the patient's knee is fully flexed. That is, the patient's knee is put in full flexion. After the patient's knee has been fully flexed, the method 350 continues at step 356 where the prosthetic device is positioned onto the medial condyle of the tibia. The method 350 continues at step 358 where the posterior rim or edge of the prosthetic device is positioned within the gap between the femur and the tibia adjacent the posterior portion of the femur. With the prosthetic device positioned on the medial condyle and the posterior rim in the gap between the femur and tibia, the method 350 continues at step 360 where the knee is extended and a valgus force is applied to the knee. The method 350 continues at step 362 where the implant is pulled into its final position while applying tension with the traction suture. In some instances, the traction suture helps facilitate positioning of the implant. In some embodiments, the traction suture is utilized to urge the implant into the medial cavity. In other embodiments, the traction suture is utilized to maintain an opening to the medial cavity to allow the implant to be inserted therethrough. With the prosthetic device secured within the knee joint, the shape of the implant and the compression forces applied across the implant during loading of the knee prevent the implant from slipping out of place.

Referring again to FIG. 25, the method 320 continues at step 336 with checking the knee motion with the prosthetic device implanted. In some embodiments, step 336 is substantially similar to step 332 where the trial implants are evaluated. Accordingly, in some embodiments step 336 comprises confirming the actual implant performs as suggested by the monitoring of the trial implant at step 332. If, for some reason, the knee functionality with the prosthetic device implanted is impaired, the prosthetic device may be adjusted, replaced with an alternative prosthetic device, or otherwise modified to correct the problem. After the knee motion has been checked and confirmed to be acceptable, the method 320 concludes at step 338 with the suturing and bandaging of the knee.

Though not described in the above methods, in some instances, the femoral condyle and/or other aspects of the knee joint are surgically prepared to permit near-normal knee joint flexion after implantation. Further, the tibial plateau and/or other aspects of the knee joint are surgically prepared to fixedly engage the implanted prosthetic device in some instances. Other modifications of the above methods will be apparent to those skilled in the art without departing from the scope of the present disclosure.

Referring now to FIGS. 28-34, shown therein are embodiments of prosthetic devices for monitoring a load or pressure on the knee joint. In some instances, the prosthetic devices of FIGS. 28-34 are trial prosthetic devices utilized to evaluate a perspective prosthetic device for a particular patient. In that regard, in some instances a trial prosthetic device is positioned within a knee joint of the patient and subjected to a load. The resultant peak and/or average pressures across the trial prosthetic device and/or the pressure distribution across the trial prosthetic device are compared to medically accepted values in order to evaluate the suitability of the trial prosthetic device for the patient's knee.

Figure 28:
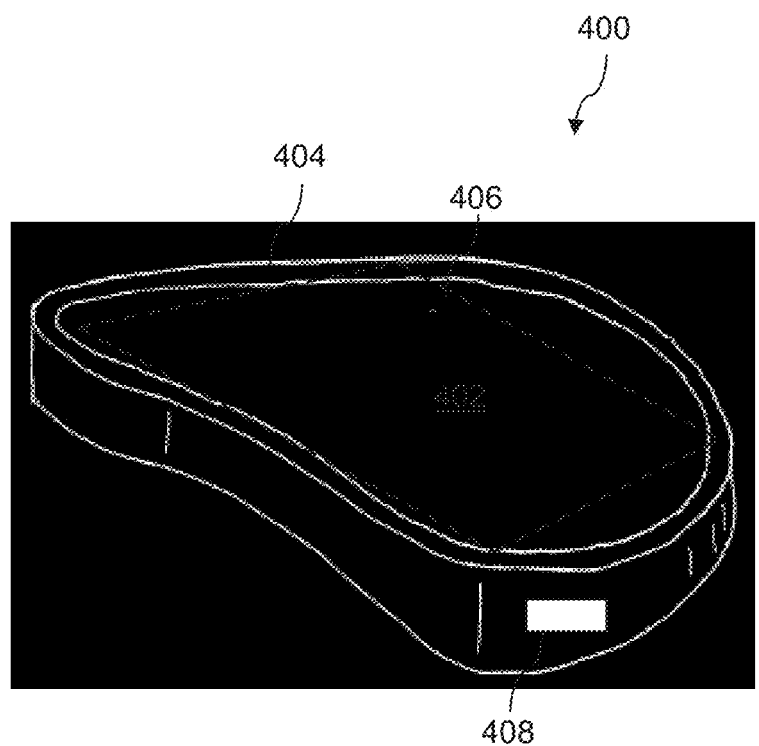
FIG. 28 is a diagrammatic perspective view of a prosthetic device according to one aspect of the present disclosure.

Referring more particularly to FIG. 28, shown therein is a prosthetic device 400 according to one embodiment of the present disclosure. In that regard, the prosthetic device 400 is a meniscus replacement device that comprises an upper surface 402 for engaging a portion of a femur, an opposing lower surface (not shown) for engaging a portion of a tibia, and an outer rim 404 extending between the upper and lower surfaces. The prosthetic device 400 also includes a load sensor or pressure sensor 406. In some instances, the pressure sensor 406 is a single sensor. In other instances, the pressure sensor 406 is a plurality of sensors spaced throughout the device 400. Generally, the pressure sensor(s) 406 are configured to measure the pressures across the prosthetic device 400, from which peak and/or average pressures can be calculated and/or the pressure distribution across the trial prosthetic device can be mapped. In some instances, the pressure sensor(s) 406 are pressure sensors available from Tekscan, Inc. located at 307 West First Street, South Boston, Mass. 02127-1309, USA. In that regard, in some instances the sensor(s) 406 are imbedded into the prosthetic device 400. In some embodiments, the sensor(s) 406 substantially comprise the upper and/or lower surface of the prosthetic device 400. In some embodiments, the sensor(s) are positioned within the body of the prosthetic device 400 and spaced from the upper and lower surfaces.

The thickness of the sensor(s) 406 is taken into consideration in forming the prosthetic device 400 in some instances. In that regard, in some instances the prosthetic device 400 is a trial prosthetic device representative of a permanent or long-term prosthetic device that may or may not include sensors. Accordingly, in some instances the prosthetic device 400 is sized to substantially match the geometries of the long-term prosthetic device. Thus, in some instances the thickness of the sensor(s) 406 is accounted for in forming the prosthetic device 400 to substantially match the long-term prosthetic device. In that regard, in some embodiments the sensor(s) 406 comprise a sensor film or sheet having a thickness less than about 0.5 mm and, in some instances, less than about 0.1 mm. In some instances, the sensor(s) are sufficiently thin that they do not materially affect the geometries of the implant. Accordingly, in some instances the prosthetic device 400 is formed by adding the sensor(s) 406 to the corresponding long-term prosthetic device. For example, in some instances the sensor(s) 406 are secured to at least one of the outer surfaces of the long-term prosthetic. In other instances, the prosthetic device 400 is formed in substantially the same manner as the long-term prosthetic device, but incorporates the sensor(s) 406.

As shown in FIG. 28, the prosthetic device 400 also includes a communication link 408. Generally, the communication link 408 is any suitable for transmitting data collected by the sensor(s) 406 to an external device, such as a computer or other processing system. In that regard, the communication link 408 is in communication with the sensor(s) 406 and/or a storage device or memory associated with the sensor(s) in order to communicate the pressure data obtained by the sensor(s) to an external device for processing and analysis. In some instances, the communication link 408 facilitates a wired connection to the external device. In some instances, the wired connection comprises a USB connection, a firewire connection, a serial connection, a digital connection, an analog connection, and/or other suitable wired connection. In some instances, the communication link 408 facilitates a wireless connection to the external device. In some instances, the wireless connection comprises a bluetooth connection, an 802.11 connection, and/or other suitable wireless connection.

In some instances, the prosthetic device 400 is used as a trial prosthetic device to measure pressures associated with loading of a knee joint with the prosthetic device 400 positioned therein. In this manner, the prosthetic device 400 is utilized to evaluate a corresponding long-term prosthetic device in some instances. In some instances, a plurality of long-term prosthetic devices are available from a library of prosthetic devices for consideration for use in a patient's knee. In some such instances, two or more of the trial versions of the available prosthetic devices including sensors are trialed and subjected to an equivalent and/or known load while positioned within the knee joint. The resultant pressure measurements for each of the prosthetic devices are compared to medically accepted values and/or the values associated with a natural, healthy meniscus in order to evaluate the prosthetic devices with respect to pressure distribution, peak pressure, and/or average pressure data. For example, in some instances the tibialis plateau pressure distributions for each prosthetic device are compared to those of a healthy natural meniscus in terms of contact area size and/or stress concentrations. The prosthetic devices are evaluated or scored based on how well its pressure distribution matches the accepted values associated with a healthy natural meniscus. In one particular embodiment, a prosthetic device is considered acceptable for use if the resultant pressure distribution across the tibialis plateau is within ±15% of a healthy natural meniscus. Further, in some instances the peak pressure measurements of each of the prosthetic devices are compared to the accepted ranges or the peak pressure measurements of the natural, healthy meniscus. The extent to which the prosthetic device is within the accepted range determines the particular device's grade or evaluation for peak pressure. Similarly, in some instances, the peak and average pressure acting on the articular cartilages are compared to the allowed natural values for each prosthetic device and the prosthetic device is evaluated accordingly. In some instances, the accepted values for a healthy natural meniscus are based on one or more large scale studies as discussed above.

Figure 29:
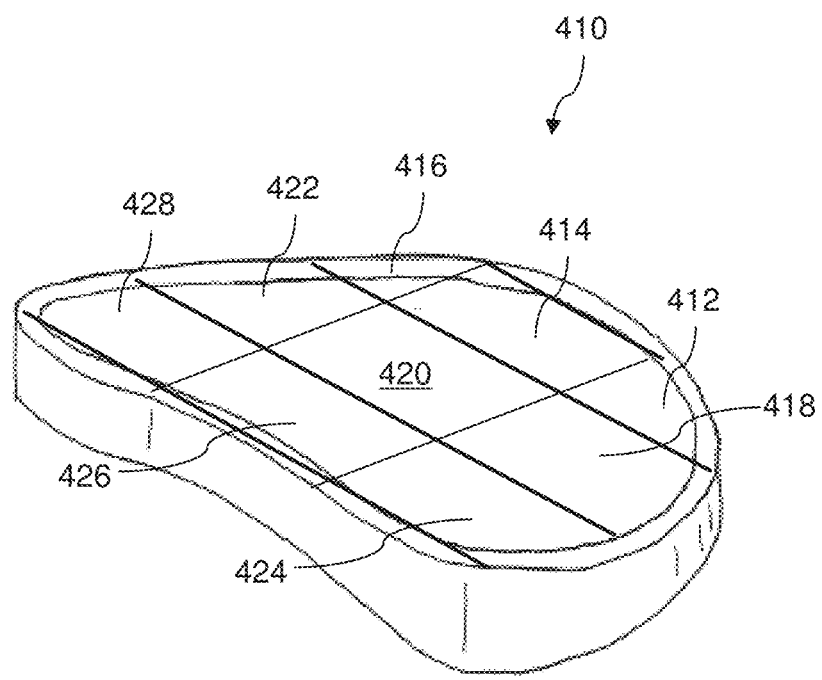
FIG. 29 is a diagrammatic perspective view of a prosthetic device similar to that of FIG. 28, but showing an alternative embodiment of the present disclosure.

Referring now to FIG. 29, shown therein is a prosthetic device 410 according to another embodiment of the present disclosure. In some aspects the prosthetic device 410 is similar to the prosthetic device 400 describe above. In that regard, the prosthetic device 410 is a meniscus replacement device that comprises an upper surface for engaging a portion of a femur, an opposing lower surface for engaging a portion of a tibia, and an outer rim extending between the upper and lower surfaces. The prosthetic device 400 also includes load sensors or pressure sensors 412, 414, 416, 418, 420, 422, 424, 426, and 428. In some instances, the pressure sensors 412, 414, 416, 418, 420, 422, 424, 426, and 428 are regions of a single sensor. In other instances, the pressure sensors 412, 414, 416, 418, 420, 422, 424, 426, and 428 are each a separate sensor. Generally, the pressure sensors 412, 414, 416, 418, 420, 422, 424, 426, and 428 are configured to measure the pressures across the prosthetic device 410, from which peak and/or average pressures can be calculated and/or the pressure distribution across the trial prosthetic device can be mapped. In some instances, the orientation of the sensors 412, 414, 416, 418, 420, 422, 424, 426, and 428 is such that the sensors are associated with a particular region of the prosthetic device 410. As discussed in greater detail below, in some instances the prosthetic device 410 is evaluated regionally and/or globally based on the obtained pressure measurements. Thus, in such instances data of a single sensor (or area of a sensor) is associated with a corresponding region of the prosthetic device 410. In some instances the sensors 412, 414, 416, 418, 420, 422, 424, 426, and 428 are imbedded into the prosthetic device 410. In some embodiments, the sensors 412, 414, 416, 418, 420, 422, 424, 426, and 428 substantially comprise the upper and/or lower surface of the prosthetic device 410. In some embodiments, the sensors 412, 414, 416, 418, 420, 422, 424, 426, and 428 are positioned within the body of the prosthetic device 410 and spaced from the upper and lower surfaces.

Figure 30:
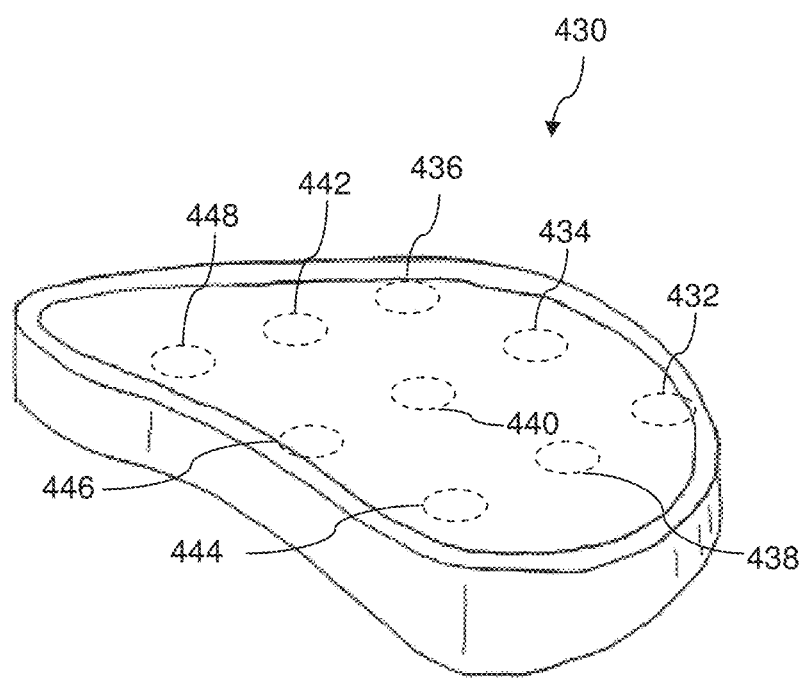
FIG. 30 is a diagrammatic perspective view of a prosthetic device similar to that of FIGS. 28 and 29, but showing an alternative embodiment of the present disclosure.

Referring now to FIG. 30, shown therein is a prosthetic device 430 according to another embodiment of the present disclosure. In some aspects the prosthetic device 430 is similar to the prosthetic devices 400 and 410 describe above. In that regard, the prosthetic device 430 is a meniscus replacement device that comprises an upper surface for engaging a portion of a femur, an opposing lower surface for engaging a portion of a tibia, and an outer rim extending between the upper and lower surfaces. The prosthetic device 430 also includes load sensors or pressure sensors 432, 434, 436, 438, 440, 442, 444, 446, and 448. In some instances, the pressure sensors 432, 434, 436, 438, 440, 442, 444, 446, and 448 are regions of a single sensor. In other instances, the pressure sensors 432, 434, 436, 438, 440, 442, 444, 446, and 448 are each a separate sensor. In some instances, separate pressure sensors 432, 434, 436, 438, 440, 442, 444, 446, and 448 are in communication with one another or a central device to establish a sensor array. Generally, the pressure sensors 432, 434, 436, 438, 440, 442, 444, 446, and 448 are configured to measure the pressures across the prosthetic device 430, from which peak and/or average pressures can be calculated and/or the pressure distribution across the trial prosthetic device can be mapped. In some instances, the orientation of the sensors 432, 434, 436, 438, 440, 442, 444, 446, and 448 is such that the sensors are associated with a particular region of the prosthetic device 430. As discussed in greater detail below, in some instances the prosthetic device 430 is evaluated regionally and/or globally based on the obtained pressure measurements. Thus, in such instances data of a single sensor is associated with a corresponding region of the prosthetic device 430. In some instances the sensors 432, 434, 436, 438, 440, 442, 444, 446, and 448 are imbedded into the prosthetic device 430. In some embodiments, the sensors 432, 434, 436, 438, 440, 442, 444, 446, and 448 substantially comprise the upper and/or lower surface of the prosthetic device 430. In some embodiments, the sensors 432, 434, 436, 438, 440, 442, 444, 446, and 448 are positioned within the body of the prosthetic device 430 and spaced from the upper and lower surfaces.

Figure 31:
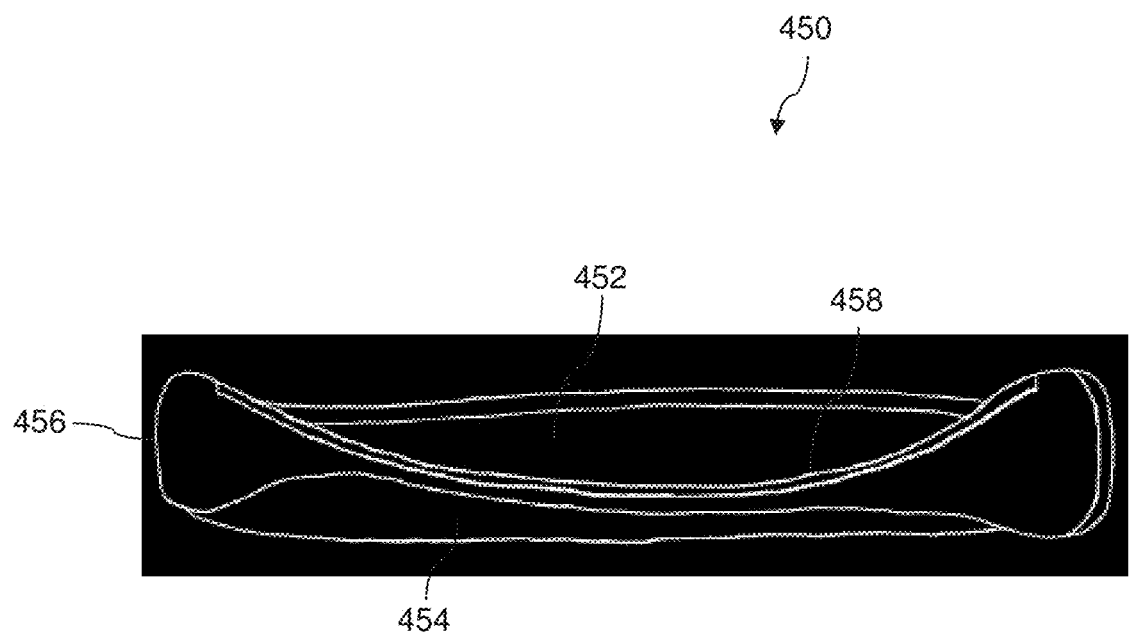
FIG. 31 is a diagrammatic cross-sectional view of a prosthetic device according to one aspect of the present disclosure.

Referring now to FIG. 31, shown therein is a prosthetic device 450 according to one embodiment of the present disclosure. In some aspects the prosthetic device 450 is similar to the prosthetic devices 400, 410, and 430 describe above. In that regard, the prosthetic device 450 is a meniscus replacement device that comprises an upper surface 452 for engaging a portion of a femur, an opposing lower surface 454 for engaging a portion of a tibia, and an outer rim 456 extending between the upper and lower surfaces 452 and 454. The prosthetic device 450 also includes a load or pressure sensor 458. In the illustrated embodiment, the sensor 458 substantially comprises the upper surface 452. Accordingly, the sensor 458 will engage the patient's femur when positioned within the knee joint. Thus, in some instances the sensor 458 measures pressures or loads imparted upon the prosthetic device 450 by the femur during loading of the knee joint. These measured pressures or loads are compared to desired or accepted pressure or load values, in some instances, in order to evaluate the effectiveness of the prosthetic device 450.

Figure 32:
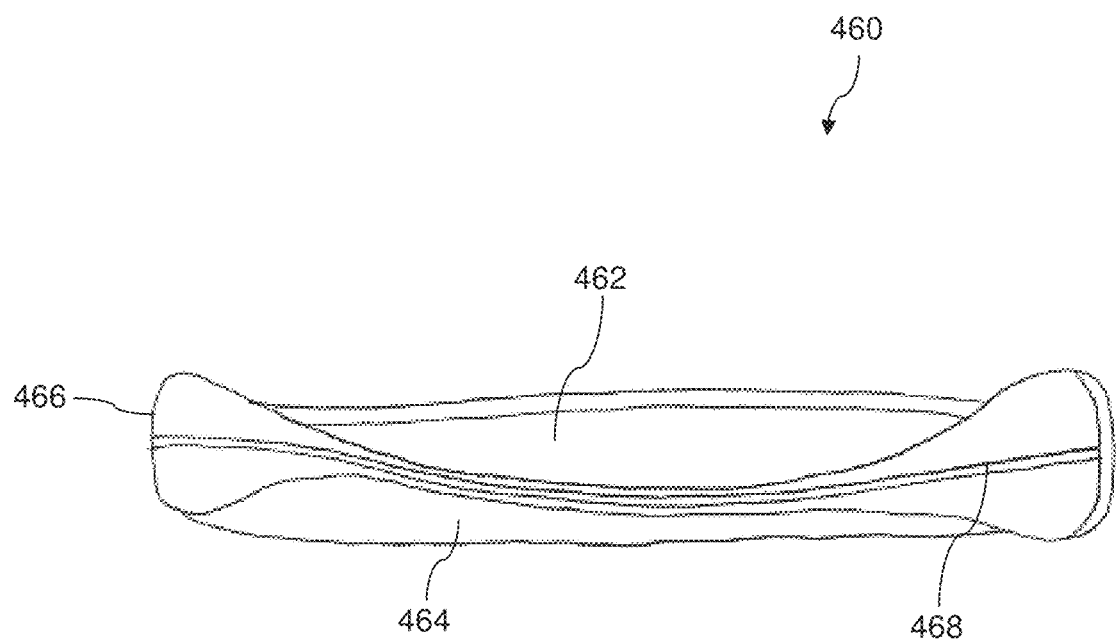
FIG. 32 is a diagrammatic cross-sectional view of a prosthetic device similar to that of FIG. 31, but showing an alternative embodiment of the present disclosure.

Referring now to FIG. 32, shown therein is a prosthetic device 460 according to one embodiment of the present disclosure. In some aspects the prosthetic device 460 is similar to the prosthetic devices 400, 410, 430, and 450 describe above. In that regard, the prosthetic device 460 is a meniscus replacement device that comprises an upper surface 462 for engaging a portion of a femur, an opposing lower surface 464 for engaging a portion of a tibia, and an outer rim 466 extending between the upper and lower surfaces 462 and 464. The prosthetic device 460 also includes a load or pressure sensor 468. In the illustrated embodiment, the sensor 468 is positioned within the body of the prosthetic device 460 and is spaced, at least slightly, from the upper and lower surfaces 462, 464 of the prosthetic device. Accordingly, the sensor 468 does not directly engage the patient's femur or tibia when positioned within the knee joint. However, the sensor 468 measures pressures or loads imparted upon the prosthetic device 450 by the femur and/or tibia during loading of the knee joint. These measured pressures or loads are compared to desired or accepted pressure or load values, in some instances, in order to evaluate the effectiveness of the prosthetic device 460.

Figure 33:
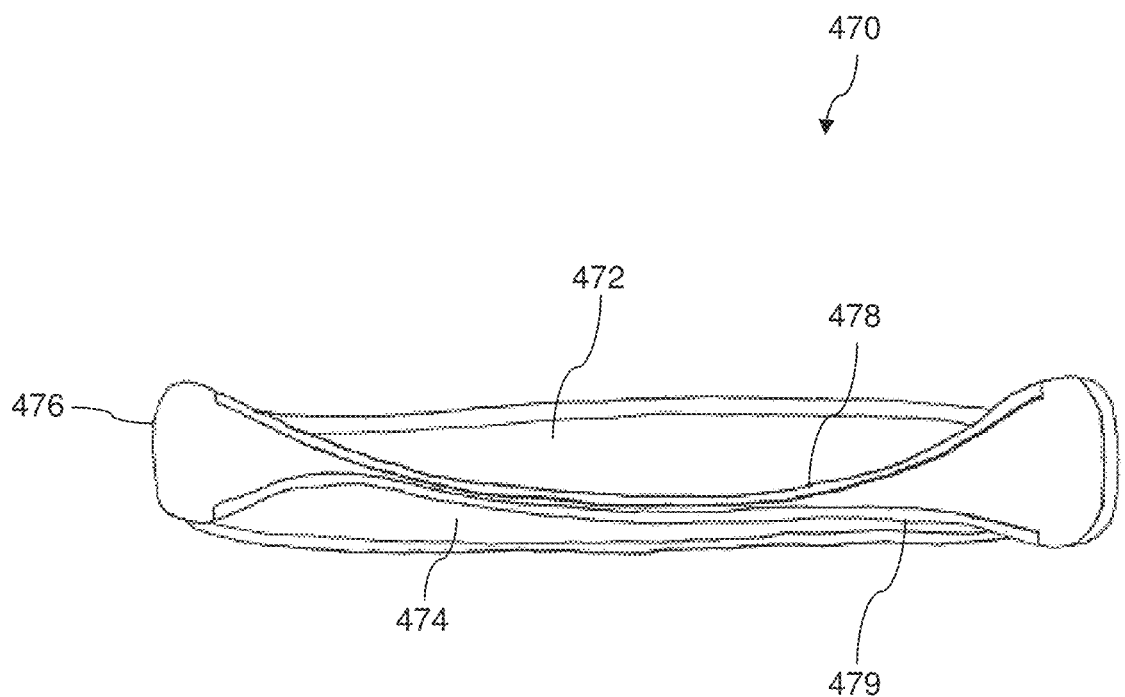
FIG. 33 is a diagrammatic cross-sectional view of a prosthetic device similar to that of FIGS. 31 and 32, but showing an alternative embodiment of the present disclosure.

Referring now to FIG. 33, shown therein is a prosthetic device 470 according to one embodiment of the present disclosure. In some aspects the prosthetic device 470 is similar to the prosthetic devices 400, 410, 430, 450, and 460 describe above. In that regard, the prosthetic device 470 is a meniscus replacement device that comprises an upper surface 472 for engaging a portion of a femur, an opposing lower surface 474 for engaging a portion of a tibia, and an outer rim 476 extending between the upper and lower surfaces 472 and 474. The prosthetic device 470 also includes an upper load or pressure sensor 478 and a lower load or pressure sensor 479. In the illustrated embodiment, the sensor 478 substantially comprises the upper surface 472. Accordingly, the sensor 478 will engage the patient's femur when positioned within the knee joint. Thus, in some instances the sensor 478 measures pressures or loads imparted upon the prosthetic device 470 by the femur during loading of the knee joint. Further, in the illustrated embodiment the sensor 479 substantially comprises the lower surface 474. Accordingly, the sensor 479 will engage the patient's tibia when positioned within the knee joint. Thus, in some instances the sensor 479 measures pressures or loads imparted upon the prosthetic device 470 by the tibia during loading of the knee joint. The pressures or loads measured by the sensors 478, 479 are compared to desired or accepted pressure or load values, in some instances, in order to evaluate the effectiveness of the prosthetic device 470.

Figure 34:
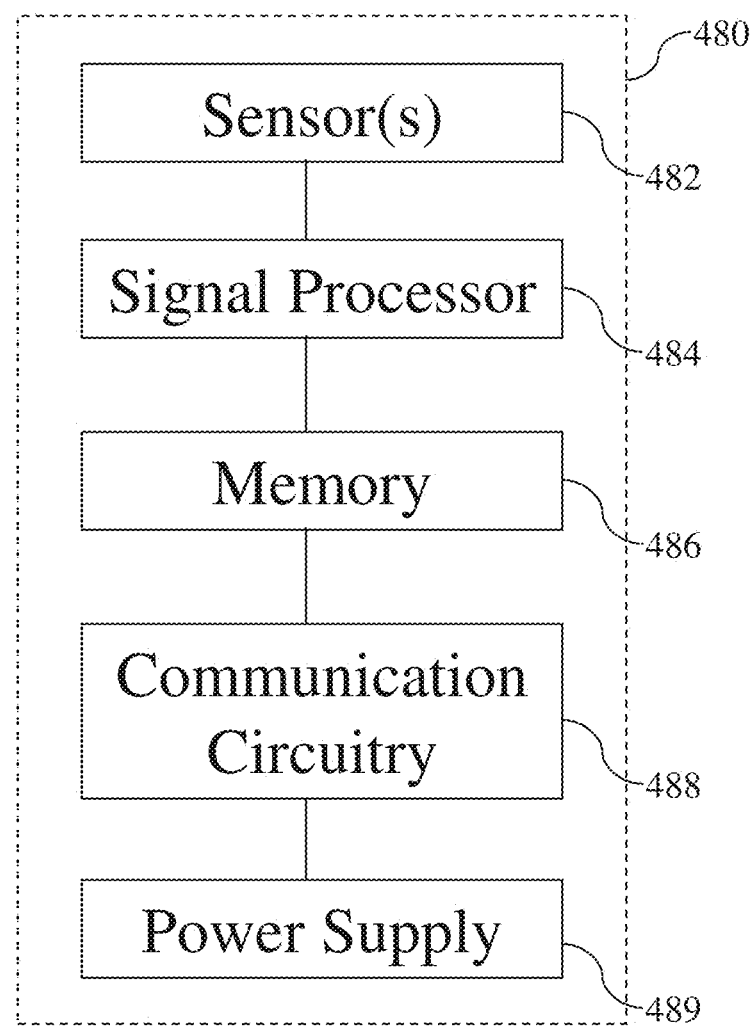
FIG. 34 is a diagrammatic schematic view of a prosthetic device according to one aspect of the present disclosure.

Referring now to FIG. 34, shown therein is a schematic diagram of a prosthetic device 480 according to one embodiment of the present disclosure. In some instances, the prosthetic device 480 is particularly suited as a long-term prosthetic device and/or a longer-term trial prosthetic device. In that regard, in some instances the prosthetic device 480 is configured to monitor pressures or loads imparted upon the prosthetic device 480 over a time period more than 24 hours, more than 1 week, more than 1 month, and/or more than 1 year. In some instances, the prosthetic device 480 is implanted into the patient's knee on a trial basis. Subsequently, the pressure or load data obtained by the prosthetic device is analyzed in order to evaluate the effectiveness of the prosthetic device 480. If the prosthetic device 480 is suitable for the patient, then either the prosthetic device 480 is maintained within the patient's knee for long-term use or the prosthetic device 480 is removed and replaced with a corresponding long-term prosthetic device. If the prosthetic device 480 is not suitable for the patient, then the prosthetic device 480 is removed from the patient's knee and an alternative prosthetic device is implanted. The replacement or alternative prosthetic device is a trial prosthetic device in some instances. In other instances, the replacement or alternative prosthetic device is a long-term prosthetic device.

Accordingly, the prosthetic device 480 includes one or more load or pressure sensors 482. Generally, the sensor(s) 482 are configured to measure the pressures or loads across the prosthetic device 480 during loading of the knee joint. The sensor(s) 482 are in communication with a signal processor 484. The signal processor 484 processes the data obtained from the sensor(s) 482. In some instances, the signal processor 484 directs the raw data obtained from the sensor(s) 482 to memory 486 or other storage media where the raw data is saved. In other instances, the processor 484 processes the raw data from the sensor(s) in order to calculate peak and/or average pressures and/or the pressure distribution across the prosthetic device 480. In some instances, these calculations are performed on a regional and/or sensor-by-sensor basis. Accordingly, in some instances data representative of these calculated measurements are stored in the memory 486 along with or in lieu of the raw data from the sensor(s). The prosthetic device 480 also includes communication circuitry 488. The communication circuitry 488 facilitates communication of the data stored in the memory 486 to an external device. Accordingly, the communication circuitry 488 is any suitable device for communicating with an external device, including wired and wireless communication protocols. Finally, the prosthetic device 480 includes a power supply 489 for providing power to the other components of the prosthetic device as needed. In some instances, the power supply is a battery. In some instances, the power supply is rechargeable.

Figure 35:
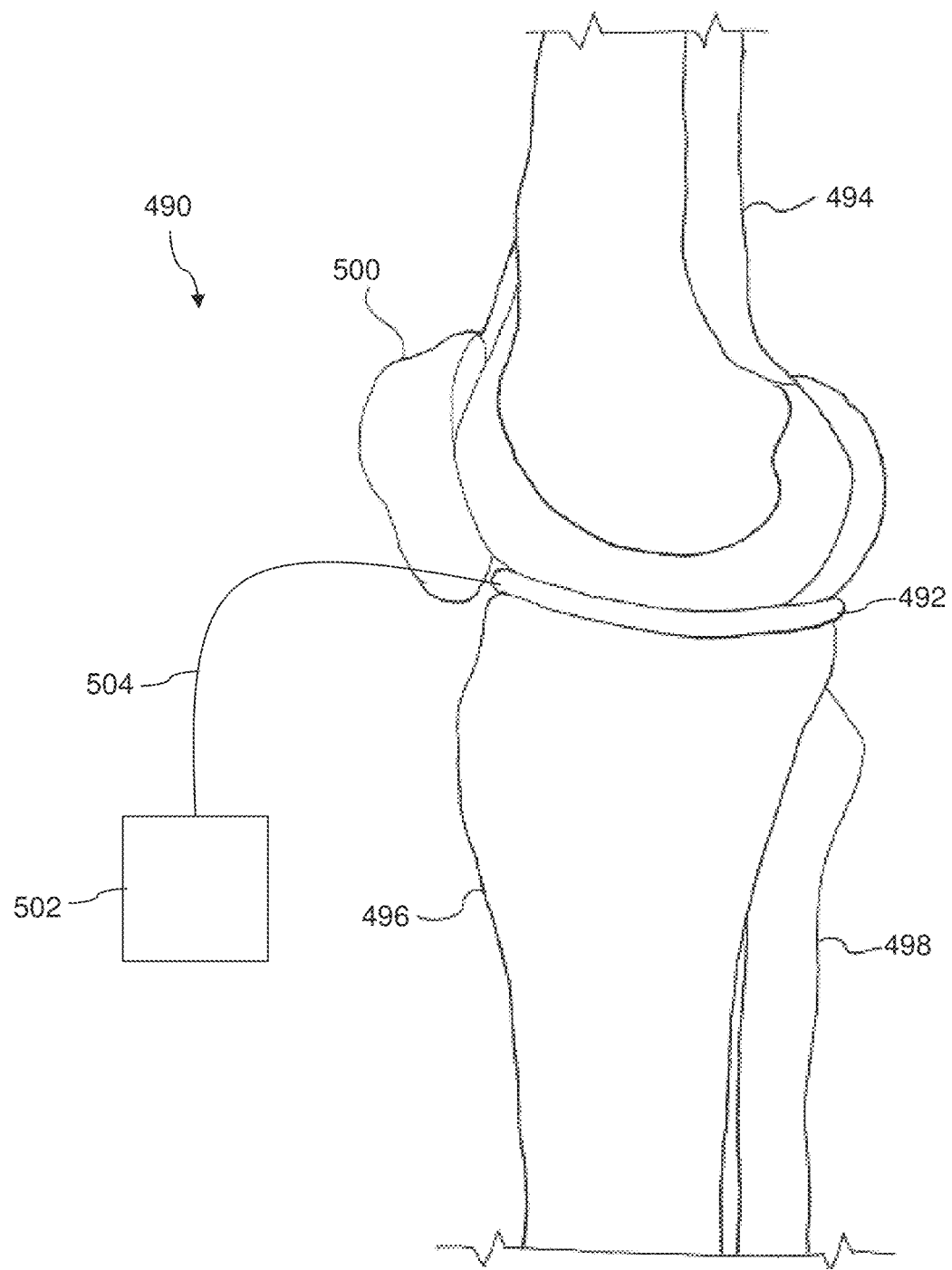
FIG. 35 is a diagrammatic side view of a system according to one aspect of the present disclosure.

Referring now to FIG. 35, shown therein is a system 490 according to one aspect of the present disclosure. In that regard, a prosthetic device 492 is positioned between a femur 494 and a tibia 496 of a knee joint. The fibula 498 and patella 500 are also shown. The prosthetic device 492 is a prosthetic device in accordance with the present disclosure having one or more load or pressure sensors for monitoring a load or pressure imparted upon the prosthetic device 492. The prosthetic device 492 is in communication with an external device 502. In the illustrated embodiment, the prosthetic device 492 communicates with the external device 502 via line 504. In some instances, the line 504 is a USB cable, firewire cable, or other suitable communication cable. In some instances, the external device 502 is a computer or other processing system for processing data received from the prosthetic device 492. In some instances, the external device 502 receives data from the prosthetic device 492 as the prosthetic device 492 is subjected to loads. In other instances, the external device 502 receives data stored by the prosthetic device 492 indicative of previous loadings of the prosthetic device. In that regard, the external device 502 is configured to process and analyze the pressure and load data measured by the sensors of the prosthetic device 492 to evaluate the effectiveness of the prosthetic device in some instances.

Figure 36:
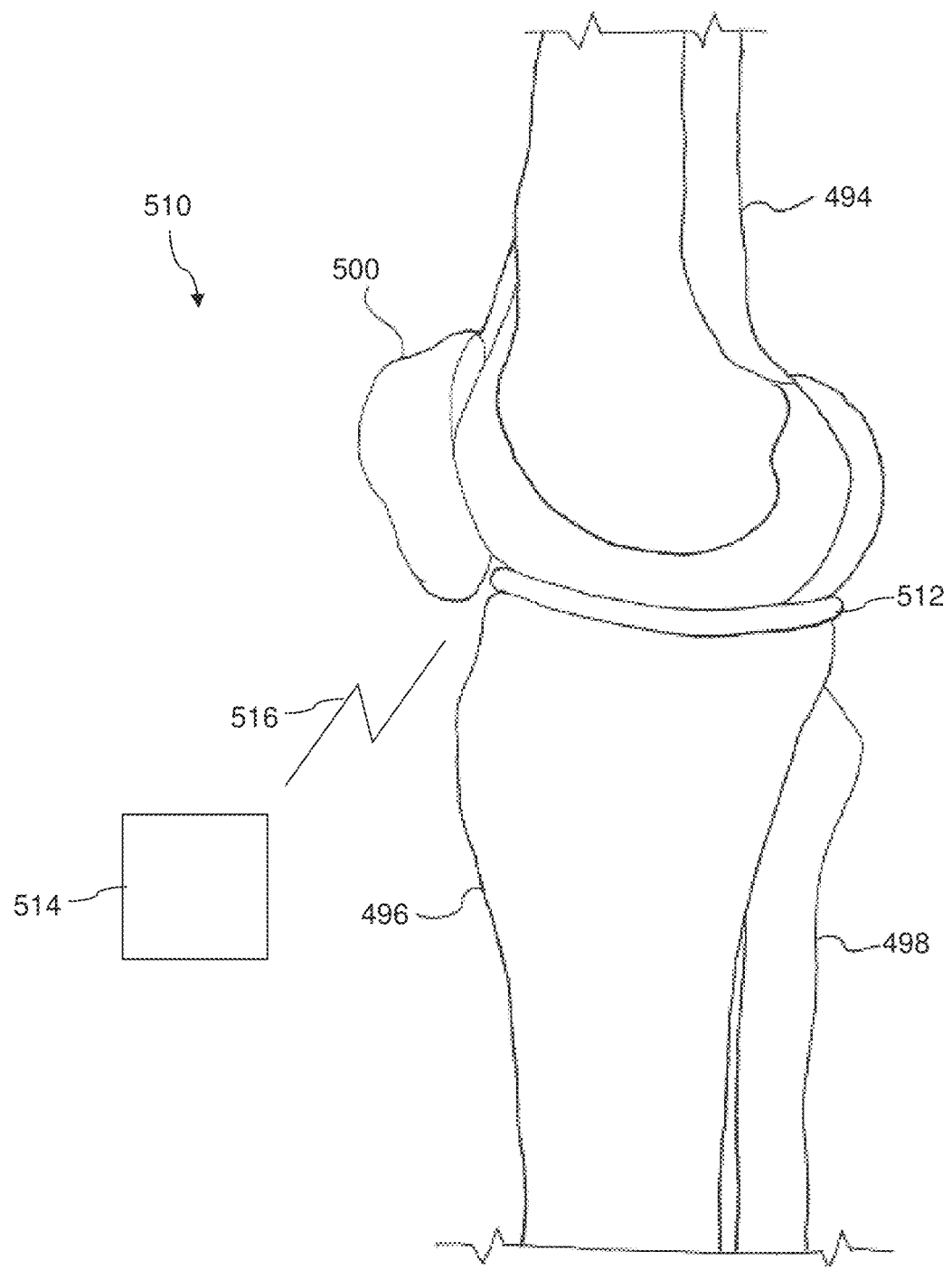
FIG. 36 is a diagrammatic side view of a system similar to that of FIG. 35, but showing an alternative embodiment of the present disclosure.

Referring now to FIG. 36, shown therein is a system 510 according to another aspect of the present disclosure. In some aspects, the system 510 is similar to the system 490 shown above. However, the system 510 illustrates wireless communication between the prosthetic device and external device. In that regard, a prosthetic device 512 is positioned between a femur 494 and a tibia 496 of a knee joint. The fibula 498 and patella 500 are also shown. The prosthetic device 512 is a prosthetic device in accordance with the present disclosure having one or more load or pressure sensors for monitoring a load or pressure imparted upon the prosthetic device 512. The prosthetic device 512 is in communication with an external device 514. In the illustrated embodiment, the prosthetic device 512 communicates with the external device 514 wirelessly, as indicated by signal 516. In some instances, the wireless signal 516 is communicated using bluetooth, 802.11, or other suitable wireless communication protocols. In some instances, the external device 514 is a computer or other processing system for processing data received from the prosthetic device 512. In some instances, the external device 514 is a handheld device. In some instances, the external device 514 receives data from the prosthetic device 512 as the prosthetic device 512 is subjected to loads. In other instances, the external device 514 receives data stored by the prosthetic device 512 indicative of previous loadings of the prosthetic device. In that regard, the external device 514 is configured to process and analyze the pressure and load data measured by the sensors of the prosthetic device 512 to evaluate the effectiveness of the prosthetic device in some instances.

In some instances, the prosthetic device is positioned within subject knee and the patient is positioned on a machine for applying a fixed or known amount of mechanical compression or loading upon the knee joint. With the patient positioned on the machine, the knee is positioned at zero degrees of flexion and all degrees of freedom of the knee are fixed to prevent unwanted bending of the knee during the compression test. The machine then applies mechanical compression or loading to the knee joint. In some instances, the amount of mechanical compression or loading is increased (either incrementally or continuously) until a desired maximum compression or loading force is reached. In some instances, the maximum load is between about 800N and about 2000N. In some instances, the maximum load is approximately 1200N. In some instances, the maximum load applied is at least partially based on the patient's weight and/or activity level. In some instances, the machine applies mechanical compression or loading to the knee joint in cycles, such that the amount of compression or loading is varied. In some such instances, the loading cycles are representative of the loading of the knee joint associated with walking, running, or other common loading cycles. In some instances, the load varies between about ON and about 2000N during the loading cycles. In some embodiments, the amount of load applied to the knee is controlled through a software interface. In some instances, a user controls the amount of load applied to the knee via the user interface. In some instances, the user controls the cycle of loading applied to the knee via the user interface.

Corresponding pressure maps are obtained from the pressure sensors within the prosthetic device based on the loading of the knee joint. The pressure maps are displayed via a software interface in some embodiments. In some instances, the same software interface (or coordinated software interfaces) is utilized for both controlling the amount of load applied to the knee and displaying the corresponding pressure maps. The pressure maps are stored in an accessible database in some instances. In that regard, the pressure maps are associated with characteristics of the knee being tested (such as tibial, femoral, and meniscal dimensions and/or other characteristics) and/or patient characteristics (such as weight, activity level, and/or other characteristics) such that the pressure maps and associated data are retrievable for use in future prosthetic device selection methods.

In some instances the pressure distribution maps attained from the prosthetic devices are analyzed and compared to the pressure distribution maps attained from one or more cadaveric knees. The pressure distribution maps are analyzed and compared on a regional basis, a global basis, or a combination thereof. In some instances, a comparison of local or regional characteristics is advantageous in identifying small, but possibly critical variations in the pressure maps and/or in emphasizing regions of interest. Furthermore, measurement of the total contact area on a global basis and/or global contact pressures may not reveal potentially problematic discrepancies in the contact areas and pressure points of the prosthetic devices. Quantization of the smaller regional areas better approximates the specific shape of the contact areas and the maximum pressure points in some instances. Based on the shape of the natural meniscus, the pressure maps are divided into 9 regions in some embodiments. For example, FIG. 22 illustrates one embodiment of a pressure map shown divided into the 9 separate rectangular regions. Similarly, FIGS. 29 and 30 illustrate prosthetic devices 410 and 430 adapted for monitoring pressures in the 9 regions as shown in the pressure map of FIG. 22. In other instances, the pressure maps are divided into other numbers of regions and/or regions having shapes other than rectangular. Accordingly, the prosthetic devices include similar distributions of sensors and/or sensor regions in these alternative regional breakdowns. In some instances, the regional boundaries of the sensor(s) are determined by a software interface that processes the data received from the prosthetic device.

In some instances, the pressure distributions or pressure maps of the trial prosthetic devices are compared to the accepted pressure distributions for a healthy meniscus. In some instances, the prosthetic devices are scored based on how well the device's pressure map compares to the accepted pressure distributions. In one embodiment, one or more of 3 different measurements are utilized to evaluate the pressure maps of the prosthetic devices: global contact area, regional contact area, and peak regional pressures. These measurements are utilized individually and/or in combination to evaluate the effectiveness and/or suitability of a particular prosthetic device for a particular patient.

The first measurement is the global contact area or utilization of area determination, where the total contact area of the prosthetic device under load is compared to the established value for total contact area of a healthy meniscus. In some instances, this determination is based on whether the total contact area is within a certain percentage of the accepted value. In that regard, in some instances the acceptable percentage variation is between about ±30%. In some instances, the acceptable percentage variation is between about ±20%. In other instances, the acceptable percentage variation is between about ±10%. In some instances, the acceptable percentage variation is selected by the treating medical personnel. If the prosthetic device is within the acceptable percentage variation for utilization of area, then it is considered a suitable prosthetic device in some instances. In other instances, if the prosthetic device is within the acceptable percentage variation for utilization of area, then additional factors are considered to determine whether the prosthetic device is a suitable prosthetic device. If the prosthetic device is not within the acceptable percentage variation for utilization of area, then it is not considered a suitable prosthetic device in some instances. In other instances, if the prosthetic device is not within the acceptable percentage variation for utilization of area, then additional factors are considered to determine whether the prosthetic device is a suitable prosthetic device. Where additional factors are considered, the utilization of area is weighted in the overall evaluation of the prosthetic device. For example, in some instances the utilization of area is weighted to be between 0% and 50% of the overall evaluation of the prosthetic devices.

Generally, the regional contact area parameter is determined, evaluated, and weighted in a manner similar to that of the global contact area discussed above. For example, in some instances a contact area for each region is compared to the established value for the contact area of that region of a healthy meniscus. In some instances, this determination is based on whether the total contact area is within a certain percentage of the accepted value. In that regard, in some instances the acceptable percentage variation is between about ±30%. In some instances, the acceptable percentage variation is between about ±20%. In other instances, the acceptable percentage variation is between about ±10%. In some instances, the acceptable percentage variation is selected by the treating medical personnel. If the prosthetic device is within the acceptable percentage variation for all of the regions, then it is considered a suitable prosthetic device in some instances. In some instances, if the prosthetic device is within the acceptable percentage variation for a majority of the regions, then it is considered a suitable prosthetic device. In other instances, the regions are weighted and a score for each region is obtained. One specific weighting distribution, based on a 9 region analysis as shown in FIG. 22, is set forth in Table 5 above. The sum of the scores for each region provides an overall regional contact score for the device. If the total score meets a predetermined threshold, then the prosthetic device is considered a suitable prosthetic device in some instances. In other instances, additional factors are considered to determine whether the prosthetic device is a suitable prosthetic device regardless of whether all or some of the regions are within the acceptable percentage variation and regardless of the overall regional contact score. Where additional factors are considered, the regional contact area is weighted in the overall evaluation of the prosthetic device. For example, in some instances the regional contact area is weighted to be between 0% and 50% of the overall evaluation of the prosthetic devices.

Finally, peak contact pressures for each of the regions are also considered in some embodiments. In some instances, the peak contact pressure for each region is compared to the accepted peak contact pressure for a healthy meniscus. In other instances, the ratio of the peak contact pressure to the average contact pressure for each region is compared to the accepted ratio of peak contact pressure to average contact pressure. In some instances, this determination is based on whether the peak contact pressure or ratio of peak contact pressure to average contact pressure is within a certain percentage of the accepted value. In that regard, in some instances the acceptable percentage variation is between ±30%. In some instances, the acceptable percentage variation is between about ±20%. In other instances, the acceptable percentage variation is between about ±10%. In some instances, the acceptable percentage variation is selected by the treating medical personnel. If the prosthetic device is within the acceptable percentage variation for all of the regions, then it is considered a suitable prosthetic device in some instances. In some instances, if the prosthetic device is within the acceptable percentage variation for a majority of the regions, then it is considered a suitable prosthetic device. In other instances, the regions are weighted and a score for each region is obtained. One specific weighting distribution, based on a 9 region analysis as shown in FIG. 22, is set forth in Table 6 above. The sum of the scores for each region provides an overall regional peak contact pressure score for the device. If the total score meets a predetermined threshold, then the prosthetic device is considered a suitable prosthetic device in some instances. In other instances, additional factors are considered to determine whether the prosthetic device is a suitable prosthetic device regardless of whether all or some of the regions are within the acceptable percentage variation and regardless of the overall regional peak contact pressure score. Where additional factors are considered, the regional peak contact pressure is weighted in the overall evaluation of the prosthetic device. For example, in some instances the regional peak contact pressure is weighted to be between 0% and 50% of the overall evaluation of the prosthetic devices.

In some instances, the overall evaluation of the prosthetic device is determined by considering the evaluations for the utilization of area, regional contact area, and regional peak contact pressure together. In some instances, one or more additional parameters are taken into consideration in evaluating the prosthetic devices. For example, in some instances implant movement or dislocation is considered. In that regard, if unwanted movement or dislocation of the prosthetic device occurs during trialing of the prosthetic device, then the prosthetic device is not a suitable prosthetic device for the patient. However, if no unwanted movement or dislocation occurs, then the prosthetic device is considered suitable. In some instances, implant impingement upon surrounding ligaments or anatomy is considered. In that regard, if the prosthetic device impinges on any cruciate ligaments or other surrounding anatomy that will be detrimental to the performance of the prosthetic device, then the prosthetic device is not considered suitable. However, if no such impingement occurs, then the prosthetic device is considered suitable. In some instances, the score of the prosthetic device takes into account both the implant movement or dislocation and implant impingement.

Referring now to FIGS. 37-44, shown therein are various screen shots representative of a user interface associated with a system for implementing the methods and prosthetic devices of the present disclosure according to one embodiment of the present disclosure. Additional and/or alternative features of the user interface will be apparent from the following description. Further, some aspects of the method(s) associated with the user interface that are not described in great detail are found above with respect to other embodiments of the present disclosure. In some aspects the user interface and the underlying methods comprise a semi-automated procedure or wizard for selecting a prosthetic device suitable for a particular patient.

Figure 37:
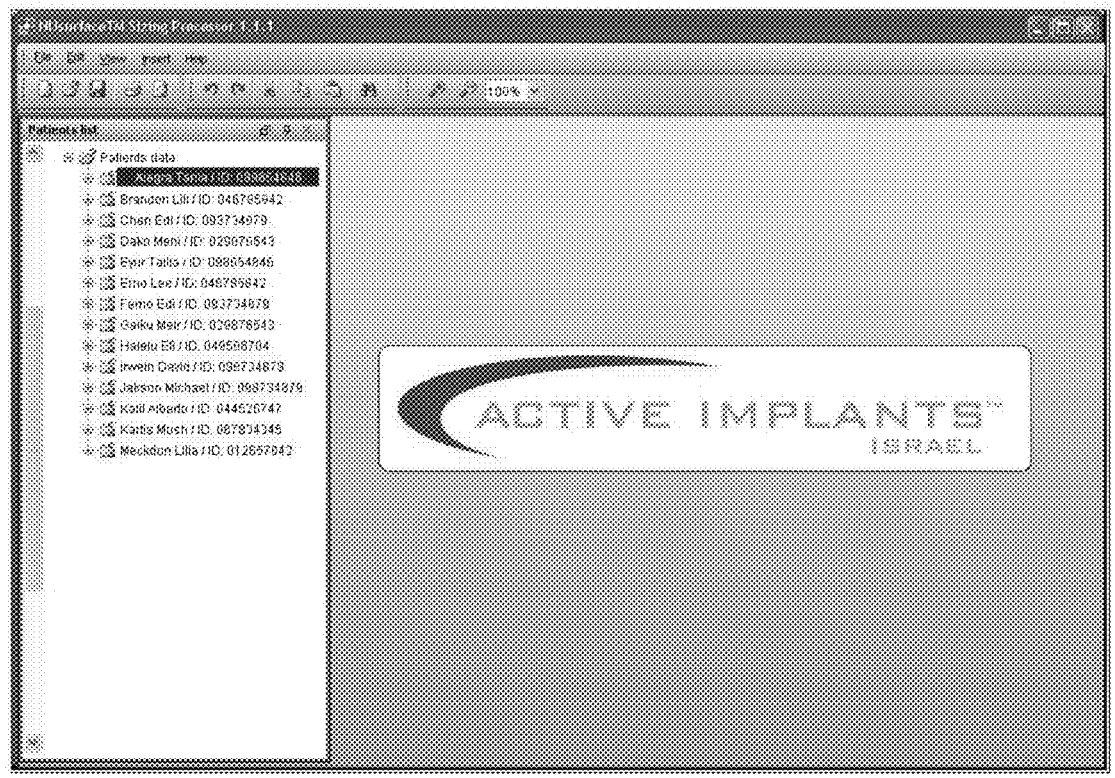
FIG. 37 is a screen shot of a user interface of a system for identifying a suitable prosthetic device for a patient according to one aspect of the present disclosure.

Referring more specifically to FIG. 37, shown therein is a screen shot 600 showing a patient list in a file tree structure of the user interface according to one aspect of the present disclosure. In that regard, the system stores details and information related to each patient. Personal data is uploaded to the system and stored according to FDA standards regarding patients' confidentiality. The system maintains a database containing all of the patient data. In some instances, the database stores patient data for more than one user (e.g., treating physician). In such instances, the system restricts access to the patient data to which the particular user is entitled to view.

Figure 38:
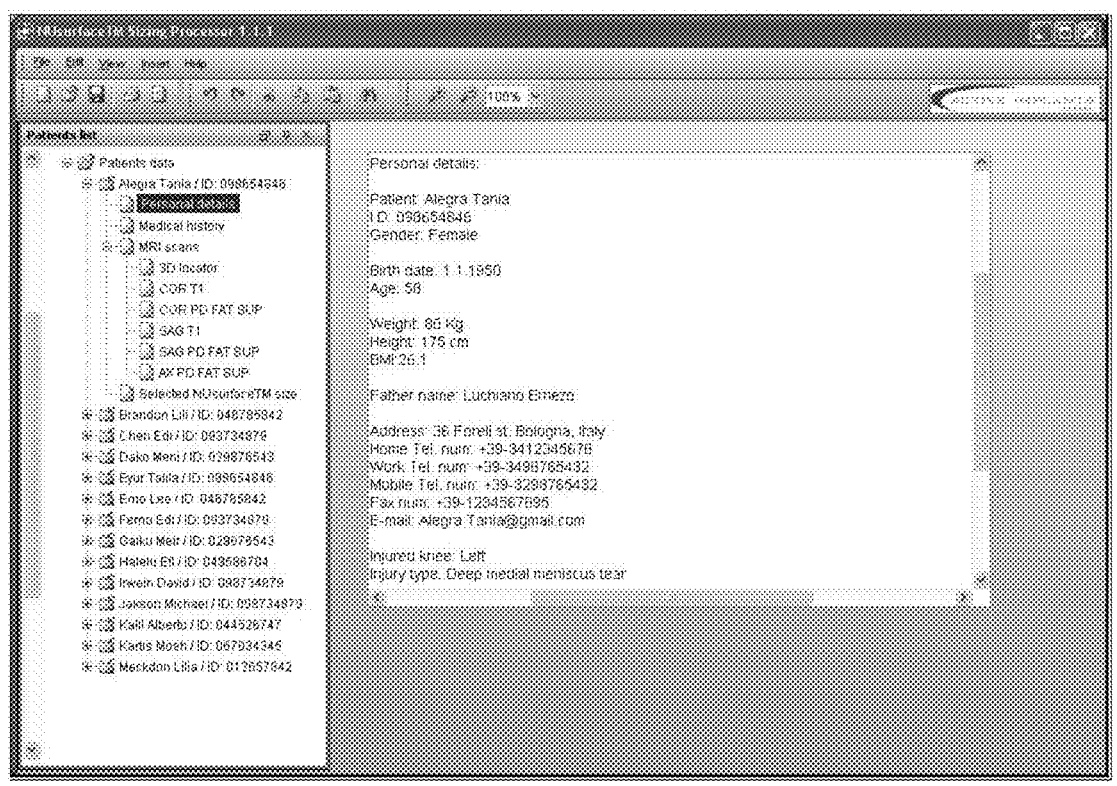
FIG. 38 is another screen shot of the user interface of the system for identifying a suitable prosthetic device for a patient of FIG. 37.

Referring to FIG. 38, shown therein is a screen shot 610 showing a patient detail page for one of the patients of the patient list of FIG. 37. Personal data includes such information as gender, age, weight, height (or BMI), medical history (including previous MRI prognoses), and/or other pertinent medical or personal information. The user has the ability to add an up-to-date prognosis of the current medical status and specific pre-operation information to the patient's detail page. The user also has the ability to add any other detail or notes regarding the patient that the user considers relevant.

Figure 39:
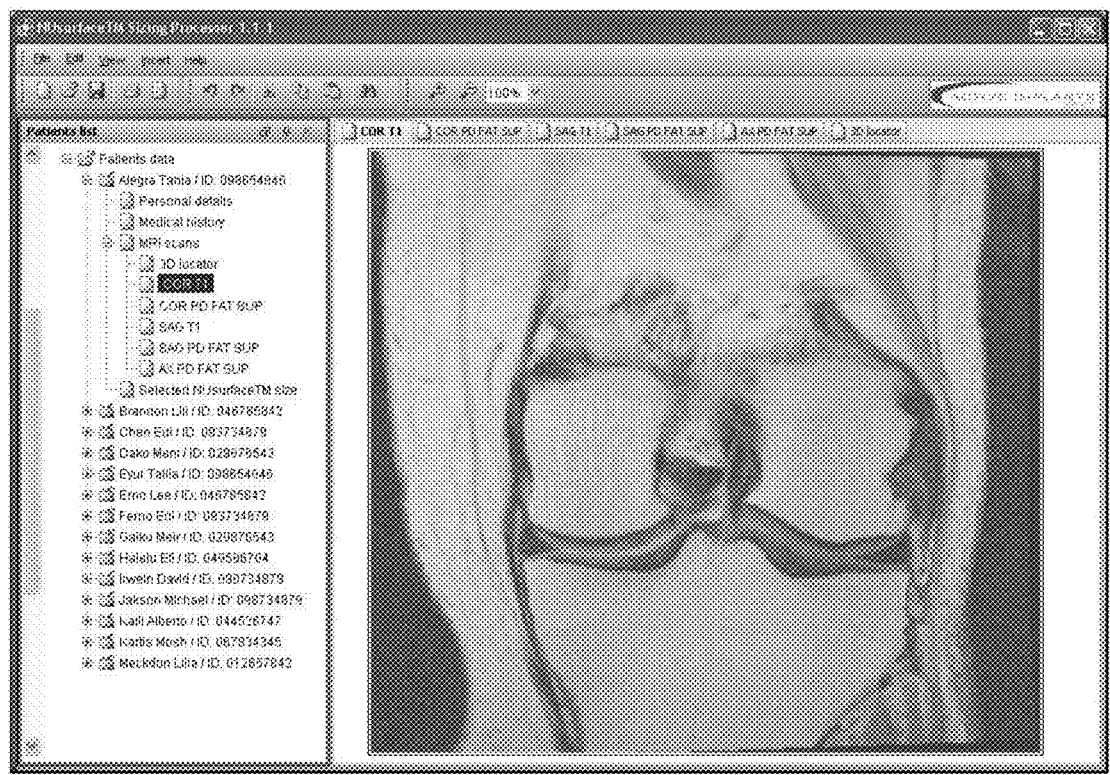
FIG. 39 is another screen shot of the user interface of the system for identifying a suitable prosthetic device for a patient of FIGS. 37 and 38.

Referring to FIG. 39, shown therein is a screen shot 620 showing an MRI image of the patient's knee within the user interface in accordance with one aspect of the present disclosure. In that regard, in some instances MRI images of the patient's knee(s) are uploaded to the system and/or moved within a file folder associated with the patient in some instances. In some instances, the user accesses the drive or memory device in which MRI data is located. Upon accessing the MRI data, the system identifies the existing MRI-sequences and presents them as a file tree on the left side of the screen. In that regard, the system identifies and indicates the scan type (T1, T2 etc), slice thickness, overlapping/gap, and distance between slices in some instances. The user has the ability to browse between the different images of the different series and add comments to the patient's personal data, if warranted. In some instances, from the different images the user identifies or selects for the system the relevant series for the sizing process: coronal, sagittal, and axial scans. In some instances, the preferred scan is T1. In some instances, T2 or PD scans are utilized. The user also excludes non-relevant images from each of the selected MRI-series by marking or selecting the non-relevant images from the series of images in some instances. For example, if the first image of the axial series is a sagittal image for some reason, then the first image will not be taken into account after the user excludes the first image.

In some instances, from the coronal images the user indicates for the system the lateral side of the knee by clicking on the fibula bone when prompted by the system. In that regard, clicking on the fibula involves aligning a cursor associated with a mouse or other input device of the system with the lateral side of the fibula and activating a button or other mechanism of the mouse or other input device to communicate to the system the position of the lateral side of the fibula as viewed in the relevant image. The user also identifies the posterior image for the sizing process (Cor-P-End) as the last image that the tibia can be recognized. Further, the user identifies the anterior image for the sizing process (Cor-A-End) as the last image that the tibia can be recognized.

Similarly, in some instances from the sagittal images the user indicates for the system the lateral side of the knee by clicking on the fibula bone when asked. The user also identifies the medial image of the medial tibialis plateau for the sizing process (Sag-M-End), as the last image that the tibia can be recognized. The user also identifies the lateral image of the medial tibialis plateau for the sizing process (Sag-L-End) as the first image in which the femur notch can be recognized.

Further, in some instances from the axial images the user indicates for the system the lateral side of the knee by clicking on the fibula bone when asked. The user also identifies the femur image for the sizing process (Ax-F), as the first image in which both femoral condyles can be considered as connected. The user also identifies the tibia image for the sizing process (Ax-T), as the first image in which the tibialis plateau articular cartilage cannot be recognized (e.g., only bone is visible in the image).

From the user inputs, the system determines the relevant MRI images for the sizing process. In some instances, the relevant MRI images are determined in the following manner. For the coronal plane images the system counts the number of images between Cor-P-End and Cor-A-End. The middle image is identified as Cor-Mid. If the number of images between Cor-P-End and Cor-A-End is even, then the image of the two middle images in which the tibialis plateau is wider, as measured by side-to-side distance, is identified as Cor-Mid. Next, the system counts the number of images between Cor-Mid and Cor-A-End. The middle image will be identified as Cor-A. If the number of images between Cor-Mid and Cor-A-End is even, then the image of the two middle images that is closest to Cor-Mid is identified as Cor-A. Finally, the system counts the number of images between Cor-Mid and Cor-P-End. The middle image will be identified as Cor-P. If the number of images between Cor-Mid and Cor-P-End is even, then the image of the two middle images that is closest to Cor-Mid is identified as Cor-P.

For the sagittal plane images, the system counts the number of images between Sag-M-End and Sag-L-End. The middle image is identified as Sag-Mid. If the number of images between Sag-M-End and Sag-L-End is even, then the image of the two middle images that is closest to Sag-L-End is identified as Sag-Mid. Next, the system counts the number of images between Sag-Mid and Sag-M-End. The middle image is identified as Sag-M. If the number of images between Sag-Mid and Sag-M-End is even, then the image of the two middle images that is closest to Sag-Mid is identified as Sag-M. Finally, the system counts the number of images between Sag-Mid and Sag-L-End. The middle image is identified as Sag-L. If the number of images between Sag-Mid and Sag-L-End is even, then the image of the two middle images that is closest to Sag-Mid is identified as Sag-L.

Figure 40:
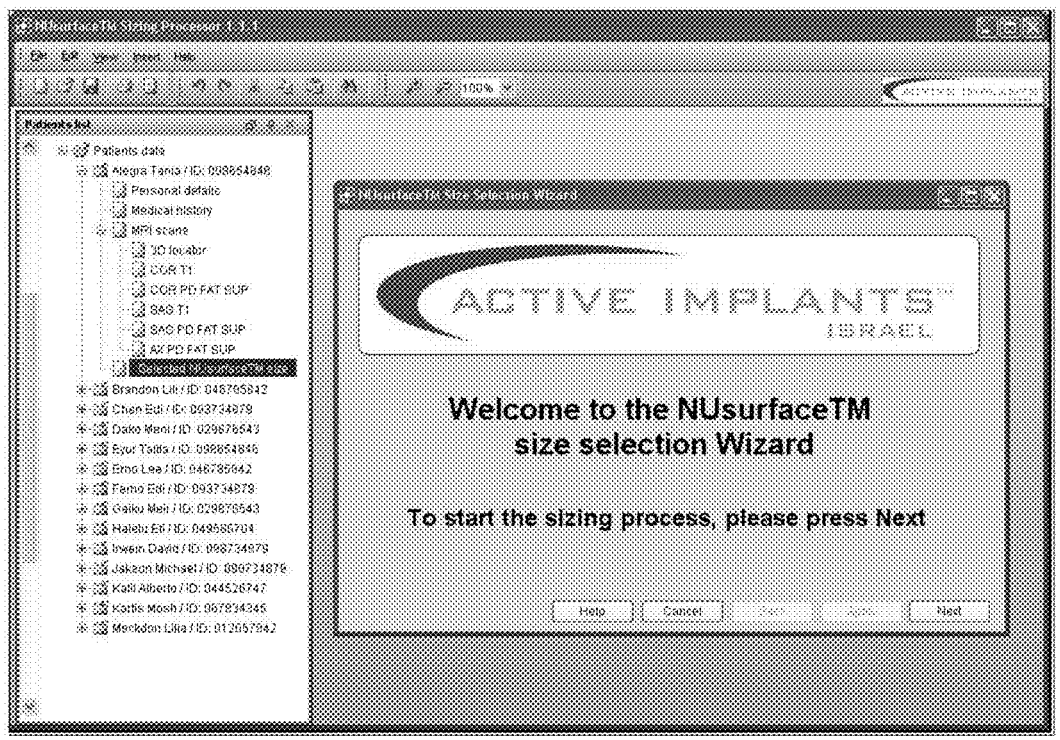
FIG. 40 is another screen shot of the user interface of the system for identifying a suitable prosthetic device for a patient of FIGS. 37, 38, and 39.

Referring now to FIG. 40, shown therein is a screen shot 630 showing a startup screen of an implant size selection wizard in accordance with one aspect of the present disclosure. In that regard, after determination of the relevant images for sizing process a wizard or user guide will prompt the user step-by-step through the subsequent sizing and measurement process. For example, regarding the coronal measurements, the Cor-Mid image is uploaded and shown on the screen or display visible to the user. In some instances, the system guides the user through determining the femoral and tibial functional directions. In one example, on the Cor-Mid image, the user marks the two lowest points, one on each condyle lower border that are used as tangential end-points of a single line. A perpendicular line to the aforementioned line is considered as the femur functional direction at the coronal plane (FFD). The same direction (FFD) is used for the femur in all coronal measurements. Similarly, the user marks the two highest points, one on each side of the tibialis plateau upper border (medial and lateral) that are used as tangential end-points of a single line. A perpendicular line to the aforementioned line is considered as the tibia functional direction at the coronal plane (TFD). The same direction (TFD) is used for the tibia in all coronal measurements.

Figure 41:
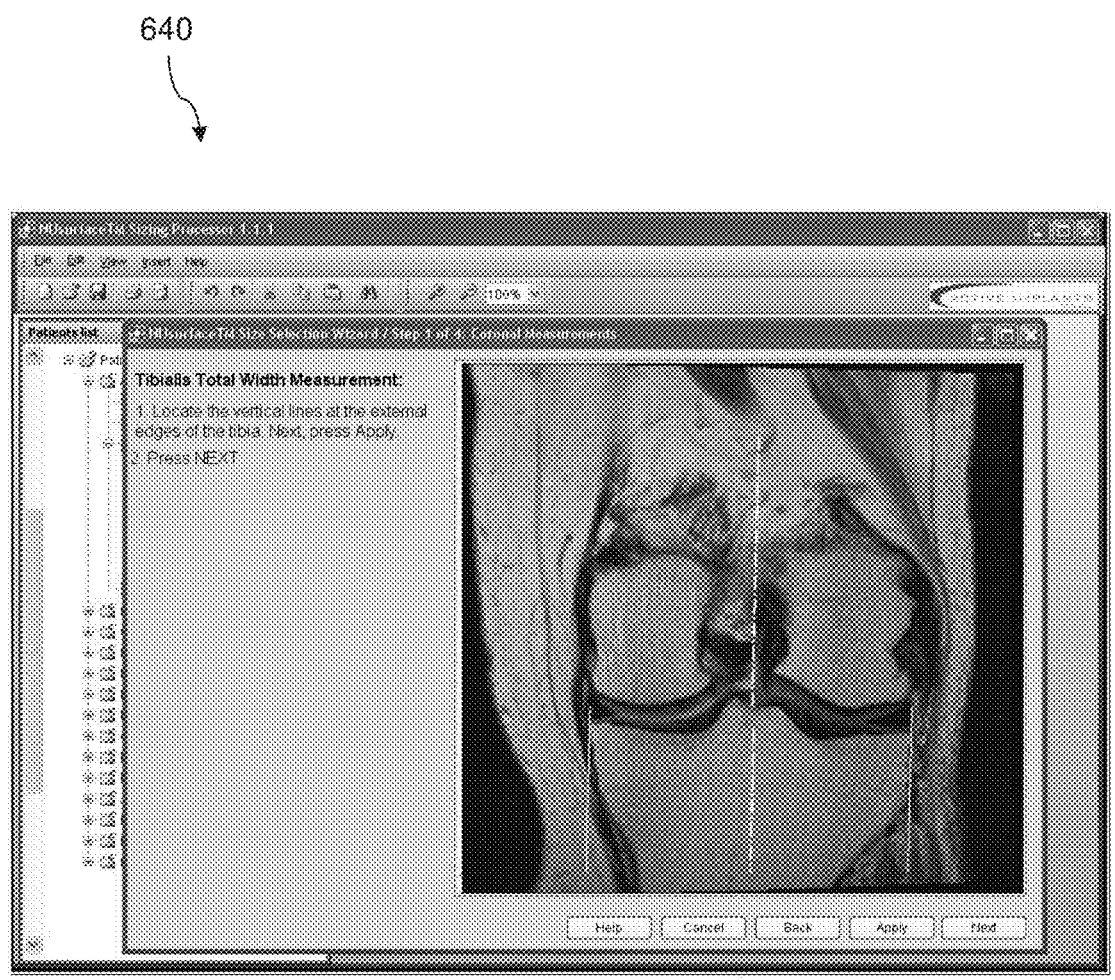
FIG. 41 is another screen shot of the user interface of the system for identifying a suitable prosthetic device for a patient of FIGS. 37, 38, 39, and 40.

From the Cor-Mid image several measurements are obtained by the system. First, several femur measurements are obtained. For example, in one embodiment three lines, parallel to FFD are located on the Cor-Mid image by the system. The user locates or positions two of the lines on the most medial and lateral edges of the condyles and the Femur Condyle Width (FCW) is determined therefrom. The third line is located or positioned by the user on the medial condyle lower border, where the "bending" to the notch is initiating. The Medial Femur Width (FW) is determined by the distance between this line and the aforementioned medial line. Further, several tibia measurements are obtained for the Cor-Mid image. For example, in one embodiment three lines, parallel to TFD are automatically located on the Cor-Mid image. The user locates or positions two lines on the most medial and lateral edges of the tibialis plateau and the Tibialis Plateau Width (TPW) is determined therefrom. For example, referring to FIG. 41, shown therein is a screen shot 640 showing the wizard prompting the user to position the lines for obtaining the Tibialis Plateau Width (TPW) in accordance with one aspect of the present disclosure. The third line is located or positioned by the user on the medial apex of the intercondylar eminence. The Tibialis Plateau Medial Width (MW) is determined by the distance between this line and the aforementioned medial line.

From the Cor-A image several measurements are also obtained by the system. First, several femur measurements are obtained. For example, in one embodiment three lines, parallel to FFD are located on the Cor-A image by the system. The user locates or positions two of the lines on the most medial and lateral edges of the condyles and the Anterior Medial Femur Condyle Width (FCWA) is determined therefrom. The third line is located or positioned by the user between the condyles on the highest point of the notch. The Anterior Medial Femur Width (FWA) is determined by the distance between this line and the aforementioned medial line. Further, several tibia measurements are obtained from the Cor-A image. For example, in one embodiment three lines, parallel to TFD are automatically located on the Cor-A image. The user locates or positions two lines on the most medial and lateral edges of the tibialis plateau and the Tibialis Plateau Anterior Width (TPWA) is determined therefrom. The third line is located or positioned by the user on the medial apex of the intercondylar eminence. The Tibialis Plateau Anterior Medial Width (MWA) is determined by the distance between this line and the aforementioned medial line.

From the Cor-P image several measurements are also obtained by the system. First, several femur measurements are obtained. For example, in one embodiment three lines, parallel to FFD are located on the Cor-P image by the system. The user locates or positions two of the lines on the most medial and lateral edges of the condyles and the Posterior Medial Femur Condyle Width (FCWP) is determined therefrom. The third line is located or positioned by the user between the condyles on the highest point of the notch. The Posterior Medial Femur Width (FWP) is determined by the distance between this line and the aforementioned medial line. Further, several tibia measurements are obtained from the Cor-P image. For example, in one embodiment three lines, parallel to TFD are automatically located on the Cor-P image. The user locates or positions two lines on the most medial and lateral edges of the tibialis plateau and the Tibialis Plateau Posterior Width (TPWP) is determined therefrom. The third line is located or positioned by the user on the medial apex of the intercondylar eminence. The Tibialis Plateau Posterior Medial Width (MWP) is determined by the distance between this line and the aforementioned medial line.

Regarding the sagittal measurements, the Sag-Mid image is uploaded and shown on the screen or display visible to the user. In some instances, the system guides the user through determining the femoral and tibial functional directions. In the sagittal plane, the femur and tibia share the same defined direction. In one example, on the Sag-Mid image, the user marks the two highest points, one on each side of the tibialis plateau upper border (anterior and posterior) that are used as tangential end-points of a single line. A perpendicular line to the aforementioned line is considered as the knee functional direction at the sagittal plane (SFD). The same functional direction (SFD) is used for both the femur and the tibia in all sagittal measurements.

Figure 42:
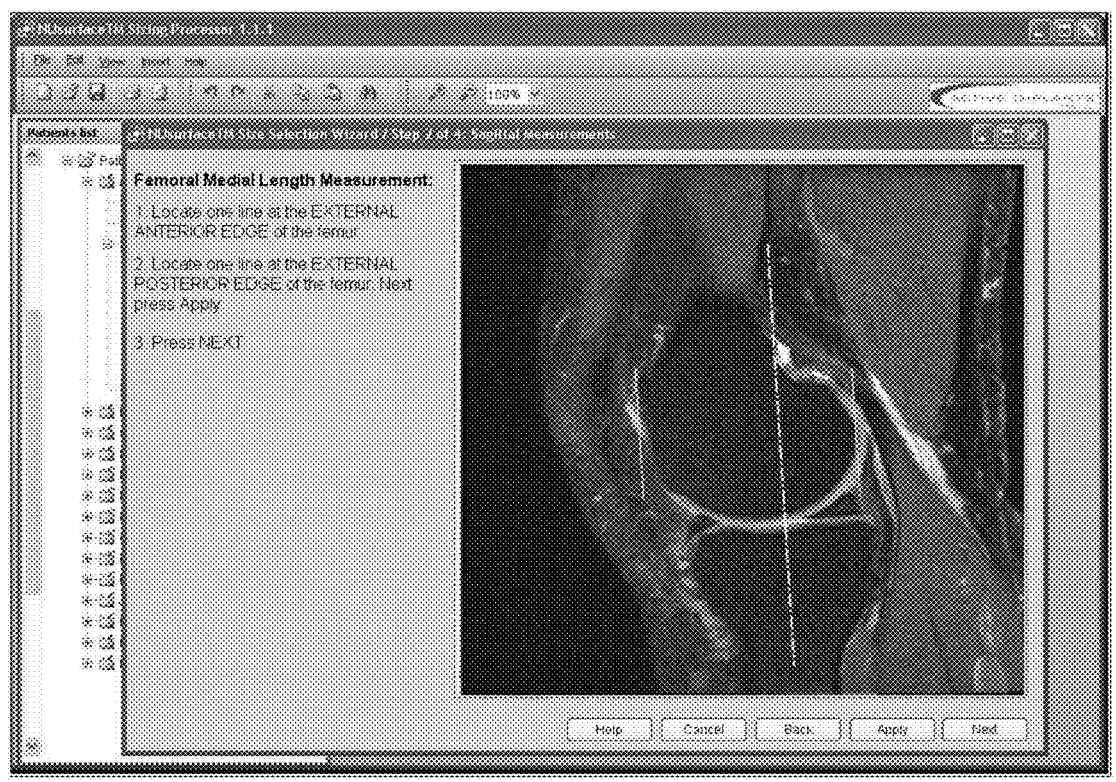
FIG. 42 is another screen shot of the user interface of the system for identifying a suitable prosthetic device for a patient of FIGS. 37, 38, 39, 40, and 41.
Figure 44:
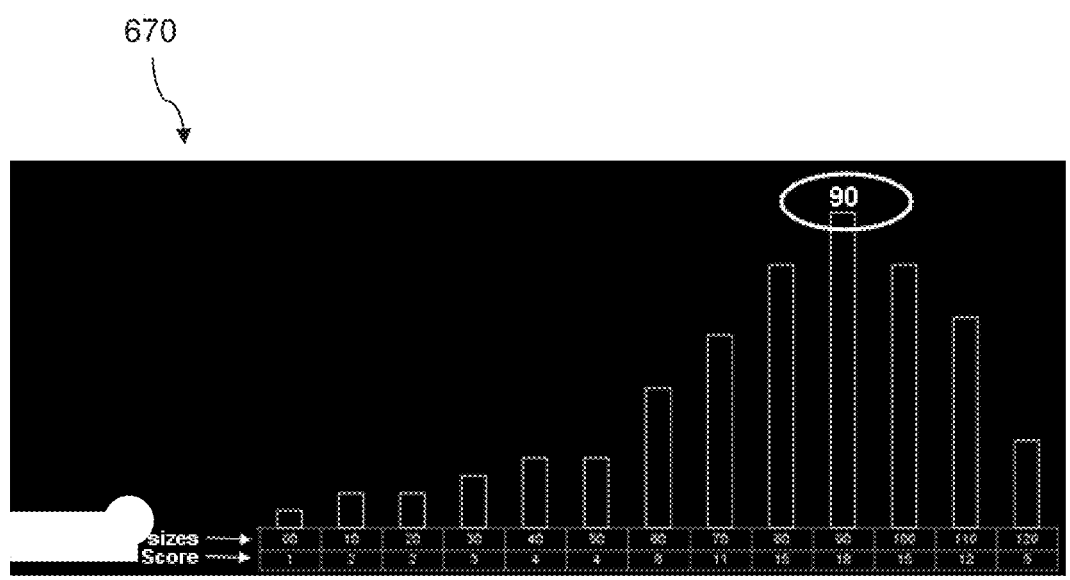
FIG. 44 is a bar graph showing a scoring of a library of prosthetic devices according to one aspect of the present disclosure.

From the Sag-Mid image several measurements are obtained by the system. First, at least one femur measurement is obtained. For example, in one embodiment two lines, parallel to SFD are located on the Sag-Mid image by the system. The user locates or positions the two lines on the medial and lateral edges of the condyles and the Medial Femoral Condyle Length (FL) is determined by the distance therebetween. For example, referring to FIG. 42, shown therein is a screen shot 650 showing the wizard prompting the user to position the lines for obtaining the Medial Femoral Condyle Length (FL) in accordance with one aspect of the present disclosure. Similarly, at least one tibia measurement is obtained. In that regard, two lines, parallel to SFD are located on the Sag-Mid image by the system. The user locates or positions the two lines on the medial and lateral edges of the tibia and the Tibialis Plateau Medial Length (ML) is determined by the distance therebetween.

From the Sag-M image several measurements are also obtained by the system. For example, in one embodiment two lines, parallel to SFD are located on the Sag-M image by the system. The user locates or positions the two lines on the medial and lateral edges of the condyles and the Medial Femoral Condyle Length-Medial Edge (FLM) is determined by the distance therebetween. Similarly, at least one tibia measurement is obtained. In that regard, two lines, parallel to SFD are located on the Sag-M image by the system. The user locates or positions the two lines on the medial and lateral edges of the tibia and the Tibialis Plateau Medial Length-Medial Edge (MLM) is determined by the distance therebetween.

Further, from the Sag-L image several measurements are obtained by the system. For example, in one embodiment two lines, parallel to SFD are located on the Sag-L image by the system. The user locates or positions the two lines on the medial and lateral edges of the condyles and the Medial Femoral Condyle Length-Lateral Edge (FLL) is determined by the distance therebetween. Similarly, at least one tibia measurement is obtained. In that regard, two lines, parallel to SFD are located on the Sag-L image by the system. The user locates or positions the two lines on the medial and lateral edges of the tibia and the Tibialis Plateau Medial Length-Lateral Edge (MLL) is determined by the distance therebetween.

Regarding the axial measurements, the Ax-F image is uploaded and shown on the screen or display visible to the user. On the Ax-F image, the user marks the area defined by the femoral condyles using a spline tool based on "point-after-point" procedure to form a closed loop. The system calculates the area defined by the point-after-point procedure to determine the Femoral Condyles Area (FA). For example, referring to FIG. 43, shown therein is a screen shot 660 showing the wizard prompting the user to point-trace the femoral condyles border in order to obtain the Femoral Condyle Area (FA) in accordance with one aspect of the present disclosure. The user also indicates the lowest and highest points of the connection between the condyles to form a mid-line dividing between medial and lateral sides. Based on the mid-line, the system calculates the Femoral Condyle Medial Area (FMA).

Similarly, the Ax-T image is uploaded and shown on the screen or display visible to the user. On the Ax-T image, the user marks the area defined by the tibialis plateau using a spline tool based on "point-after-point" procedure to form a closed loop. The system calculates the area defined by the point-after-point procedure to determine the Tibialis Plateau Area (TA). Further, based on a mid-line, the system calculates the Tibialis Plateau Medial Area (TMA). In some instances, a mid-line corresponding to the mid-line defined for the Ax-F image is utilized. In other instances, the user indicates upper and lower midpoints of the tibialis plateau from which a mid-line is defined and utilized for calculating the Tibialis Plateau Medial Area (TMA).

After obtaining the desired measurements, the measurements are utilized to select a suitable prosthetic device from a library of available prosthetic devices. For exemplary purposes, a library containing 13 prosthetic devices of similar structure but varying size is discussed. In that regard, the prosthetic devices are indicated by two digit reference numerals from 00 to 120 in multiples of 10 (i.e., 00, 10, 20, . . . , 110, 120). However, no limitations are intended thereby. Rather, the library includes additional or fewer prosthetic devices in some instances. Further, in some instances the library includes prosthetic devices having different structures and/or features in addition to different sizes. The corresponding measurement for each prosthetic device size (00 to 120) is compared to the measurements obtained from the MRI analysis. A particular prosthetic device size receives a single point if the size of the prosthetic device falls within the normative range for that measurement as determined by the MRI analysis, where the normative range is defined by the actual measurement value determined by the MRI analysis plus the standard deviation for that measurement as set forth in Table 2 above. It should be noted that more than one prosthetic device size will get a point from the same measurement in some instances. Adding up the scores for each measurement, each size of prosthetic device will have a final score. In some instances, the analysis includes 22 measurements, so the maximum score for any one prosthetic device is 22 points. In other instances, additional or fewer measurements are utilized. Further, in some instances the measurements are weighted to highlight the importance of certain measurements.

Figure 45:
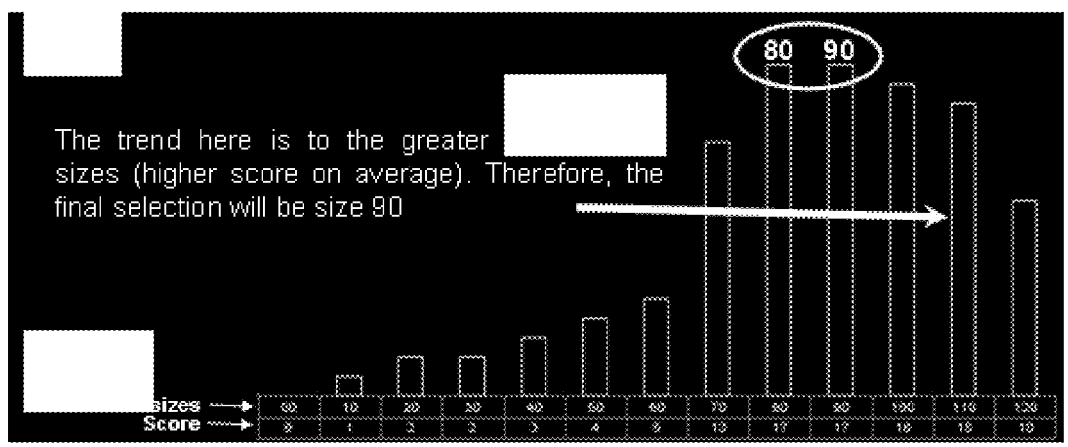
FIG. 45 is a bar graph showing a scoring of a library of prosthetic devices similar to that of FIG. 44, but showing an alternative embodiment of the present disclosure.
Figure 46:
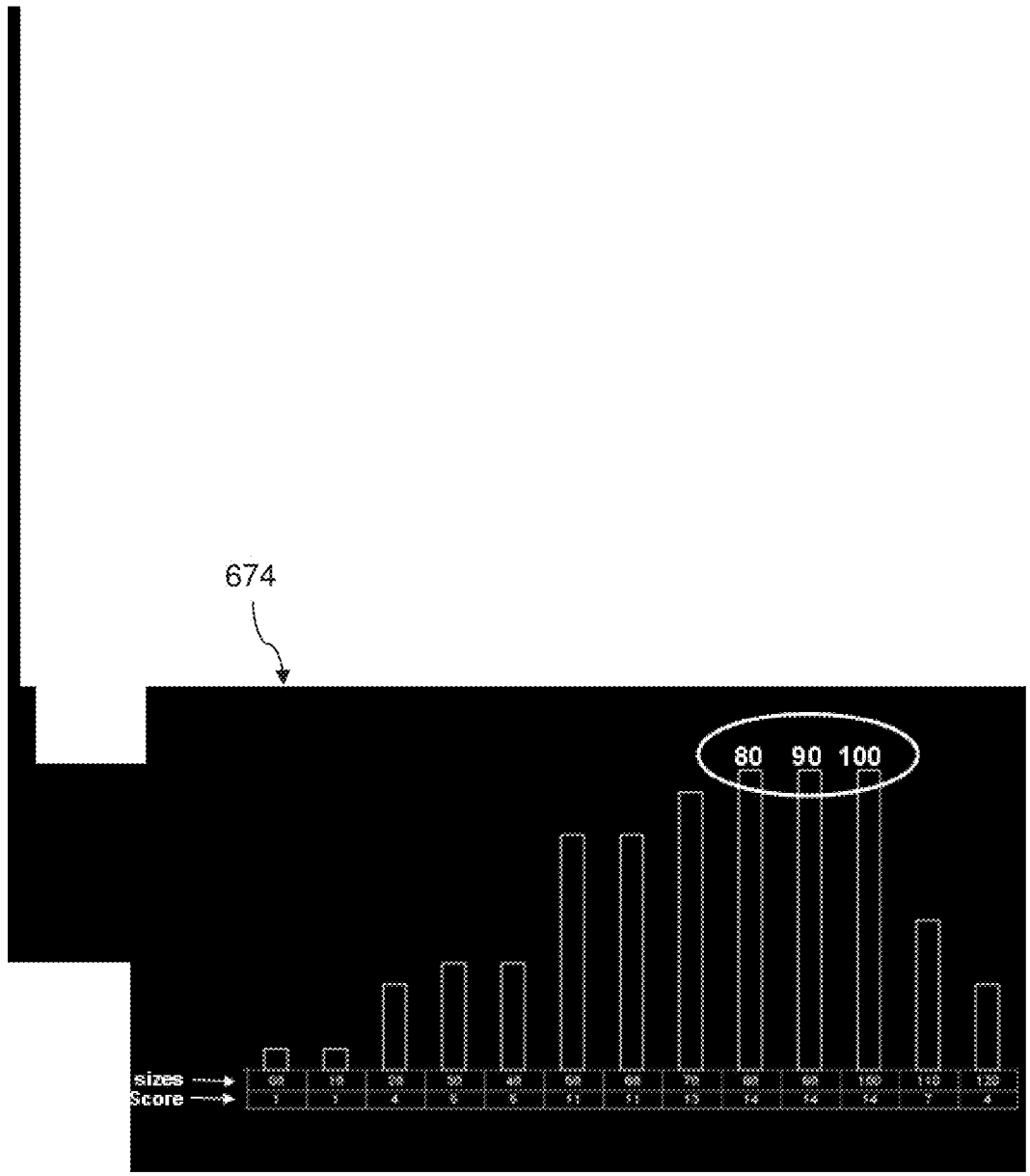
FIG. 46 is a bar graph showing a scoring of a library of prosthetic devices similar to that of FIGS. 44 and 45, but showing an alternative embodiment of the present disclosure.
Figure 47:
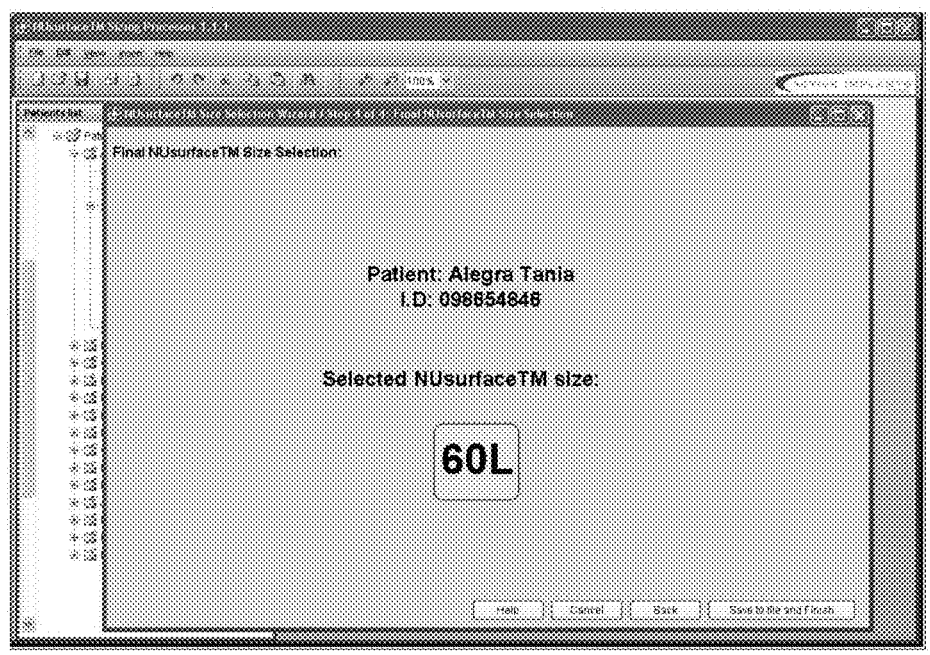
FIG. 47 is another screen shot of the user interface of the system for identifying a suitable prosthetic device for a patient of FIGS. 37, 38, 39, 40, 41, 42, and 43.

The prosthetic device size with the highest score will be identified by the system as the optimal prosthetic device for the patient. For example, as shown in the chart 670 of FIG. 44, the prosthetic device size 90 having a score of 18 is identified as the optimal prosthetic device for the patient. In the case where two prosthetic device sizes have the same total score, then the size closer to where the scoring trend is located will be selected. For example, as shown in the chart 672 of FIG. 45, the prosthetic device sizes 80 and 90 have the same total score of 17, but the larger size prosthetic devices (i.e., 100 and 110) have substantially greater scores than the smaller size prosthetic devices (i.e., 60 and 70). Accordingly, in this instance the trending is towards the larger prosthetic devices. Accordingly, the prosthetic device 90 is selected as the optimal prosthetic device for the patient. If there is no discernable difference in the trending where two prosthetic devices have the same total score, then the smaller of the two sizes is selected. In the case of three prosthetic device sizes having equal scores, the middle size is selected and identified as the optimal prosthetic device for the patient. For example, as shown in the chart 674 of FIG. 46, the prosthetic device sizes 80, 90, and 100 all have the same total score of 14. Accordingly, the prosthetic device size 90 is identified as the optimal prosthetic device for the patient. Referring to FIG. 47, shown therein is a screen shot 680 showing the wizard indicating to the user that prosthetic device size 60L is the optimal prosthetic device for the patient in accordance with one aspect of the present disclosure.

While the principles of the present disclosure have been set forth using the specific embodiments discussed above, no limitations should be implied thereby. Any and all alterations or modifications to the described devices, instruments, and/or methods, as well as any further application of the principles of the present disclosure that would be apparent to one skilled in the art are encompassed by the present disclosure even if not explicitly discussed herein. It is also recognized that various presently unforeseen or unanticipated alternatives, modifications, and variations of the present disclosure may be subsequently made by those skilled in the art. All such variations, modifications, and improvements that would be apparent to one skilled in the art to which the present disclosure relates are encompassed by the following claims.

The invention claimed is:

1. A method for replacing a damaged meniscus within a knee joint of a patient, the method comprising:
   receiving, at a computer, a medical image of a knee joint obtained by a medical imaging device, the medical image comprising a tibial plateau;
   identifying, by the computer, a medial edge of the tibial plateau in the medical image;
   identifying, by the computer, a lateral edge of the tibial plateau in the medical image;
   determining, by the computer, a width of the tibial plateau between the medial edge and the lateral edge;
   determining, by the computer, one or more suitable meniscus prosthetic devices, from a plurality of meniscus prosthetic devices, for replacing the damaged meniscus within the knee joint based on the width of the tibial plateau; and
   outputting, to a display in communication with the computer, a graphical representation of the one or more suitable meniscus prosthetic devices; and
   providing at least one implant corresponding to the one or more suitable meniscus prosthetic devices determined by the computer.

2. The method of claim 1, wherein the medical image comprises at least one of an x-ray image, a magnetic resonance imaging (MRI) image, or a computed tomography (CT) image.

3. The method of claim 1, wherein the medical image comprises at least one of a coronal image or an axial image.

4. The method of claim 1,
   wherein identifying the medial edge comprises receiving a first user input locating the medial edge in the medical image, and
   wherein identifying the lateral edge comprises receiving a second user input locating the lateral edge in the medical image.

5. The method of claim 1, wherein receiving the medical image comprises receiving an upload.

6. The method of claim 1, further comprising determining a plurality of measurements of the knee joint using the medical image, wherein determining the one or more suitable meniscus prosthetic devices is based on the plurality of measurements.

7. The method of claim 1, wherein the plurality of meniscus prosthetic devices comprises a plurality of sizes, and wherein determining the one or more suitable meniscus prosthetic devices comprises selecting a suitable size from the plurality of sizes.

8. The method of claim 7, wherein the determining the one or more suitable meniscus prosthetic devices comprises scoring the plurality of meniscus prosthetic devices to identify a best fit in the knee joint.

9. The method of claim 8, wherein the determining the one or more suitable meniscus prosthetic devices is based on a trend in the scoring.

10. The method of claim 8, wherein the determining the one or more suitable meniscus prosthetic device comprises selecting a smaller meniscus prosthetic device when the scoring identifies two meniscus prosthetic devices of different sizes.

11. A system for replacing a damaged meniscus within a knee joint of a patient, the system comprising:
    a computer configured to:
       receive a medical image of a knee joint obtained by a medical imaging device, the medical image comprising a tibial plateau;
       identify a medial edge of the tibial plateau in the medical image;
       identify a lateral edge of the tibial plateau in the medical image;
       determine a width of the tibial plateau between the medial edge and the lateral edge;
       determine, from a plurality of meniscus prosthetic devices, one or more suitable meniscus prosthetic devices for replacing the damaged meniscus within the knee joint based on the width of the tibial plateau; and
       output, to a display in communication with the computer, a graphical representation of the one or more suitable meniscus prosthetic devices; and
    at least one implant corresponding to the one or more suitable meniscus prosthetic devices determined by the computer.

12. The system of claim 11, wherein the medical image comprises at least one of an x-ray image, a magnetic resonance imaging (MRI) image, or a computed tomography (CT) image.

13. The system of claim 11, wherein the medical image comprises at least one of a coronal image or an axial image.

14. The system of claim 11,
    wherein the computer identifying the medial edge comprises receiving a first user input locating the medial edge in the medical image, and
    wherein the computer identifying the lateral edge comprises receiving a second user input locating the lateral edge in the medical image.

15. The system of claim 11, wherein the computer receiving the medical image comprises receiving an upload.

16. The system of claim 11, wherein the computer is further configured to determine a plurality of measurements of the knee joint using the medical image, and wherein the computer determining the one or more suitable meniscus prosthetic devices is based on the plurality of measurements.

17. The system of claim 11, wherein the plurality of meniscus prosthetic devices comprises a plurality of sizes, and wherein the computer determining the one or more suitable meniscus prosthetic devices comprises selecting a suitable size from the plurality of sizes.

18. The system of claim 17, wherein the computer determining the one or more suitable meniscus prosthetic devices comprises scoring the plurality of meniscus prosthetic devices to identify a best fit in the knee joint.

19. The system of claim 18, wherein the computer determining the one or more suitable meniscus prosthetic devices is based on a trend in the scoring.

20. The system of claim 18, wherein the computer determining the one or more suitable meniscus prosthetic device comprises selecting a smaller meniscus prosthetic device when the scoring identifies two meniscus prosthetic devices of different sizes.

\* \* \* \* \*